US009688794B2

(12) United States Patent
Chen et al.

(10) Patent No.: US 9,688,794 B2
(45) Date of Patent: Jun. 27, 2017

(54) TACKIFIER COMPOUNDS AND METHODS OF USING THE SAME

(71) Applicant: Iowa State University Research Foundation, Inc., Ames, IA (US)

(72) Inventors: Jason Shih-Hao Chen, Ames, IA (US); Michael Richard Kessler, Pullman, WA (US); Michael Dennis Zenner, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 111 days.

(21) Appl. No.: 14/434,719

(22) PCT Filed: Oct. 15, 2013

(86) PCT No.: PCT/US2013/064960
§ 371 (c)(1),
(2) Date: Apr. 9, 2015

(87) PCT Pub. No.: WO2014/062625
PCT Pub. Date: Apr. 24, 2014

(65) Prior Publication Data
US 2015/0274861 A1    Oct. 1, 2015

Related U.S. Application Data

(60) Provisional application No. 61/872,116, filed on Aug. 30, 2013, provisional application No. 61/713,889, filed on Oct. 15, 2012.

(51) Int. Cl.
| | | |
|---|---|---|
| *A01N 43/40* | (2006.01) |
| *C07D 401/00* | (2006.01) |
| *C07D 405/00* | (2006.01) |
| *C08F 122/20* | (2006.01) |
| *C07D 493/04* | (2006.01) |
| *C09J 4/00* | (2006.01) |
| *C08G 18/32* | (2006.01) |
| *C08G 18/77* | (2006.01) |
| *C08L 75/08* | (2006.01) |

(52) U.S. Cl.
CPC .......... *C08F 122/20* (2013.01); *C07D 493/04* (2013.01); *C08G 18/3218* (2013.01); *C08G 18/771* (2013.01); *C08L 75/08* (2013.01); *C09J 4/00* (2013.01); *C08L 2201/50* (2013.01)

(58) Field of Classification Search
CPC ........ C07D 493/04; C09J 4/00; C08F 122/20; C08G 19/771; C08G 18/3218; C08L 75/08; C08L 2201/50
USPC .............................. 514/338; 546/256, 284.1
See application file for complete search history.

(56) References Cited

U.S. PATENT DOCUMENTS

| | | | |
|---|---|---|---|
| 4,013,688 A | 3/1977 | Babcock et al. |
| 4,383,051 A | 5/1983 | Meyborg et al. |
| 4,559,351 A * | 12/1985 | Stoss ................... | C07D 211/90 514/338 |
| 6,737,481 B1 | 5/2004 | Kurian et al. |
| 2001/0023276 A1 | 9/2001 | Schoenfeld |
| 2003/0212244 A1 | 11/2003 | Hayes et al. |

(Continued)

FOREIGN PATENT DOCUMENTS

| | | |
|---|---|---|
| CN | 1384109 A | 12/2002 |
| CN | 103044669 A | 4/2013 |

(Continued)

OTHER PUBLICATIONS

"International Application Serial No. PCT/US2013/064960, International Search Report mailed Feb. 4, 2014", 8 pgs.
"International Application Serial No. PCT/US2013/064960, Written Opinion mailed Feb. 14, 2014", 10 pgs.
"International Application Serial No. PCT/US2013/064972, International Search Report mailed Feb. 4, 2014", 5 pgs.
"International Application Serial No. PCT/US2013/064972, Written Opinion mailed Feb. 4, 2014", 8 pgs.
Bachmann, Frank, et al., "Synthesis of Novel Polyurethanes and Polyureas by Polyaddition Reactions of Dianhydrohexitol Configurated Diisocyanates", Macromol. Chem. Phys., vol. 202, No. 17, (Jan. 1, 2001), 3410-3419.
Barros, Thalita G, et al., "Novel Peptide Mimetics Based on N-protected Amino Acids Derived from Isomannide as Potential Inhibitors of NS3 Serine Protease of Hepatitis C Virus", Letters in Organic Chemistry, vol. 9, No. 4, (Feb. 1, 2012), 239-249.
Beldi, M., et al., "Characterization of cyclic and non-cyclic poly(ether-urethane)s bio-based sugar diols by a combination of MALDI-TOF and NMR", European Polymer Journal, 43, (2007), 3415-3433.

(Continued)

*Primary Examiner* — William Cheung
(74) *Attorney, Agent, or Firm* — Schwegman, Lundberg & Woessner, P.A.

(57) ABSTRACT

The present invention relates to tackifier compounds and methods of using the same. In various embodiments, the present invention provides a tackifier compound including independently substituted or unsubstituted fused rings A and B each independently chosen from ($C_5$-$C_{10}$)cycloalkyl and ($C_2$-$C_{10}$)heterocyclyl. Fused ring A is substituted with ($R^1$)$_{1-8}$ and fused ring B is substituted with —(OC(O)R'C(O)$R^2$)$_{1-8}$. At each occurrence R' is independently chosen from ($C_2$-$C_{10}$)alkanylene, ($C_2$-$C_{10}$)alkenylene, ($C_2$-$C_{10}$)alkynylene, $C_5$-$C_{20}$(arylene), and ($C_1$-$C_{20}$)heteroarylene, wherein R' is unsubstituted or substituted. At each occurrence $R^1$ is independently selected from —OH, —$OR^3$, and —OC(O)R'C(O)$R^2$. At each occurrence $R^2$ is independently chosen from —OH, —$OR^3$, —$NH_2$, —$NHR^3$, and —$NR^3_2$. At each occurrence $R^3$ is independently chosen from ($C_1$-$C_{10}$)alkanyl, ($C_2$-$C_{10}$)alkenyl, ($C_2$-$C_{10}$)alkynyl, $C_5$-$C_{20}$(aryl), and ($C_1$-$C_{20}$)heteroaryl, wherein $R^3$ is unsubstituted or substituted.

19 Claims, No Drawings

(56) References Cited

U.S. PATENT DOCUMENTS

| | | |
|---|---|---|
| 2012/0071577 A1 | 3/2012 | Pfeffer et al. |
| 2012/0073472 A1 | 3/2012 | Spyrou et al. |
| 2015/0274880 A1 | 10/2015 | Chen et al. |
| 2016/0289218 A1 | 10/2016 | Chen et al. |

FOREIGN PATENT DOCUMENTS

| | | |
|---|---|---|
| DE | 102007006442 A1 | 8/2008 |
| EA | 000565 B1 | 12/1999 |
| EP | 0114270 A1 | 8/1984 |
| GB | 985614 | 3/1965 |
| JP | 2002265419 A | 9/2002 |
| KR | 20130070970 A | 6/2013 |
| WO | WO-9636639 A1 | 11/1996 |
| WO | WO-0108677 A1 | 2/2001 |
| WO | WO-2004098538 A2 | 11/2004 |
| WO | WO-2010138842 A1 | 12/2010 |
| WO | WO-2013066461 A2 | 5/2013 |
| WO | WO-2014062625 A1 | 4/2014 |
| WO | WO-2014062631 A1 | 4/2014 |

OTHER PUBLICATIONS

Cocker, J. D, et al., "Action of some steroids on the central nervous system of the mouse. I. Synthetic methods", Journal of Medicinal Chemistry 8(4), (1965).

Feng, Xianhong, et al., "Overview of advances in sugar-based polymers", Polymers for Advanced Technologies, vol. 22, No. 1, (Jan. 10, 2011), 139-150.

Garaleh, Mazen, et al., "(Co-)Polyesters Derived from Isosorbide and 1,4-Cyclohexane Dicarboxylic Acid and Succinic Acid", Macromol. Chem. Phys., 211, (2010), 1206-1214.

Gohil, R. M., "Properties and Strain Hardening Character of Poly-ethylene Terephthalate Containing Isosorbide", Polymer Engineering and Science, (2009), 544-553.

Hojabri, L., et al., "Novel Long Chain Unsaturated Diisocyanate from Fatty Acid: Synthesis, Characterization, and Application in Bio-Based Polyurethane", Journal of Polymer Science: Part A: Polymer Chemistry, vol. 48, (2010), 3302-3310.

Hojabri, Leila, et al., "Fatty Acid-Derived Diisocyanate and Biobased Polyurethane Produced from Vegetable Oil: Synthesis, Polymerization, and Characterization", Biomacromolecules, 10, (1009), 884-891.

Hojabri, Leila, et al., "Novel Long Chain Unsaturated Diisocyanate from Fatty Acid: Synthesis, Characterization, and Application in Bio-Based Polyurethane", Journal of Polymer Science: Part A: Polymer Chemistry, 48, (2010), 3302-3310.

Imm, Sebastian, et al., "Improved Ruthenium-Catalyzed Amination of Alcohols with Ammonia: Synthesis of Diamines and Amino Esters", Angew. Chem. Int. Ed., 50, (2011), 7599-7603.

Lee, Chi-Han, et al., "Synthesis, Characterization, and Properties of Polyurethanes Containing 1,4:3,6-Dianhydro-D-sorbitol", Journal of Polymer Science: Part A: Polymer Chemistry, 47, (2009), 6025-6031.

Li, Ruilin, et al., "Synthesis and antifertility activities of A-nor-steroidal compounds", Yiyao Gongye, 17(9), (1987).

Marin, Romina, et al., "Carbohydrate-Based Poly(ester-urethane)s: A Comparative Study Regarding Cyclic Alditols Extenders and Polymerization Procedures", Journal of Applied Polymer Science, 114, (2009), 3723-3736.

Min, Zhen Li, et al., "Asymmetric synthesis of 3-butylphthalide using isomannide and isosorbide as chiral auxiliaries", Chinese Chemical Letters, vol. 18, No. 11, (Nov. 5, 2007), 1361-1363.

Nakamura, Yoshinobu, et al., "Effects of the Compatibility of a Polyacrylic Block Copolymer/Tackifier Blend on the Phase Structure and Tack of a Pressure-Sensitive Adhesive", Journal of Applied Polymer Science, vol. 123, No. 5, (Mar. 5, 2012), 2883-2893.

Rose, Marcus, et al., "Isosorbide as a Renewable Platform chemical for Versatile Applications—Quo Vadis?", ChemSusChem, 5, (2012), 167-176.

Sabiong, Rafaei, et al., "Incorporation of Isosorbide into Poly(butyiene terephthalate) via Solid-State Polymerization", Macromolecules, American Chemical Society, vol. 9, (Nov. 10, 2008), 3090-3097.

Scalia, Santo, et al., "HPLC determination of ursodeoxycholic acid disuccinate in tablet formulations", (1991).

Thiem, Joachim, et al., "Synthesis and properties of polyurethanes derived from diaminodianhydroalditols", Makromol. Chem., 187, (1986), 2775-2785.

Varkey, Elizabeth Chirackal, et al., "Isosorbide based chiral poly-urethanes: optical and thermal studies", Journal of Materials Science, vol. 45, No. 7, (Jan. 13, 2010), 1912-1920.

Zenner, Michael D, et al., "Polyurethanes from Isosorbide-Based Diisocyanates", ChemSusChem, 6, (2013), 1182-1185.

"U.S. Appl. No. 14/434,710, Notice of Allowance mailed Sep. 21, 2016", 9 pgs.

"U.S. Appl. No. 14/434,710, Response filed Aug. 24, 2016 to Restriction Requirement mailed Jul. 6, 2016", 12 pgs.

"U.S. Appl. No. 14/434,710, Restriction Requirement mailed Jul. 6, 2016", 10 pgs.

"International Application Serial No. PCT/US2013/064960, International Preliminaly Report on Patentability mailed Apr. 30, 2015", 12 pgs.

"International Application Serial No. PCT/US2013/064972, International Preliminary Report on Patentability mailed Apr. 30, 2015", 10 pgs.

\* cited by examiner

US 9,688,794 B2

TACKIFIER COMPOUNDS AND METHODS OF USING THE SAME

CROSS-REFERENCE TO RELATED APPLICATIONS

This application is a U.S. National Stage Filing under 35 U.S.C. 371 from International Application No. PCT/US2013/064960, filed on 15 Oct. 2013 and published as WO 2014/062625 on 24 Apr. 2014, which claims the benefit of priority to U.S. Provisional Patent Application Ser. No. 61/872,116 entitled "TACKIFIER COMPOUNDS AND METHODS OF USING THE SAME," filed Aug. 30, 2013, and also claims the benefit of priority to U.S. Provisional Patent Application Ser. No. 61/713,889 entitled "POLYISOCYANATES FROM FUSED BICYCLIC POLYOLS AND POLYURETHANES THEREFROM," filed Oct. 15, 2012, which applications and publications are incorporated herein in their entirety by reference.

BACKGROUND OF THE INVENTION

Tackifiers are materials that have a characteristic of immediate tackiness or stickiness. Tackifiers can be used in a wide variety of applications, and often form a major component of adhesive compositions. Examples of tackifiers include rosins, terpenes and modified terpenes, petroleum-derived resins, terpene-phenol resins, and silicone resins. Tackifiers can be expensive, and are frequently the most costly component of adhesive formulations. Tackifiers are frequently derived from non-biorenewable materials.

SUMMARY OF THE INVENTION

In various embodiments, the present invention provides a tackifier compound having the structural formula

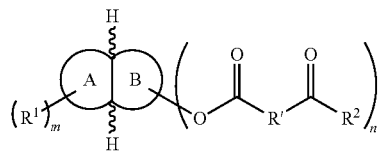

or a salt thereof. Fused rings A and B are each independently chosen from $(C_5\text{-}C_{10})$cycloalkyl and $(C_2\text{-}C_{10})$heterocyclyl. The variables m and n are each independently 1-8. At each occurrence $R^1$ is independently selected from —OH, —OR$^3$, and

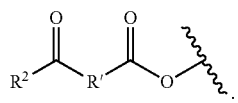

At each occurrence R' is independently chosen from $(C_2\text{-}C_{10})$alkanylene, $(C_2\text{-}C_{10})$alkenylene, $(C_2\text{-}C_{10})$alkynylene, $C_5\text{-}C_{20}$(arylene), and $(C_1\text{-}C_{20})$heteroarylene, wherein R' is unsubstituted or substituted with at least one J. At each occurrence $R^2$ is independently chosen from —OH, —OR$^3$, —NH$_2$, —NHR$^3$, and —NR$^3{}_2$. At each occurrence $R^3$ is independently chosen from $(C_1\text{-}C_{10})$alkanyl, $(C_2\text{-}C_{10})$alkenyl, $(C_2\text{-}C_{10})$alkynyl, $C_5\text{-}C_{20}$(aryl), and $(C_1\text{-}C_{20})$heteroaryl, wherein $R^3$ is unsubstituted or substituted with at least one J. Fused rings A and B are each independently unsubstituted or substituted with at least one of J, $(C_1\text{-}C_{10})$alkyl, $(C_2\text{-}C_{10})$alkenyl, $(C_2\text{-}C_{10})$alkynyl, $(C_1\text{-}C_{10})$haloalkyl, $(C_1\text{-}C_{10})$alkoxy, $(C_1\text{-}C_{10})$haloalkoxy, $(C_1\text{-}C_{10})$cycloalkyl$(C_0\text{-}C_{10})$alkyl, $(C_1\text{-}C_{10})$heterocyclyl$(C_0\text{-}C_{10})$alkyl, $(C_1\text{-}C_{10})$aryl$(C_0\text{-}C_{10})$alkyl, or $(C_1\text{-}C_{10})$heteroaryl$(C_0\text{-}C_{10})$alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J. The variable J independently at each occurrence is chosen from F, Cl, Br, I, OR, CN, CF$_3$, OCF$_3$, R, O, S, C(O), S(O), methylenedioxy, ethylenedioxy, N(R)$_2$, SR, S(O)R, SO$_2$R, SO$_2$N(R)$_2$, SO$_3$R, C(O)R, C(O)C(O)R, C(O)CH$_2$C(O)R, C(S)R, C(O)OR, OC(O)R, OC(O)OR, C(O)N(R)$_2$, OC(O)N(R)$_2$, C(S)N(R)$_2$, (CH$_2$)$_{0\text{-}2}$NHC(O)R, N(R)N(R)C(O)R, N(R)N(R)C(O)OR, N(R)N(R)C(O)N(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(C(O)R)C(O)R, N(OR)R, C(=NH)N(R)$_2$, C(O)N(OR)R, and C(=NOR)R, wherein R is independently at each occurrence chosen from hydrogen, $(C_1\text{-}C_{10})$alkyl, $(C_1\text{-}C_{10})$cycloalkyl, $(C_1\text{-}C_{10})$cycloalkyl$(C_1\text{-}C_{10})$alkyl, $(C_1\text{-}C_{10})$aryl, $(C_1\text{-}C_{10})$aralkyl, $(C_1\text{-}C_{10})$heterocyclyl, $(C_1\text{-}C_{10})$heterocyclyl$(C_1\text{-}C_{10})$alkyl, $(C_1\text{-}C_{10})$heteroaryl, and $(C_1\text{-}C_{10})$heteroaryl$(C_1\text{-}C_{10})$alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

In various embodiments, the present invention provides a polymer comprising a repeating unit having the structure

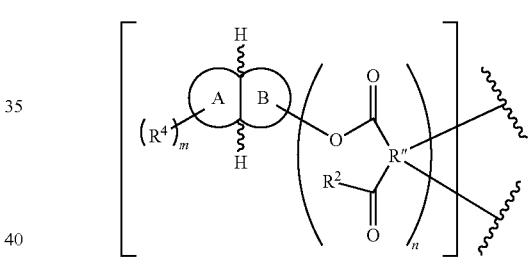

or a salt thereof. Fused rings A and B are each independently chosen from $(C_5\text{-}C_{10})$cycloalkyl and $(C_2\text{-}C_{10})$heterocyclyl. The variables m and n are each independently 1-8. At each occurrence $R^4$ is independently selected from —OH, —OR$^3$,

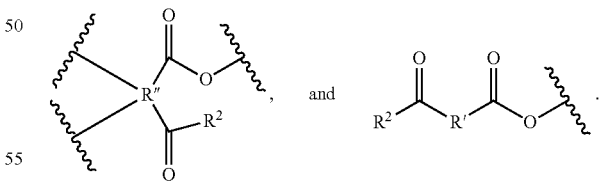

At each occurrence R' is independently chosen from $(C_2\text{-}C_{10})$alkanylene, $(C_2\text{-}C_{10})$alkenylene, $(C_2\text{-}C_{10})$alkynylene, $C_5\text{-}C_{20}$(arylene), and $(C_1\text{-}C_{20})$heteroarylene, wherein R' is unsubstituted or substituted with at least one J. At each occurrence R" is independently a $(C_2\text{-}C_{10})$alkanylene bonded to at least one of a repeating unit and an end-blocking unit of the polymer at two locations, wherein R" is unsubstituted or substituted with at least one J. At each occurrence $R^2$ is independently chosen from —OH, —OR$^3$, —NH$_2$, —NHR$^3$, and —NR$^3{}_2$. At each occurrence $R^3$ is independently chosen from $(C_1-C_{10})$alkanyl, $(C_2-C_{10})$alkenyl, $(C_2-C_{10})$alkynyl, $C_5-C_{20}$(aryl), and $(C_1-C_{20})$heteroaryl, wherein $R^3$ is unsubstituted or substituted with at least one J. Fused rings A and B are each independently unsubstituted or substituted with at least one of J, $(C_1-C_{10})$ alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl $(C_0-C_{10})$alkyl, $(C_1-C_{10})$heterocyclyl$(C_0-C_{10})$alkyl, $(C_1-C_{10})$aryl$(C_0-C_{10})$alkyl, or $(C_1-C_{10})$heteroaryl$(C_0-C_{10})$alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J. The variable J independently at each occurrence is chosen from F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, C(O)CH_2C(O)R, C(S)R, C(O)OR, OC(O)R, OC(O)OR, C(O)N$(R)_2$, $OC(O)N(R)_2$, $C(S)N(R)_2$, $(CH_2)_{0-2}$NHC(O)R, N(R)N(R)C(O)R, N(R)N(R)C(O)OR, $N(R)N(R)C(O)N(R)_2$, N(R)$SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(C(O)R)C(O)R, N(OR)R, $C(=NH)N(R)_2$, C(O)N(OR)R, and C(=NOR)R, wherein R is independently at each occurrence chosen from hydrogen, $(C_1-C_{10})$alkyl, $(C_1-C_{10})$cycloalkyl, $(C_1-C_{10})$cycloalkyl$(C_1-C_{10})$alkyl, $(C_1-C_{10})$aryl, $(C_1-C_{10})$aralkyl, $(C_1-C_{10})$heterocyclyl, $(C_1-C_{10})$heterocyclyl$(C_1-C_{10})$alkyl, $(C_1-C_{10})$heteroaryl, and $(C_1-C_{10})$heteroaryl$(C_1-C_{10})$alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

In various embodiments, the present invention provides a system including the tackifier compound having the structure

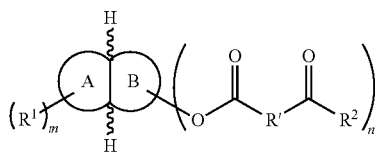

or the salt thereof. The system also includes a first substrate. The tackifier compound is bonded to the first substrate.

In various embodiments, the present invention provides a system including the polymer including a repeating unit having the structure

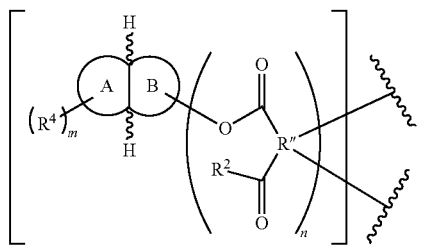

or the salt thereof. The system also includes a first substrate. The polymer is bonded to the first substrate.

In various embodiments, the present invention provides a method of using the tackifier compound having the structure

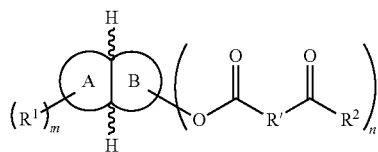

or the salt thereof. The method includes contacting the tackifier compound to a first substrate such that the tackifier is bonded to the first substrate.

In various embodiments, the present invention provides a method of making the tackifier compound. The method includes contacting a compound having the structure

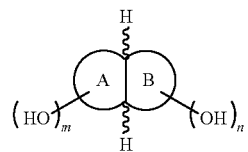

and an acid anhydride having the structure

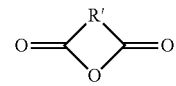

to provide the tackifier compound having the structure

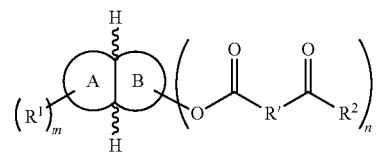

or the salt thereof.

In various embodiments, the present invention provides certain advantages over other tackifier compounds or methods of making and using tackifier compounds, at least some of which are unexpected. For example, in some embodiments, the tackifier compound can have greater tackiness than other tackifiers. In some embodiments, the tackifier compound can be made for a lower cost than other tackifiers, or at a cost competitive with that of other tackifiers. In some embodiments, the tackifier can provide a greater amount of tackiness for a particular cost than that provided by other tackifiers. In some embodiments, the method of making the tackifier compound can require little to no purification, providing a method that requires less purification than other methods. In some embodiments, the properties of the tackifier, such as solubility in water, glass transition temperature, and tackiness, can be more easily adjusted or tuned by varying the starting materials than is possible with other tackifiers. In some embodiments, the tackifier is also useful as a rheology modifier, such as a thickener or viscosifier, such as in organic liquids, oils, or aqueous liquids.

In some embodiments, the tackifier compound can be generated from biorenewable sources. In some embodiments, the tackifier compound can be generated from more readily available or cheaper biorenewable sources than other tackifiers. In some embodiments, the tackifier compound can be generated from biorenewable sources more easily and with less cost than other tackifiers. In some embodiments, the tackifier compound can be made from a greater proportion of biorenewable materials than other tackifiers. In some embodiments, the method of making the tackifier can be more environmentally friendly than other methods; for example, in some embodiments, the method can use less solvent or can generate less waste than other procedures. In some embodiments, the tackifier compound can cost less than or can have a cost competitive with the cost of petroleum-derived tackifiers. In some embodiments, the process of making the tackifier can be more easily scalable than other methods, such as other methods of making tackifiers from biorenewable sources. In some embodiments, the method of making the tackifier compound can transform a compound, such as isosorbide, isomannide, or isoidide, into a useful substance for a lower cost, greater convenience, or with less environmental impact, than other methods of transforming of modifying the compound.

In some embodiments, unlike other tackifiers, the tackifier can be a curable tackifier that hardens into a strongly-bonding material. In some embodiments, the property of curability can provide a greater number of or different types of uses than those practically available with other tackifiers. In some embodiments, curability can allow for modification of properties via a variety of external stimuli. In some embodiments, the curable tackifier can be cured using different methods or using a greater variety of methods than possible with other tackifiers. In some embodiments, unlike other tackifiers, the curable property of the tackifier can allow the tackifier to serve as a greater proportion of an adhesive composition or as substantially the only component of an adhesive composition.

DETAILED DESCRIPTION OF THE INVENTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

Selected substituents within the compounds described herein are present to a recursive degree. In this context, "recursive substituent" means that a substituent may recite another instance of itself or of another substituent that itself recites the first substituent. Recursive substituents are an intended aspect of the disclosed subject matter. Because of the recursive nature of such substituents, theoretically, a large number may be present in any given claim. One of ordinary skill in the art of organic chemistry understands that the total number of such substituents is reasonably limited by the desired properties of the compound intended. Such properties include, by way of example and not limitation, physical properties such as molecular weight, solubility, and practical properties such as ease of synthesis. Recursive substituents can call back on themselves any suitable number of times, such as about 1 time, about 2 times, 3, 4, 5, 6, 7, 8, 9, 10, 15, 20, 30, 50, 100, 200, 300, 400, 500, 750, 1000, 1500, 2000, 3000, 4000, 5000, 10,000, 15,000, 20,000, 30,000, 50,000, 100,000, 200,000, 500,000, 750,000, or about 1,000,000 times or more.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "organic group" as used herein refers to but is not limited to any carbon-containing functional group. For example, an oxygen-containing group such as alkoxy groups, aryloxy groups, aralkyloxy groups, oxo(carbonyl) groups, carboxyl groups including carboxylic acids, carboxylates, and carboxylate esters; a sulfur-containing group such as alkyl and aryl sulfide groups; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein R can be hydrogen (in examples that include other carbon atoms) or a carbon-based moiety, and wherein the carbon-based moiety can itself be further substituted.

The term "substituted" as used herein refers to an organic group as defined herein or molecule in which one or more hydrogen atoms contained therein are replaced by one or more non-hydrogen atoms. The term "functional group" or "substituent" as used herein refers to a group that can be or is substituted onto a molecule, or onto an organic group. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR, OC(O)N(R')$_2$, CN, NO, NO$_2$, ONO$_2$, azido, CF$_3$, OCF$_3$, R', O(oxo), S(thiono), C(O), S(O), methylenedioxy, ethylenedioxy, N(R)$_2$, SR, SOR, SO$_2$R', SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted with J; or wherein two R groups bonded to a nitrogen atom or to adjacent nitrogen atoms can together with the nitrogen atom or atoms form a heterocyclyl, which can be mono- or independently multi-substituted with J.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 or 12-40 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-, 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl group are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl(1-anthracenyl, 2-anthracenyl, 3-anthracenyl), thiophenyl(2-thienyl, 3-thienyl), furyl(2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl(2-pyrrolyl), pyrazolyl(3-pyrazolyl), imidazolyl(1-imidazolyl, 2-imidazolyl, 4-imidazolyl, 5-imidazolyl), triazolyl(1,2,3-triazol-1-yl, 1,2,3-triazol-2-yl 1,2,3-triazol-4-yl, 1,2,4-triazol-3-yl), oxazolyl(2-oxazolyl, 4-oxazolyl, 5-oxazolyl), thiazolyl(2-thiazolyl, 4-thiazolyl, 5-thiazolyl), pyridyl(2-pyridyl, 3-pyridyl, 4-pyridyl), pyrimidinyl(2-pyrimidinyl, 4-pyrimidinyl, 5-pyrimidinyl, 6-pyrimidinyl), pyrazinyl, pyridazinyl(3-pyridazinyl, 4-pyridazinyl, 5-pyridazinyl), quinolyl(2-quinolyl, 3-quinolyl, 4-quinolyl, 5-quinolyl, 6-quinolyl, 7-quinolyl, 8-quinolyl), isoquinolyl(1-isoquinolyl, 3-isoquinolyl, 4-isoquinolyl, 5-isoquinolyl, 6-isoquinolyl, 7-isoquinolyl, 8-isoquinolyl), benzo[b]furanyl(2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl(2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl(2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl(1-indolyl, 2-indolyl, 3-indolyl, 4-indolyl, 5-indolyl, 6-indolyl, 7-indolyl), indazole(1-indazolyl, 3-indazolyl, 4-indazolyl, 5-indazolyl, 6-indazolyl, 7-indazolyl), benzimidazolyl(1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl(1-benzoxazolyl, 2-benzoxazolyl), benzothiazolyl(1-benzothiazolyl, 2-benzothiazolyl, 4-benzothiazolyl, 5-benzothiazolyl, 6-benzothiazolyl, 7-benzothiazolyl), carbazolyl(1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine(10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" group, as used herein, by themselves or as part of another substituent mean, unless otherwise stated, a fluorine, chlorine, bromine, or iodine atom, preferably, fluorine, chlorine, or bromine The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" as used herein refers to a functional group or molecule that includes carbon and hydrogen atoms. The term can also refer to a functional group or molecule that normally includes both carbon and hydrogen atoms but wherein all the hydrogen atoms are substituted with other functional groups.

The term "resin" as used herein refers to polysiloxane material of any viscosity that includes at least one siloxane monomer that is bonded via a Si—O—Si bond to three or four other siloxane monomers. In one example, the polysiloxane material includes T or Q groups, as defined herein.

The term "number-average molecular weight" as used herein refers to the ordinary arithmetic mean of the molecular weight of individual molecules in a sample. It is defined as the total weight of all molecules in a sample divided by the total number of molecules in the sample. Experimentally, the number-average molecular weight ($M_n$) is determined by analyzing a sample divided into molecular weight fractions of species i having $n_i$ molecules of molecular weight $M_i$ through the formula $M_n = \Sigma M_i n_i / \Sigma n_i$. The number-average molecular weight can be measured by a variety of well-known methods including gel permeation chromatography, spectroscopic end group analysis, and osmometry. If unspecified, molecular weights of polymers given herein are number-average molecular weights.

The term "weight-average molecular weight" as used herein refers ($M_w$), which is equal to $\Sigma M_i^2 n_i / \Sigma M_i n_i$ where $n_i$ is the number of molecules of molecular weight $M_i$. In various examples, the weight-average molecular weight can be determined using light scattering, small angle neutron scattering, X-ray scattering, and sedimentation velocity.

The term "radiation" as used herein refers to energetic particles travelling through a medium or space. Examples of radiation are visible light, infrared light, microwaves, radio waves, very low frequency waves, extremely low frequency waves, thermal radiation (heat), and black-body radiation.

The term "cure" as used herein refers to exposing to radiation in any form, heating, or allowing to undergo a physical or chemical reaction that results in hardening or an increase in viscosity.

The term "solvent" as used herein refers to a liquid that can dissolve a solid, liquid, or gas. Nonlimiting examples of solvents are silicones, organic compounds, water, alcohols, ionic liquids, and supercritical fluids.

The term "silicate" as used herein refers to any silicon-containing compound wherein the silicon atom has four bonds to oxygen, wherein at least one of the oxygen atoms bound to the silicon atom is ionic, such as any salt of a silicic acid. The counterion to the oxygen ion can be any other suitable ion or ions. An oxygen atom can be substituted with other silicon atoms, allowing for a polymer structure. One or more oxygen atoms can be double-bonded to the silicon atom; therefore, a silicate molecule can include a silicon atom with 2, 3, or 4 oxygen atoms. Examples of silicates include aluminum silicate. Zeolites are one example of materials that can include aluminum silicate. A silicate can be in the form of a salt or ion.

Herein, when it is designated that a variable in the structure can be "a bond," the variable can represent a direct bond between the two groups shown as linked to that variable, such as a single bond.

The term "polymer" as used herein can include a copolymer.

Tackifier.

In various embodiments, the present invention provides a tackifier compound having the structural formula

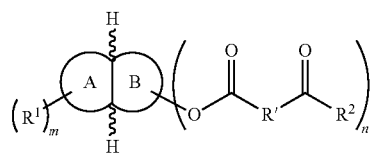

or a salt thereof. In some embodiments, none of the acid moieties are present as a salt, one of the acid moieties is present as a salt, or two or more of the acid moieties are present as a salt. The salt can have any suitable counterion, for example, $Na^+$, $K^+$, $Ag^+$, $NH_4^+$, or multiple acid moieties can share a common ion, such as $Al^{3+}$, $Ca^{2+}$, $Cu^{2+}$, $Fe^{2+}$, $Fe^{3+}$, and $Mg^{2+}$. In some embodiments, the compound is not a salt.

At each occurrence the variable $R^1$ can be independently selected from —OH, —OR³, and

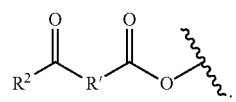

In some embodiments, the variable $R^1$ can be —OH. In some embodiments, the variable $R^1$ can be

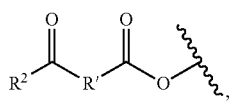

such as

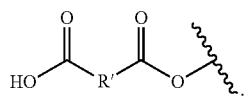

In some embodiments, the tackifier can have the structure

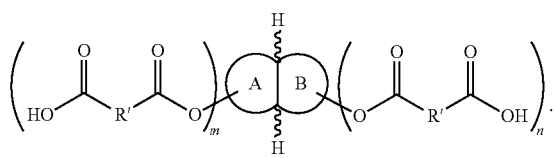

At each occurrence R' can be independently chosen from $(C_2\text{-}C_{10})$alkanylene, $(C_2\text{-}C_{10})$alkenylene, $(C_2\text{-}C_{10})$alkynylene, $C_5\text{-}C_{20}$(arylene), and $(C_1\text{-}C_{20})$heteroarylene, wherein R' can be unsubstituted or substituted with at least one J. In some embodiments, R' is unsubstituted. The variable R' can be $(C_1\text{-}C_5)$alkanylene, such as —$CH_2$-$CH_2$— (ethanylene) or —$CH_2$-$CH_2$-$CH_2$— (propanylene). The variable R' can be $(C_1\text{-}C_5)$alkylene or $(C_2\text{-}C_5)$alkenylene, such as —CH=C— (ethenylene). The variable R' can be $(C_5\text{-}C_{10})$aryl, such as phenylene, such as ortho-substituted phenylene, or napthyl, such as ortho-substituted naphthalene. The variable R' can be $(C_1\text{-}C_{20})$heteroaryl.

At each occurrence the variable $R^2$ can be independently chosen from —OH, —$OR^3$, —$NH_2$, —$NHR^3$, and —$NR^3{}_2$. In some embodiments, $R^2$ can be —OH. In some embodiments, $R^2$ can be —$OR^3$. At each occurrence $R^3$ can be independently chosen from $(C_1\text{-}C_{10})$alkanyl, $(C_2\text{-}C_{10})$alkenyl, $(C_2\text{-}C_{10})$alkynyl, $C_5\text{-}C_{20}$(aryl), and $(C_1\text{-}C_{20})$heteroaryl, wherein $R^3$ is unsubstituted or substituted with at least one J. In some embodiments, the variable $R^3$ can be —OMe.

Fused rings A and B can be each independently chosen from $(C_5\text{-}C_{10})$cycloalkyl and $(C_2\text{-}C_{10})$heterocyclyl. The variables m and n can each independently be 1-8. Fused rings A and B can be each independently unsubstituted or substituted with at least one of J, $(C_1\text{-}C_{10})$alkyl, $(C_2\text{-}C_{10})$alkenyl, $(C_2\text{-}C_{10})$alkynyl, $(C_1\text{-}C_{10})$haloalkyl, $(C_1\text{-}C_{10})$alkoxy, $(C_1\text{-}C_{10})$haloalkoxy, $(C_1\text{-}C_{10})$cycloalkyl$(C_0\text{-}C_{10})$alkyl, $(C_1\text{-}C_{10})$heterocyclyl$(C_0\text{-}C_{10})$alkyl, $(C_1\text{-}C_{10})$aryl$(C_0\text{-}C_{10})$alkyl, or $(C_1\text{-}C_{10})$heteroaryl$(C_0\text{-}C_{10})$alkyl; wherein each alkyl, alkenyl, alkynyl, haloalkyl, alkoxy, haloalkoxy, cycloalkyl, aryl, heterocyclyl, and heteroaryl can be independently unsubstituted or further substituted with at least one J. The variable J independently at each occurrence can be chosen from F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, C(O)$CH_2$C(O)R, C(S)R, C(O)OR, OC(O)R, OC(O)OR, C(O)N$(R)_2$, OC(O)N$(R)_2$, C(S)N$(R)_2$, $(CH_2)_{0\text{-}2}$NHC(O)R, N(R)N(R)C(O)R, N(R)N(R)C(O)OR, N(R)N(R)C(O)N$(R)_2$, N(R)SO$_2$R, N(R)SO$_2$N$(R)_2$, N(R)C(O)OR, N(R)C(O)R, N(R)C(S)R, N(R)C(O)N$(R)_2$, N(R)C(S)N$(R)_2$, N(C(O)R)C(O)R, N(OR)R, C(=NH)N$(R)_2$, C(O)N(OR)R, and C(=NOR)R, wherein R can be independently at each occurrence chosen from hydrogen, $(C_1\text{-}C_{10})$alkyl, $(C_1\text{-}C_{10})$cycloalkyl, $(C_1\text{-}C_{10})$cycloalkyl$(C_1\text{-}C_{10})$alkyl, $(C_1\text{-}C_{10})$aryl, $(C_1\text{-}C_{10})$aralkyl, $(C_1\text{-}C_{10})$heterocyclyl, $(C_1\text{-}C_{10})$heterocyclyl$(C_1\text{-}C_{10})$alkyl, $(C_1\text{-}C_{10})$heteroaryl, and $(C_1\text{-}C_{10})$heteroaryl$(C_1\text{-}C_{10})$alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

In some embodiments, rings A and B are unsubstituted with the exception of the ester substituents —OC(O)—R'—C(O)$R^2$. In some embodiments, m=n=1, and one of the ester substituents including R' and R" is alpha to at least one carbon atom shared by rings A and B. Rings A and B can be the same size. Rings A and B can be 5-membered rings. At least one of rings A and B can include at least one oxygen atom. Each of rings A and B can be a tetrahydrofuran ring, wherein each carbon atom shared by rings A and B has an oxygen atom alpha thereto. In some embodiments, m=n. In some embodiments, m=n=1. Each of each of $R^1$ and the ester substituent —OC(O)—R'—C(O)$R^2$ can be alpha to a different carbon atom shared by each of rings A and B. Rings A and B can form a ring system chosen from isosorbide, isomannide, and isoidide.

In some embodiments, the tackifier compound is chosen from

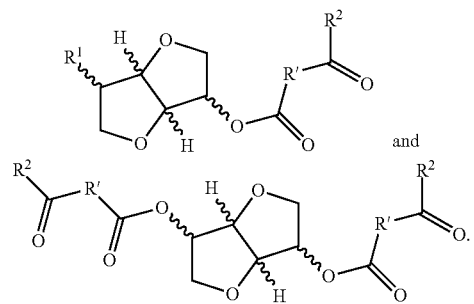

In some embodiments, the tackifier compound has the structure

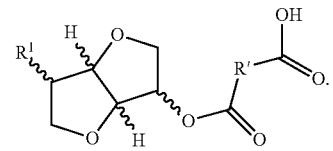

In some embodiments, the tackifier compound has the structure

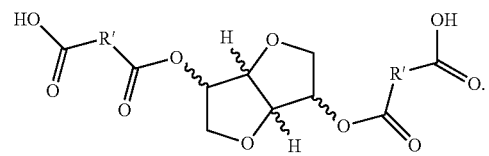

In some embodiments, the tackifier compound can be chosen from

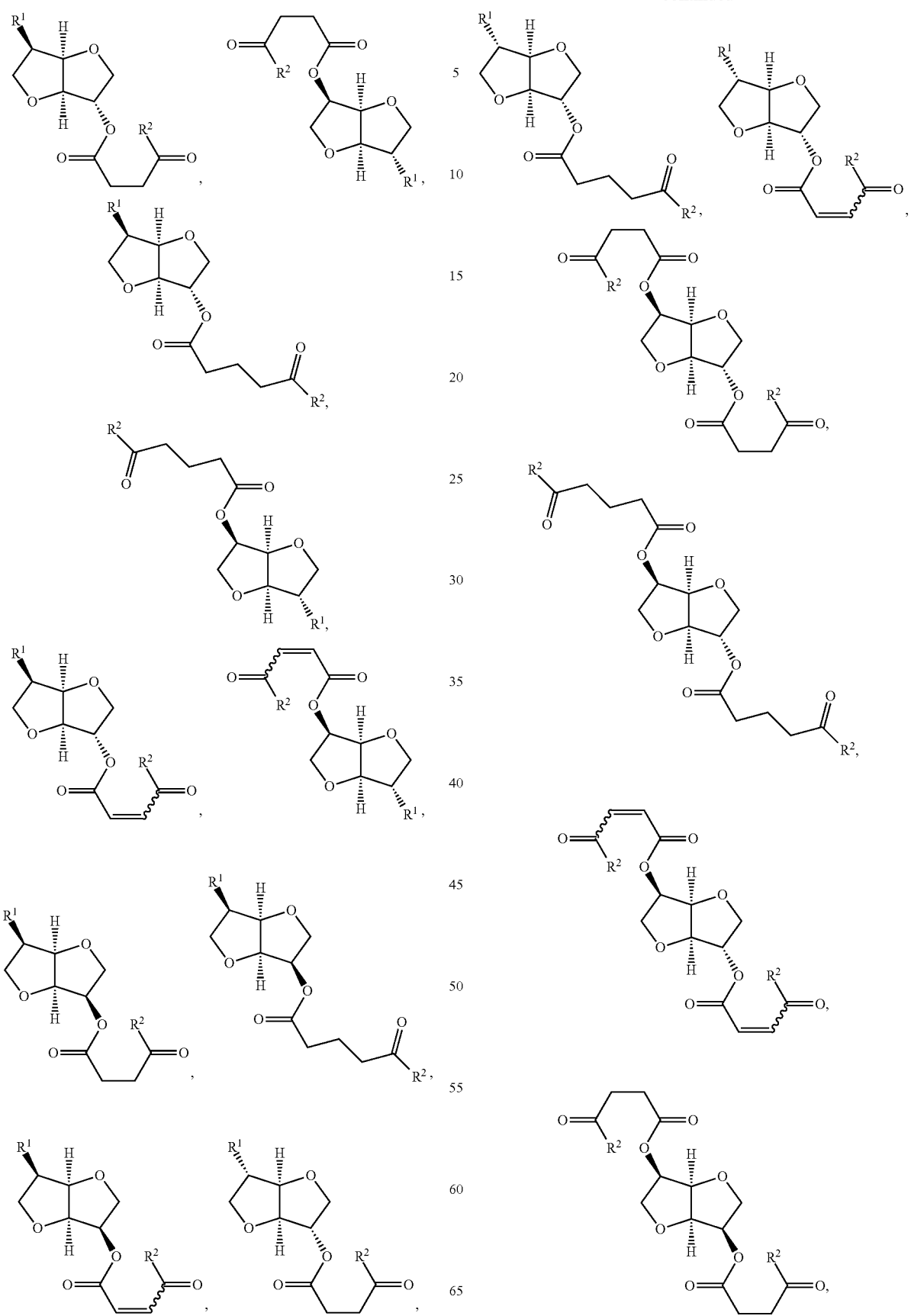

-continued
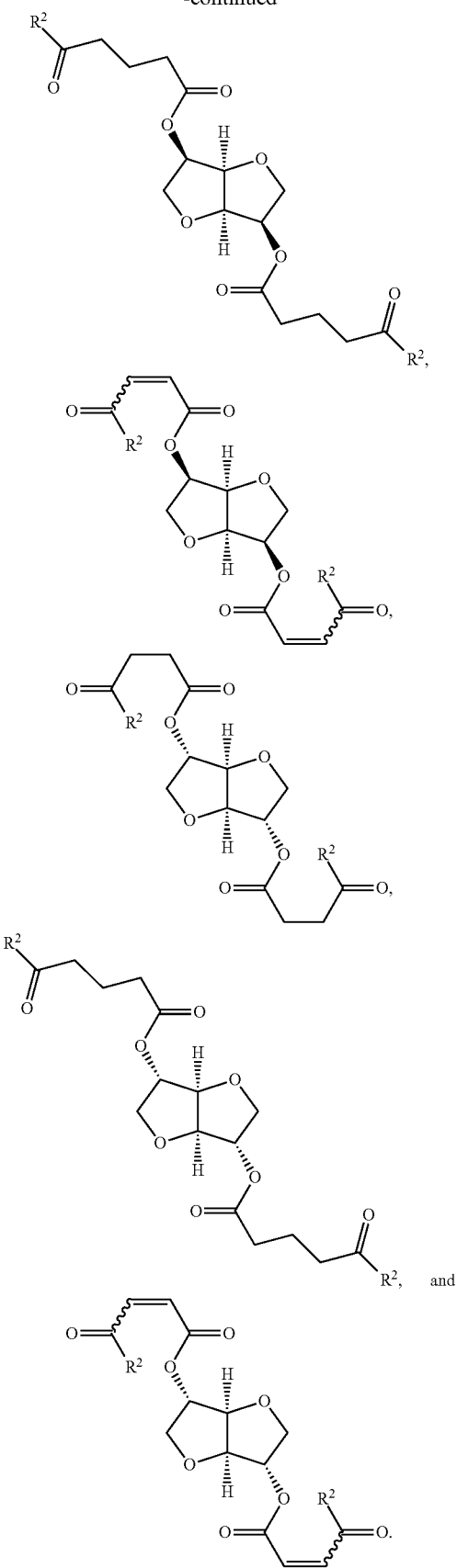
and
In some embodiments, the tackifier compound can be chosen from
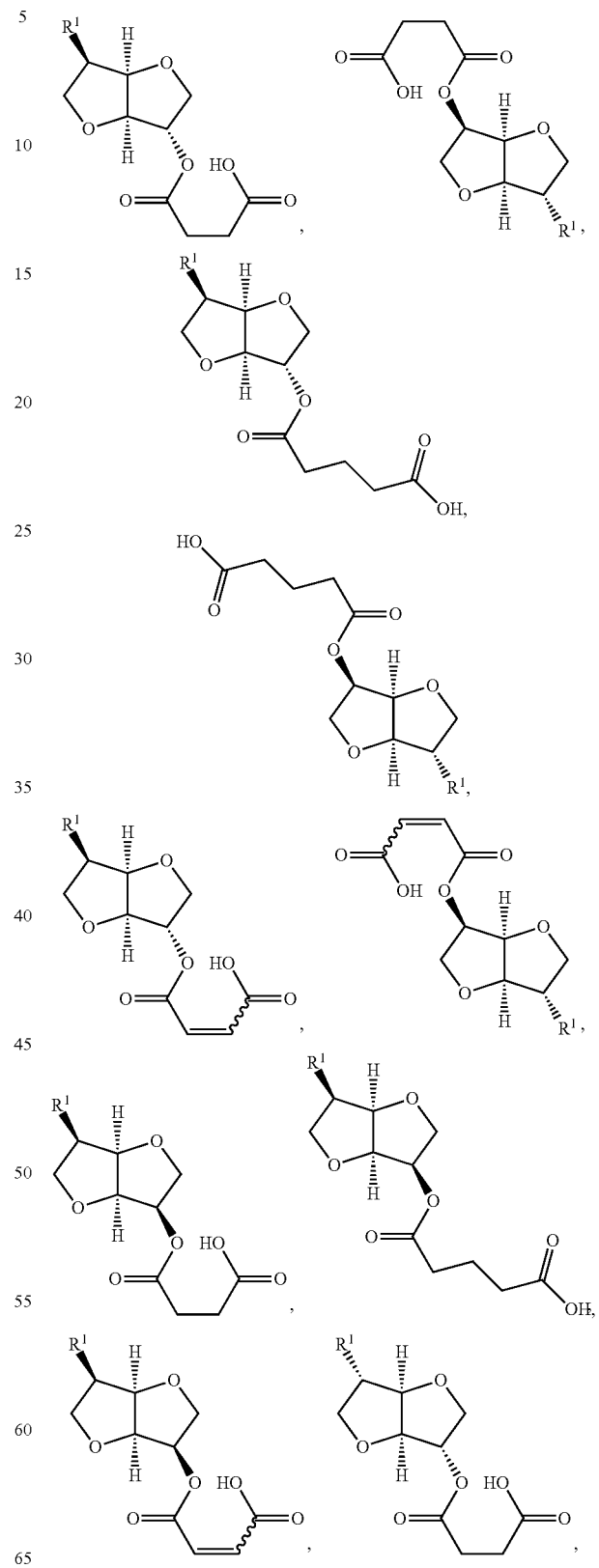

-continued
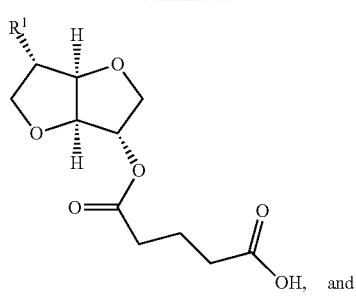
and
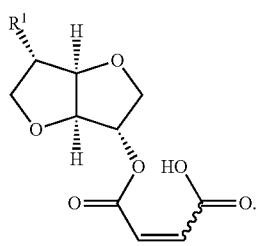
In some embodiments, the tackifier compound can be chosen from
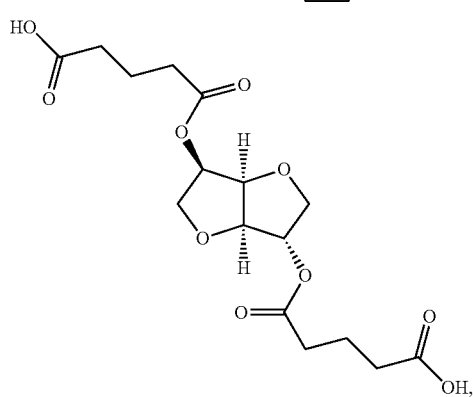
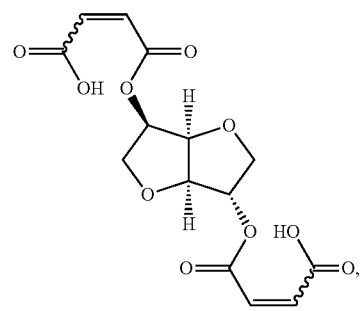 [SMILES: O=C(O)C=CC(=O)O[C@H]1CO[C@H]2[C@@H]1OC[C@@H]2OC(=O)C=CC(=O)O]
-continued
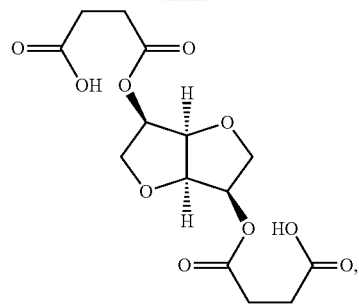
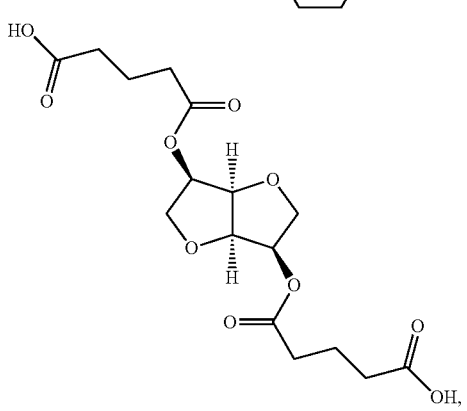
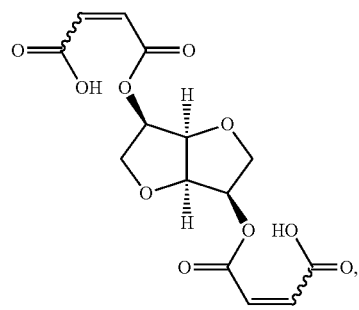
and -continued
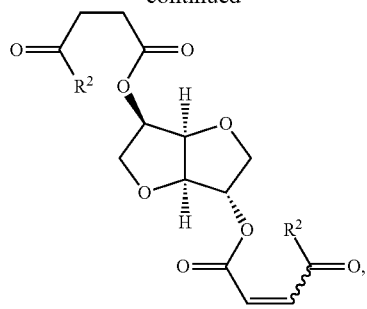
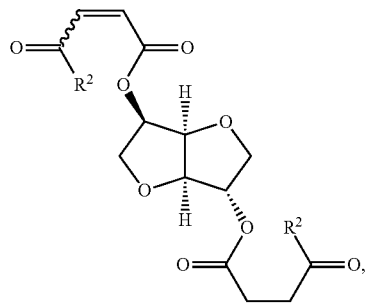
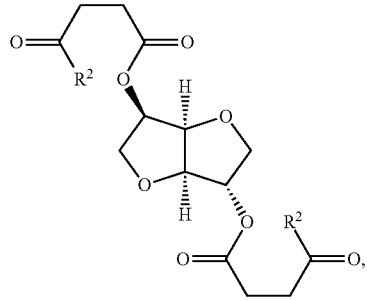
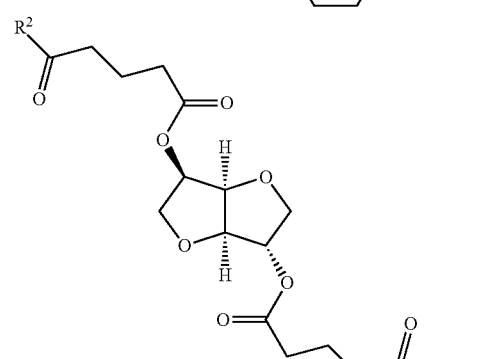
and
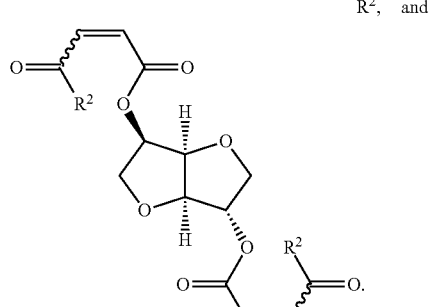
In some embodiments, the tackifier compound can be chosen from
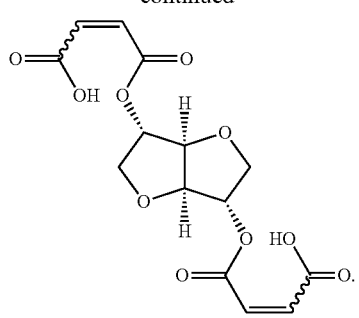
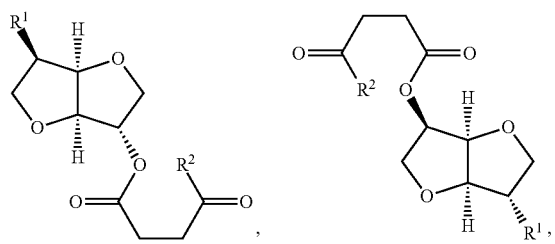
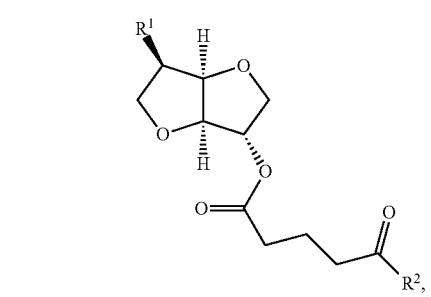
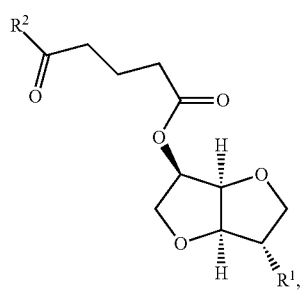
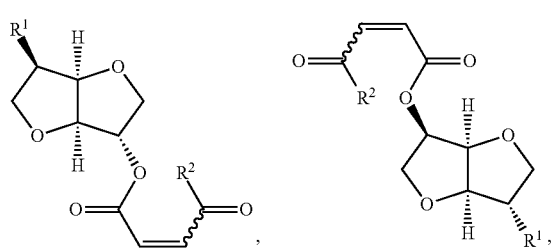
In some embodiments, the tackifier compound can be chosen from

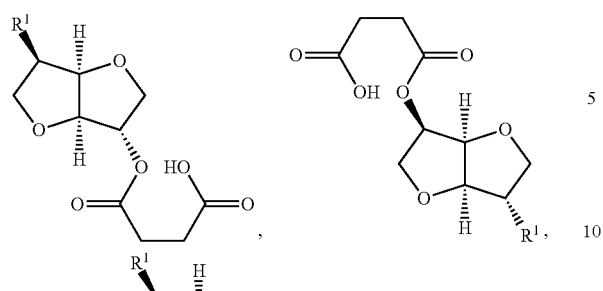
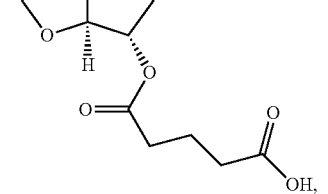
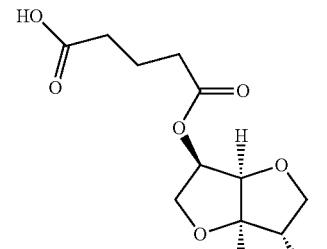
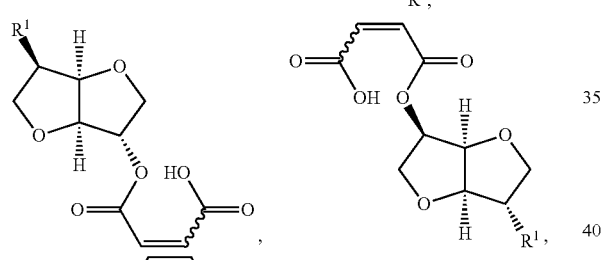
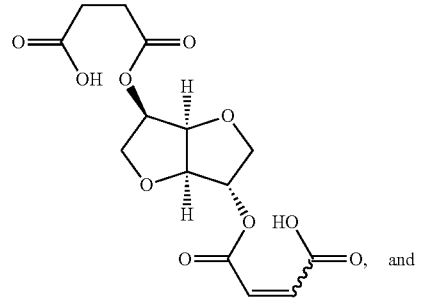
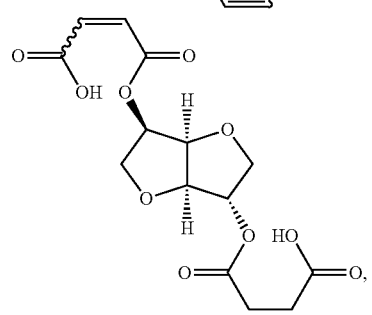
In some embodiments, the tackifier compound can be chosen from
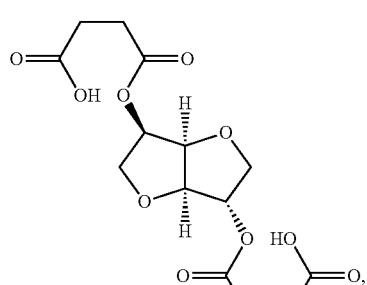
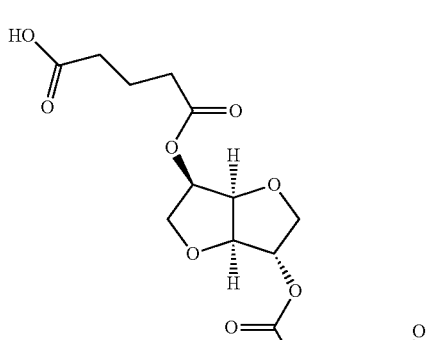
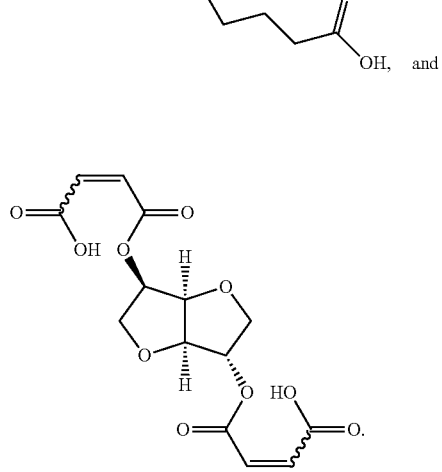
In some embodiments, the tackfier compound does not include
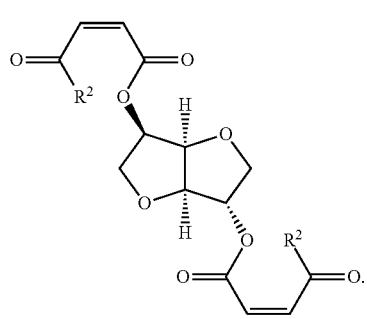
In some embodiments, the tackifier compound does not include

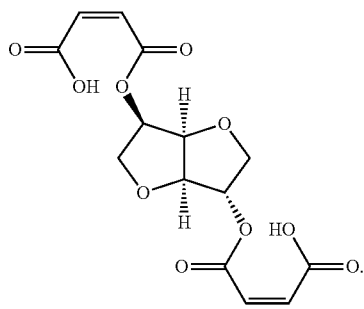 [SMILES: O=C(O)/C=C\C(=O)O[C@H]1CO[C@H]2[C@@H]1OC[C@H]2OC(=O)/C=C\C(=O)O]

In some embodiments, the tackfier compound does not include

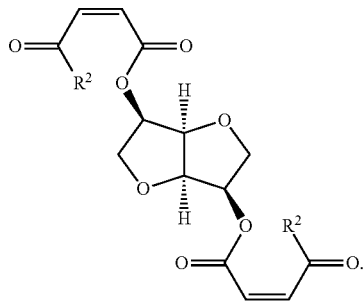

In some embodiments, the tackifier compound does not include

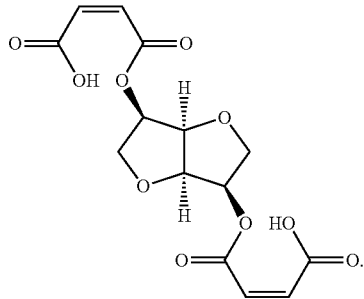 [SMILES: O=C(O)/C=C\C(=O)O[C@@H]1CO[C@H]2[C@@H]1OC[C@H]2OC(=O)/C=C\C(=O)O]

In some embodiments, the tackfier compound does not include

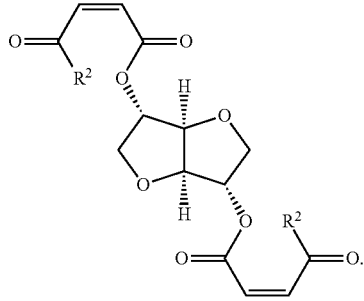

In some embodiments, the tackfier compound does not include

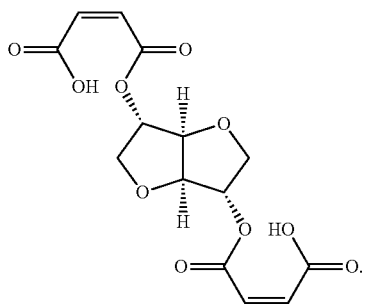 [SMILES: O=C(O)/C=C\C(=O)O[C@H]1CO[C@H]2[C@@H]1OC[C@@H]2OC(=O)/C=C\C(=O)O]

The tackifier compound can have any suitable solubility characteristics. In some embodiments, by altering the substituents or the length of various portions of the compound, the solubility can be changed such that the compound has a solubility that is tuned for a particular use. In some embodiments, the tackifier compound is soluble in organic solvents. The tackifier compound can be soluble in polar solvents, such as water, dimethylformamide, and dimethylsulfoxide. The tackifier compound can be soluble in non-polar solvents, such as hexanes, and benzene. The tackifier compound can be substantially water soluble. The tackifier can be substantially insoluble in water. In some embodiments, the tackifier can have a solubility in water of about 0.000,1 g to about 0.6 g in about 1 mL of water at about 25° C., or about 0.01 g to about 0.3 g dissolve in about 1 mL of water at about 25° C., or about 0.000,1 g or less in 1 mL of water, or about 0.005, 0.01, 0.05, 0.1, 0.15, 0.2, 0.25, 0.3, 0.35, 0.4, 0.45, 0.5, 0.55, or about 0.6 g or more in 1 mL of water at 25° C.

The tackifier compound can have any suitable glass transition temperature ($T_g$). The glass transition temperature corresponds to a temperature at which the tackifier compound undergoes a reversible transition from a hard and relatively brittle state into a molten or rubber-like state. The glass transition temperature can be measured in any suitable way, such as via differential scanning calorimetry. In some embodiments, the tackifier compound has a glass transition temperature of about −90° C. to about 60° C., about −60° C. to about 40° C., or about −35° C. to about 20° C., or about −90° C. or less, or about −80° C., −70, −60, −50, −40, −30, −20, −10, −5, 0, 5, 10, 15, 20, 25, 30, 40, 50° C., or about 60° C. or more.

The tackifier compound can have any suitable tack, which can be measured in any suitable way, such as by the ASTM 02979 standard, as described in the Examples. In some embodiments, the tackifier compound has a tack of about 50 kPa to about 400 kPa, about 75 kPa to about 250 kPa, 100 kPa to about 180 kPa, or about 50 kPa or less, or about 60 kPa, 70, 80, 90, 95, 100, 105, 110, 115, 120, 125, 130, 135, 140, 145, 150, 155, 160, 165, 170, 175, 180, 185, 190, 200, 210, 220, 240, 260, 280, 300, 320, 340, 360, 380, or about 400 kPa or more, at one or more temperatures that are about −40° C. to about 80° C., −5 ° C. to about 55° C., about 5° C. to about 45° C., about 15° C. to about 35° C., or at about −40° C. or less, or about −35° C., −30, −25, −20, −15, −10, −5, 0 , 5, 10, 15, 20, 25, 30, 35, 40, 45, 50, 55, 60, 65, 70, 75° C., or about 80° C. or more.

In some embodiments, the tackifier compound has a tack of about 50 kPa to about 400 kPa, about 75 kPa to about 250 kPa, 120 kPa to about 140 kPa, or about 50 kPa or less, or about 60 kPa, 70, 80, 90, 95, 100, 105, 110, 115, 120, 125, 130, 135, 140, 145, 150, 155, 160, 165, 170, 175, 180, 185, 190, 200, 210, 220, 240, 260, 280, 300, 320, 340, 360, 380, or about 400 kPa or more, at one or more temperatures that are about 20° C. to about 90° C., 40° C. to about 80° C., or about 50° C. to about 70° C., or about 20° C. or less, or about 25° C., 30, 35, 40, 45, 50, 55, 60, 65, 70, 75, 80, 85° C., or about 90° C. or more. In some embodiments, the tackifier compound has a tack of about 200 kPa to about 400 kPa, about 250 kPa to about 300 kPa, or about 200 kPa, 205, 210, 215, 220, 225, 230, 235, 240, 245, 250, 255, 260, 265, 270, 275, 280, 285, 290, 295, 300, 310, 320, 330, 340, 350, 360, 370, 380, 390, or about 400 kPa or more at one or more temperatures that are about −40° C. to about 0° C., or about −30° C. to about −10° C., or about −40 ° C. or less, or about −35° C., −30, −25, −20, −15, −10, −5, or about 0° C. or more.

Curable Tackifier.

In some embodiments, the present invention provides a cured tackifier or a polymer. The cured tackifier can be any tackifier compound described herein in a cured state (e.g., a reaction product of a tackifier compound). For example, the polymer can be a crosslinked tackifier compound, wherein the tackifier compound is crosslinked any suitable way and to any suitable degree, such as highly crosslinked. For example, the curable tackifier compound can include an R' group having curable moieties therein or thereon. In some embodiments, at least one R' can include one or more unsaturated aliphatic carbon-carbon bonds, and can be $C_1$-$C_{10}$ alkenylene or $C_1$-$C_{10}$ alkynylene. The crosslinking of unsaturated aliphatic carbon-carbon bonds can occur in any suitable way. The crosslinking can include at least one of application of radiation, application of heat, addition of a chemical crosslinker, or initiation of chemical crosslinking. The crosslinking can be free-radical polymerization. The crosslinking can be transition metal-catalyzed polymerization. In some embodiments, the crosslinking includes subjecting a tackifier that includes —SH moieties thereon to redox conditions, which can vary the properties in a reversible manner In some embodiments, the crosslinking includes subjecting a tackifier that includes terminal alkynes and a tackifier that includes terminal azides to a copper salt-catalyzed polymerization.

Free-radicals can be generated by any suitable method. Free-radicals can be initiated by, for example, thermal decomposition, photolysis, redox reactions, persulfates, ionizing radiation, electrolysis, plasma, sonication, or a combination thereof. In one example, a free-radical is generated using a free-radical initiator. In one example, the free-radical initiator can be a free-radical photoinitiator, an organic peroxide, or a free-radical initiator activated by heat. Further, a free-radical photoinitiator can be any free-radical photoinitiator capable of initiating cure (cross-linking) of the free-radical polymerizable functional groups upon exposure to radiation, for example, having a wavelength of from 200 to 800 nm. In another example, the free-radical initiator is an organoborane-based free-radical initiator. In one example, the free-radical initiator can be an organic peroxide. For example, elevated temperatures can allow a peroxide to decompose and form a highly reactive radical, which can initiate free-radical polymerization. In some examples, decomposed peroxides and their derivatives can be byproducts. Examples of free-radical initiators can include tert-amyl peroxybenzoate, 4,4-azobis(4-cyanovaleric acid), 1,1'-azobis(cyclohexanecarbonitrile), 2,2'-azobisisobutyronitrile (AIBN), benzoyl peroxide, 2,2-bis-(tert-butylperoxy)butane, 1,1-bis(tert-butylperoxy)cyclohexane, 2,5-bis(tert-butylperoxy)-2,6-dimethylhexane, 2,5-bis(tert-butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, tert-butyl hydroperoxide, tert-butyl peracetate, tert-butyl peroxybenzoate, tert-butylperoxy isopropyl carbonate, cumene hydroperoxide, cyclohexanone peroxide, dicumyl peroxide, lauroyl peroxide, 2,4-pentanedione peroxide, peracetic acid, or potassium persulfate. In some embodiments, the present invention provides a composition including a free-radical-curable tackifier compound and a free-radical initiator.

A transition metal catalyst can be any suitable transition metal catalyst. For example, a Ziegler-Natta catalyst, or a Phillips catalyst.

In various embodiments, the polymer can be a reaction product, such as a free-radical polymerization product, of at least one tackifier compound chosen from

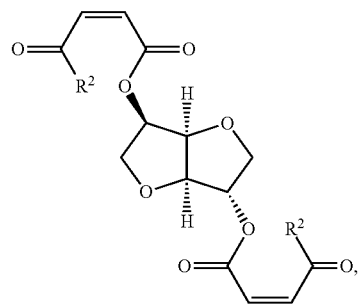

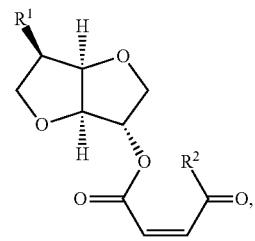

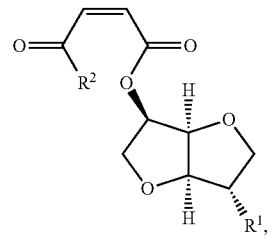

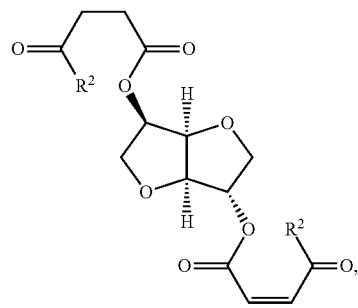

29
-continued
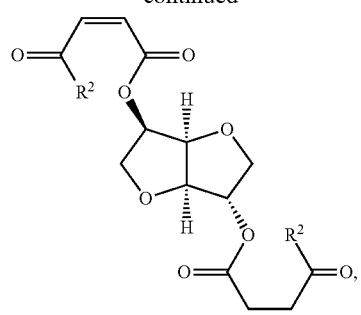
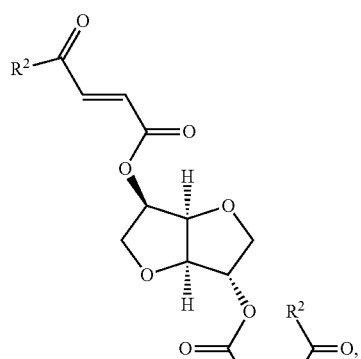
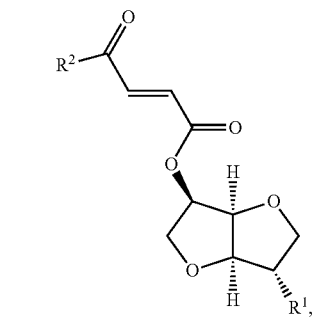
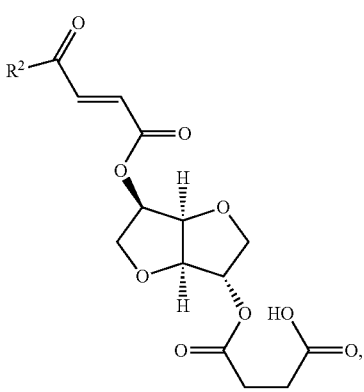
30
-continued
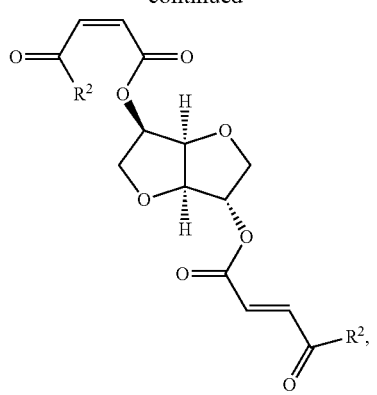
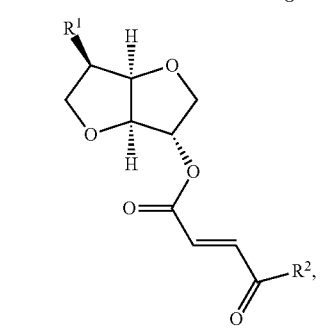
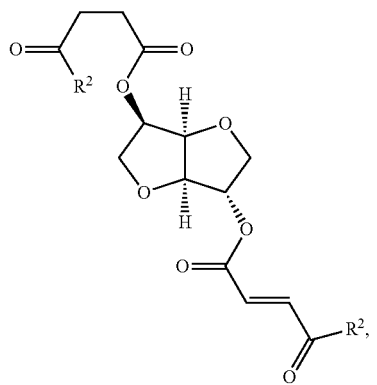
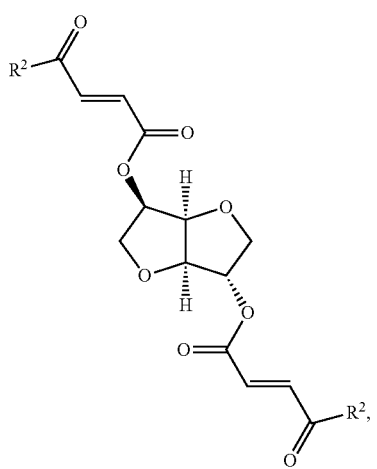

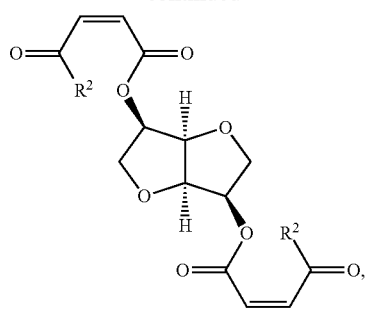
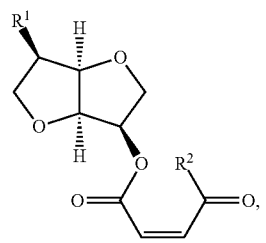
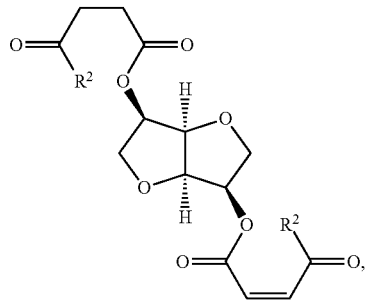
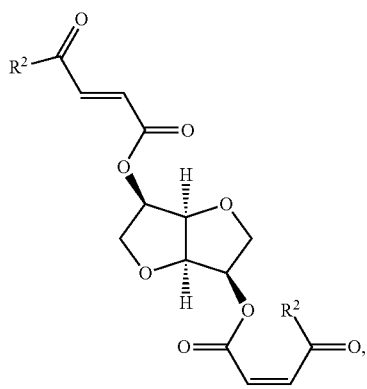
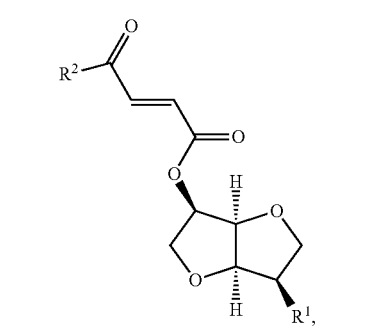
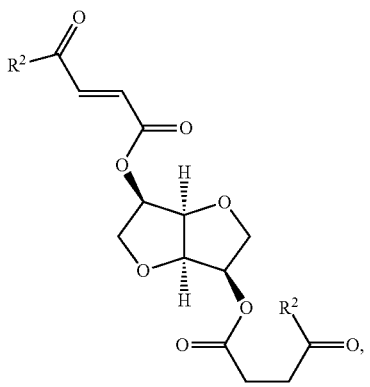
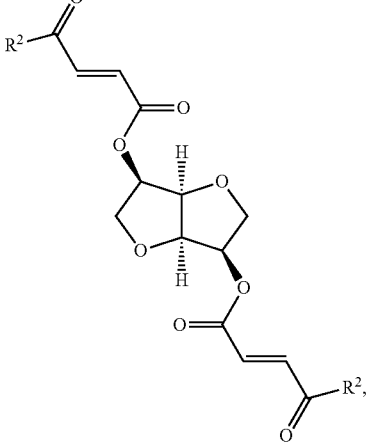
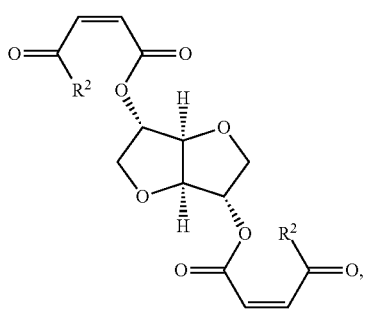
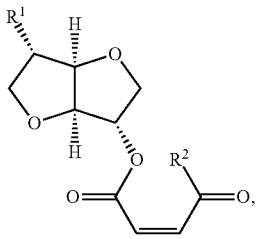
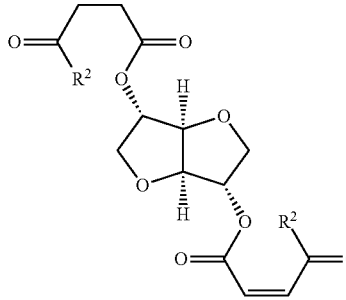

33
-continued
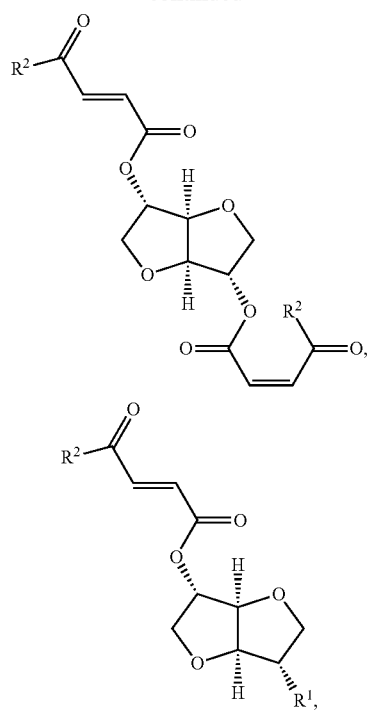
34
-continued
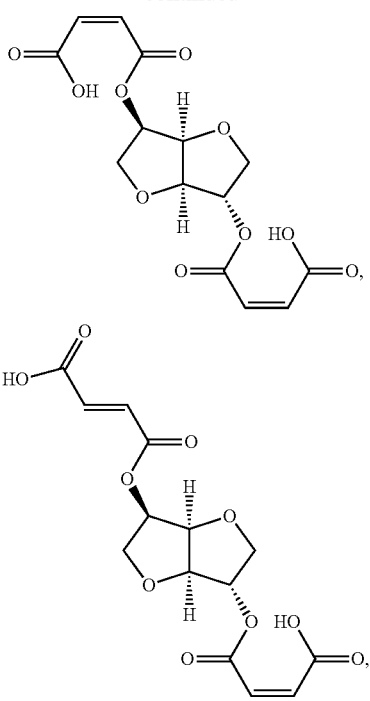

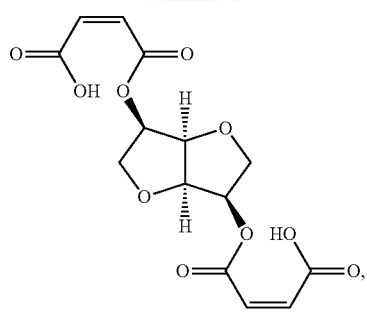

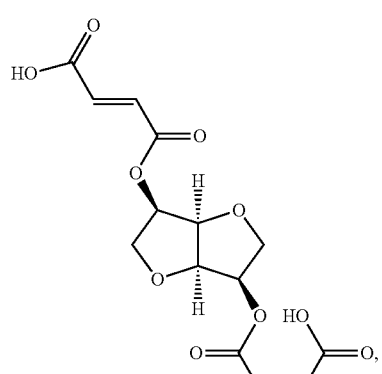

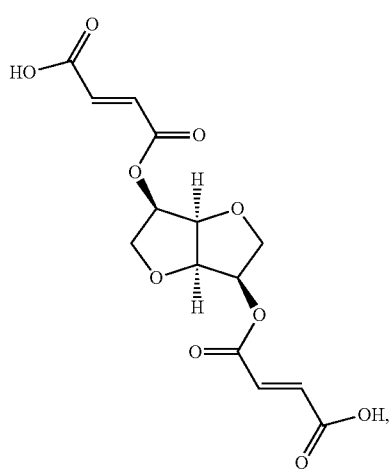

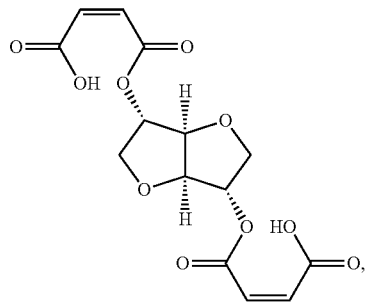

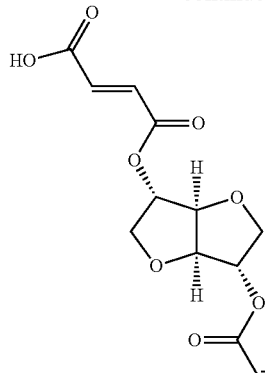

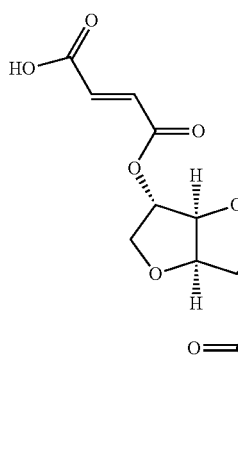

Polymer

In various embodiments, the present invention provides a polymer. The polymer can be derived in any suitable way. In some embodiments, the polymer is a reaction product of a tackifier compound, such as a cured tackifier compound having R' groups including at least one unsaturated aliphatic carbon-carbon bond. The reaction product can be a free-radical polymerization product. The polymer can have any suitable structure corresponding to a crosslinked product of any suitable curable tackifier compound described herein. In various embodiments, the polymer can include a repeating unit having the structure

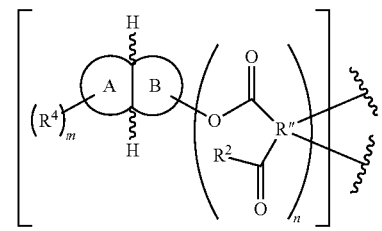

or a salt thereof. Fused rings A and B can be each independently chosen from (C5-$C_{10}$)cycloalkyl and ($C_2$-$C_{10}$)heterocyclyl. The variables m and n can be each independently 1-8. At each occurrence $R^4$ can be independently selected from —OH, —$OR^3$,

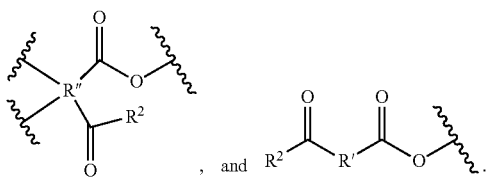, and 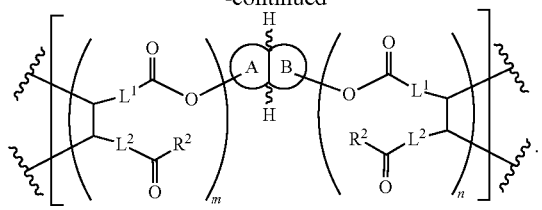

At each occurrence R' can be independently chosen from $(C_2\text{-}C_{10})$alkanylene, $(C_2\text{-}C_{10})$alkenylene, $(C_2\text{-}C_{10})$alkynylene, $C_5\text{-}C_{20}$(arylene), and $(C_1\text{-}C_{20})$heteroarylene, wherein R' can be unsubstituted or substituted with at least one J. At each occurrence R" can be independently a $(C_2\text{-}C_{10})$alkanylene bonded to at least one of a repeating unit and an end-blocking unit of the polymer at two locations, wherein R" is unsubstituted or substituted with at least one J. At each occurrence $R^2$ can be independently chosen from —OH, —$OR^3$, —$NH_2$, —$NHR^3$, and —$NR^3{}_2$. At each occurrence $R^3$ can be independently chosen from $(C_1\text{-}C_{10})$alkanyl, $(C_2\text{-}C_{10})$alkenyl, $(C_2\text{-}C_{10})$alkynyl, $C_5\text{-}C_{20}$(aryl), and $(C_1\text{-}C_{20})$heteroaryl, wherein $R^3$ is unsubstituted or substituted with at least one J. Fused rings A and B can be each independently unsubstituted or substituted with at least one of J, $(C_1\text{-}C_{10})$alkyl, $(C_2\text{-}C_{10})$alkenyl, $(C_2\text{-}C_{10})$alkynyl, $(C_1\text{-}C_{10})$haloalkyl, $(C_1\text{-}C_{10})$alkoxy, $(C_1\text{-}C_{10})$haloalkoxy, $(C_1\text{-}C_{10})$cycloalkyl$(C_0\text{-}C_{10})$alkyl, $(C_1\text{-}C_{10})$heterocyclyl$(C_0\text{-}C_{10})$alkyl, $(C_1\text{-}C_{10})$aryl$(C_0\text{-}C_{10})$alkyl, or $(C_1\text{-}C_{10})$heteroaryl$(C_0\text{-}C_{10})$alkyl; wherein each alkyl, alkenyl, alkynyl, haloalkyl, alkoxy, haloalkoxy, cycloalkyl, aryl, heterocyclyl, and heteroaryl can be independently unsubstituted or further substituted with at least one J. The variable J independently at each occurrence is chosen from F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, $OC(O)N(R)_2$, $C(S)N(R)_2$, $(CH_2)_{0\text{-}2}NHC(O)R$, $N(R)N(R)C(O)R$, $N(R)N(R)C(O)OR$, $N(R)N(R)C(O)N(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(C(O)R)C(O)R, N(OR)R, $C(=NH)N(R)_2$, C(O)N(OR)R, and C(=NOR)R, wherein R can be independently at each occurrence chosen from hydrogen, $(C_1\text{-}C_{10})$alkyl, $(C_1\text{-}C_{10})$cycloalkyl, $(C_1\text{-}C_{10})$cycloalkyl$(C_1\text{-}C_{10})$alkyl, $(C_1\text{-}C_{10})$aryl, $(C_1\text{-}C_{10})$aralkyl, $(C_1\text{-}C_{10})$heterocyclyl, $(C_1\text{-}C_{10})$heterocyclyl$(C_1\text{-}C_{10})$alkyl, $(C_1\text{-}C_{10})$heteroaryl, and $(C_1\text{-}C_{10})$heteroaryl$(C_1\text{-}C_{10})$alkyl, wherein each alkyl, cycloalkyl, cycloalkylalkyl, aryl, aralkyl, heterocyclyl, heterocyclylalkyl, heteroaryl, and heteroarylalkyl can be independently unsubstituted or substituted with 1-3 J. The polymer can have any suitable molecular weight. For example, the polymer can have a molecular weight of about 1,000 g/mol to about 20,000,000 g/mol, about 2,500 g/mol to about 10,000,000 g/mol, or about 5,000 g/mol to about 1,000,000 g/mol.

In some embodiments, the repeating unit can have a structure chosen from

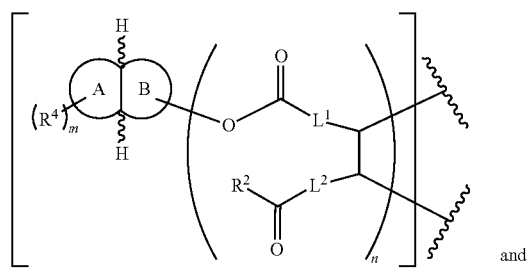 and

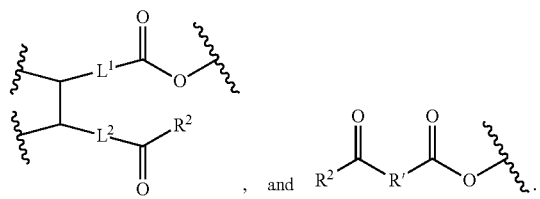

At each occurrence $L^1$ and $L^2$ can be independently chosen from a bond and $(C_1\text{-}C_{10})$alkyl. At each occurrence $R^4$ can be independently selected from —OH, —$OR^3$,

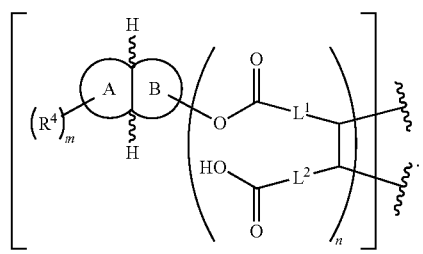, and 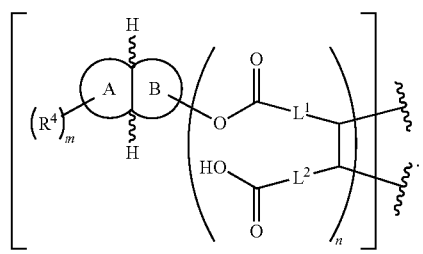

In some embodiments, the repeating unit can have the structure

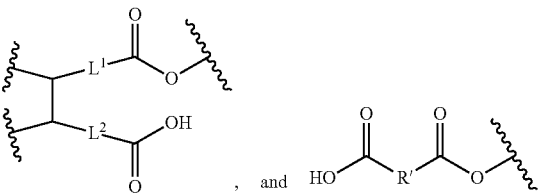

At each occurrence $L^1$ and $L^2$ can be independently chosen from a bond and $(C_1\text{-}C_{10})$alkyl. At each occurrence $R^4$ can be independently selected from —OH, —$OR^3$,

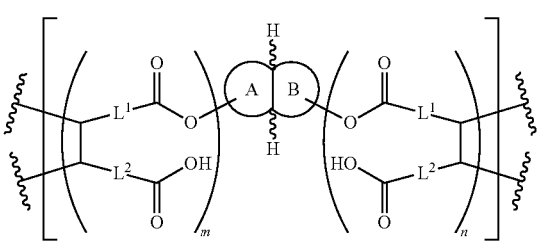

In some embodiments, the repeating unit can have the structure wherein at each occurrence $L^1$ and $L^2$ are independently chosen from a bond and $(C_1$-$C_{10})$alkyl.

In some embodiments, the repeating unit can have a structure chosen from

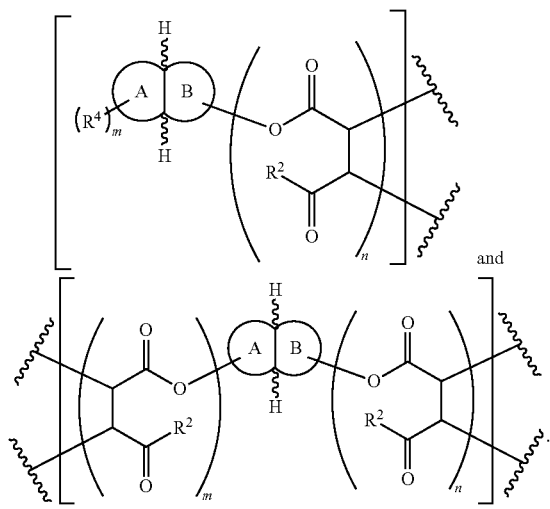

At each occurrence $R^4$ can be independently selected from —OH, —OR$^3$,

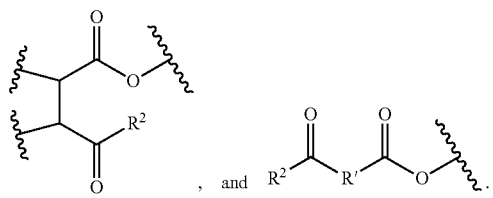

In some embodiments, the repeating unit can have the structure

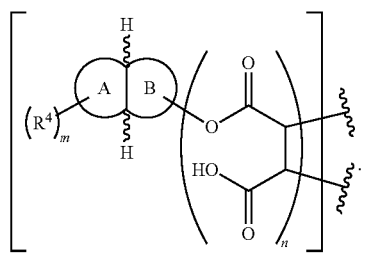

At each occurrence $R^4$ can be independently selected from —OH, —OR$^3$,

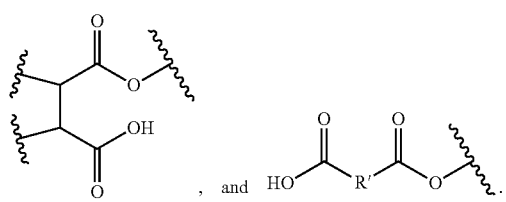

In some embodiments, the repeating unit can have the structure

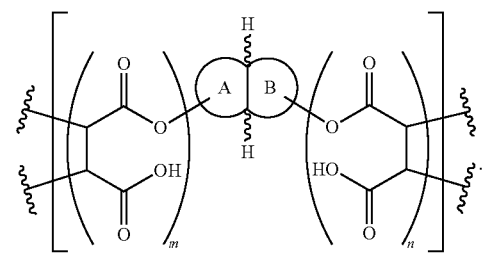

In various embodiments, rings A and B, variables m and n, and R″ (which corresponds to and can in some embodiments be derived from R′ in the tackifier compound) can be the same or similar. For example, rings A and B can form a ring system chosen from isosorbide, isomannide, and isoidide. The variable R″ can be an alkanylene bonded to at least one of a repeating unit and an end-blocking unit of the polymer at two locations and can be chosen from ethylene, propylene, butylene, or pentylene.

In some embodiments, the repeating unit can have a structure chosen from

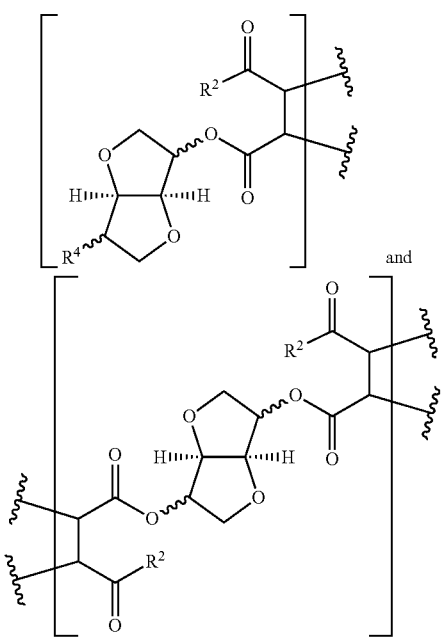

At each occurrence $R^4$ can be independently selected from —OH, —OR$^3$,

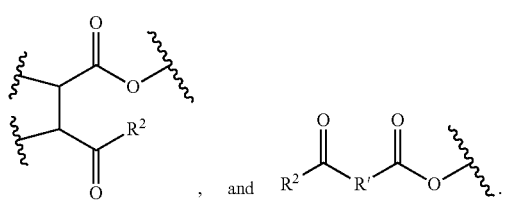

In some embodiments, the repeating unit does not include the structure

41

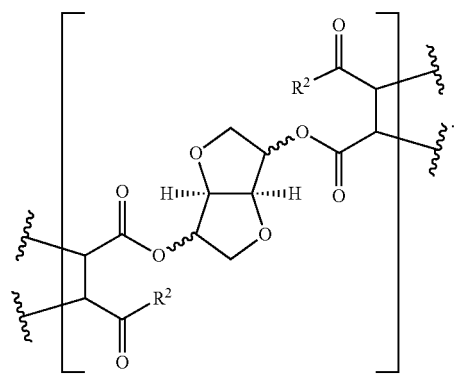

In some embodiments, the repeating unit does not include the structure

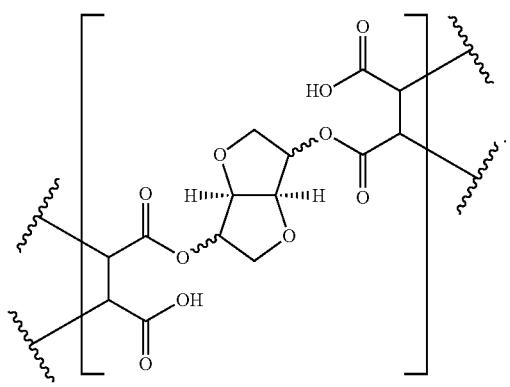

In some embodiments, the repeating unit does not include the structure

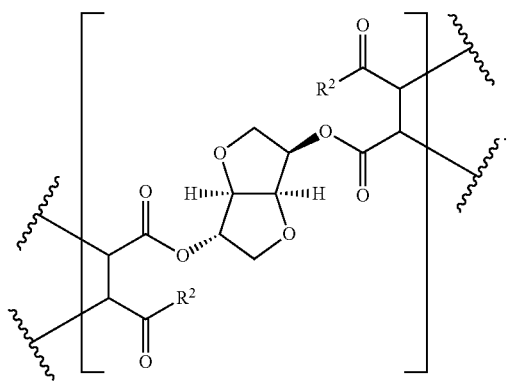

In some embodiments, the repeating unit does not include the structure

42

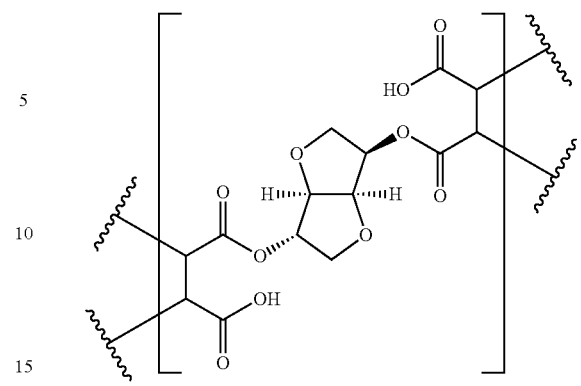

In some embodiments, the repeating unit does not include the structure

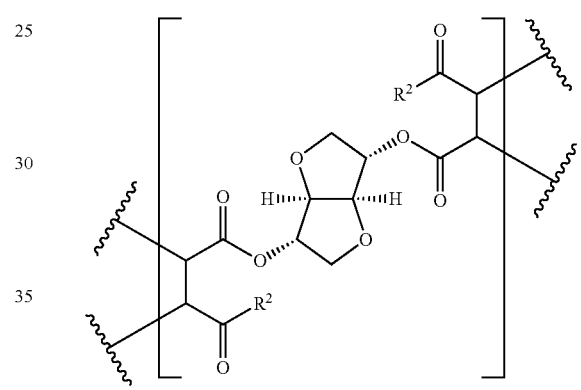

In some embodiments, the repeating unit does not include the structure

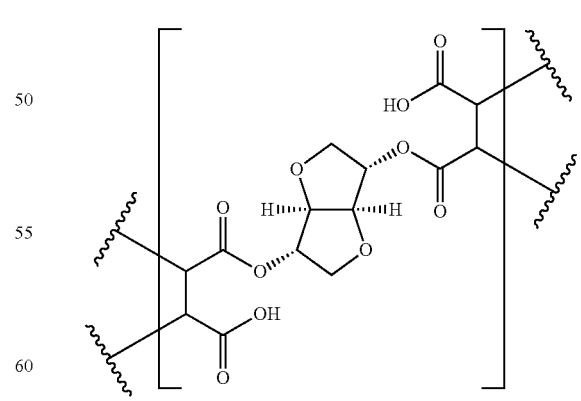

In some embodiments, the repeating unit does not include the structure

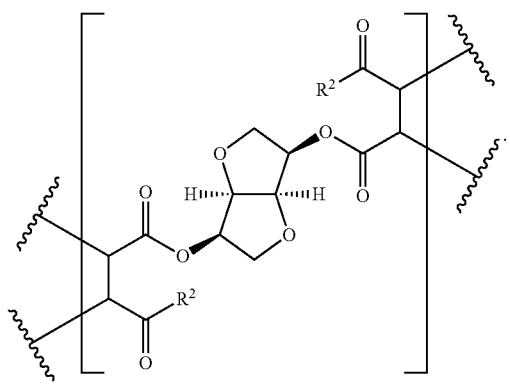
In some embodiments, the repeating unit does not include the structure
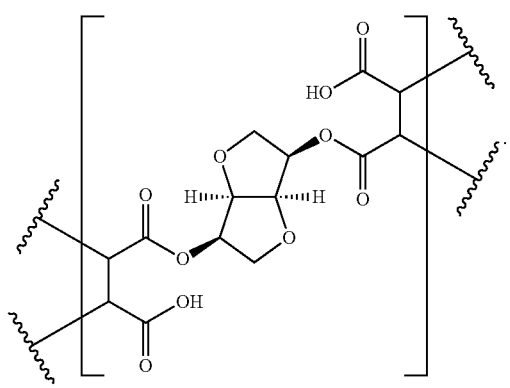
In some embodiments, the repeating unit can have the structure
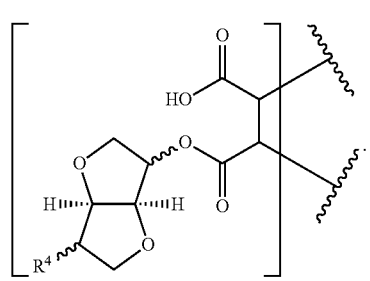
At each occurrence $R^4$ can be independently selected from —OH, —OR$^3$,
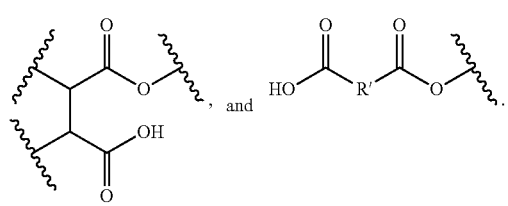
In some embodiments, the repeating unit can have the structure
In some embodiments, the repeating unit can have a structure chosen from
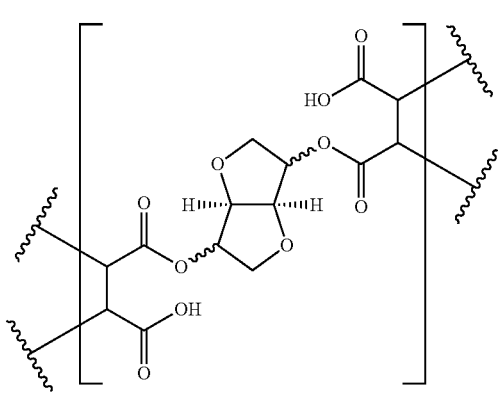
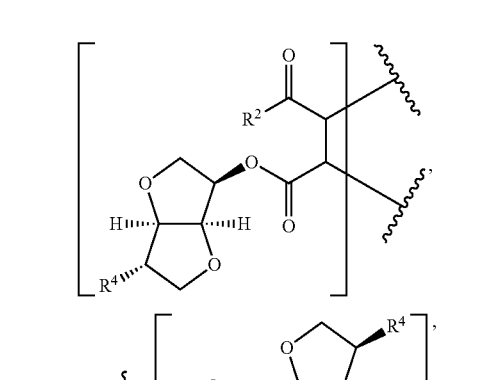
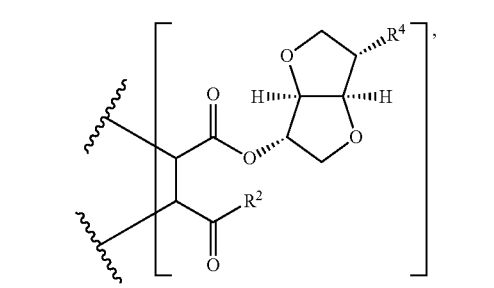

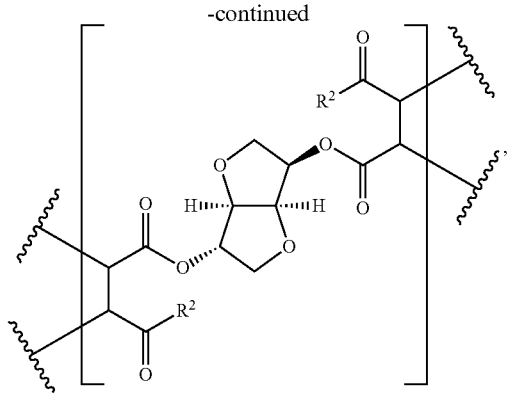
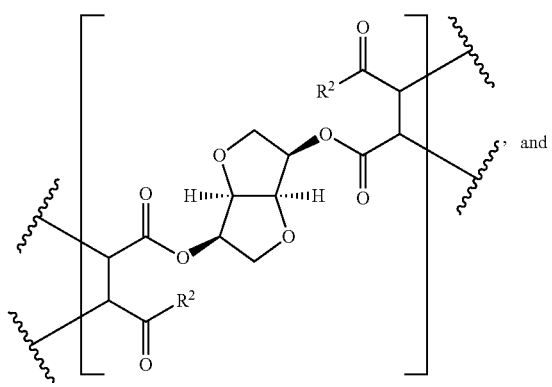, and
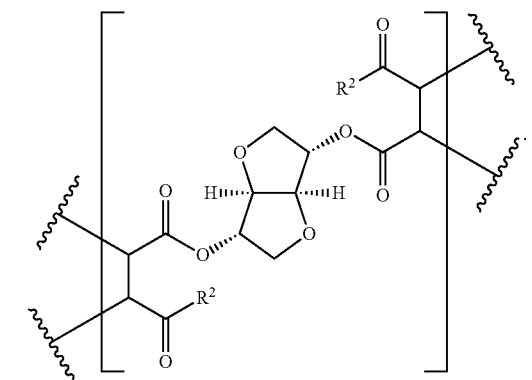.
At each occurrence $R^4$ can be independently selected from —OH, —OR$^3$,
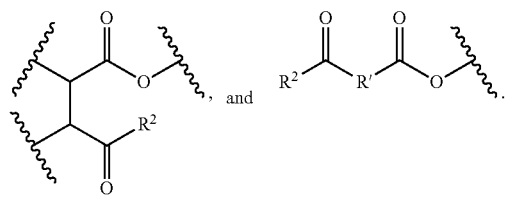
In some embodiments, the repeating unit can have a structure chosen from
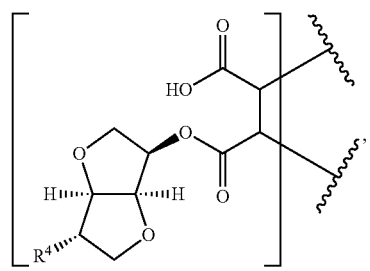,
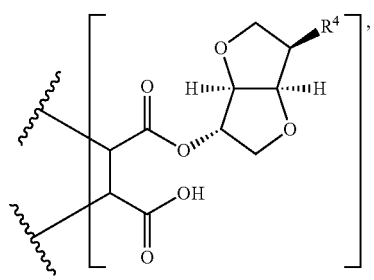,
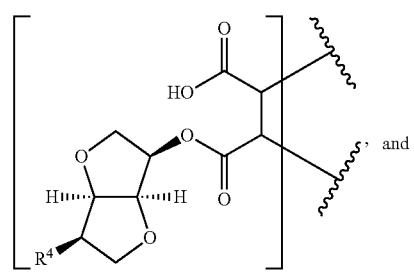, and
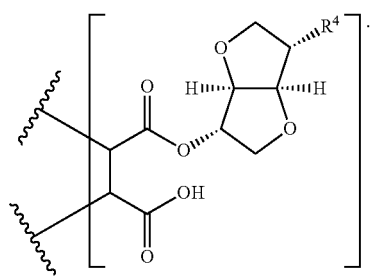.
At each occurrence $R^4$ can be independently selected from —OH, —OR$^3$,
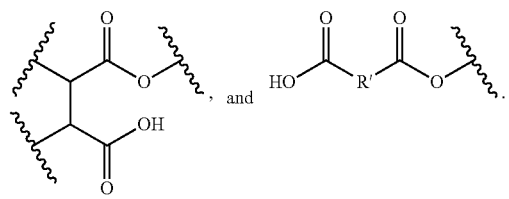
In some embodiments, the repeating unit can have a structure chosen from

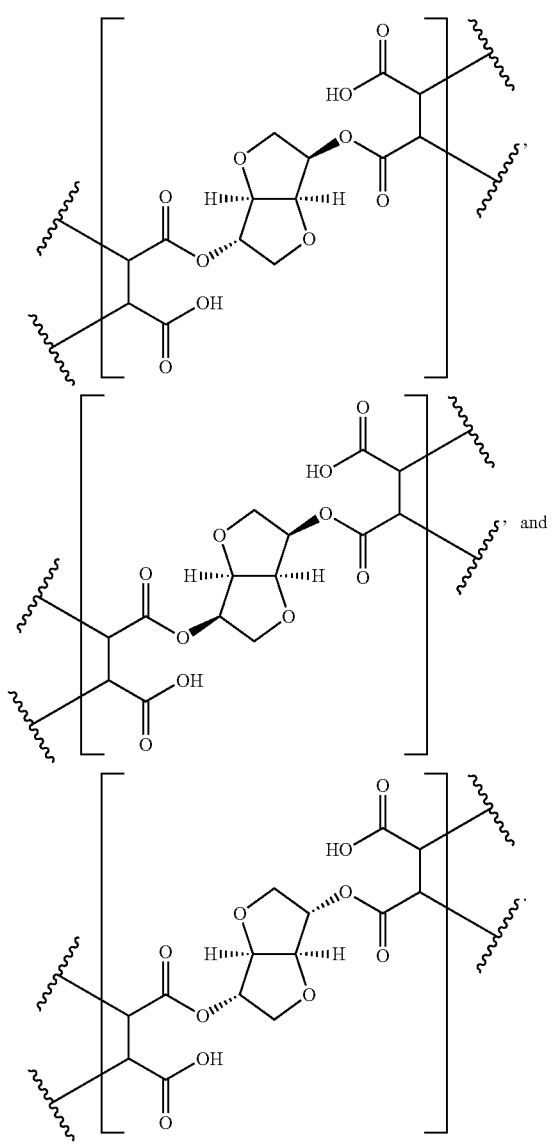

Method of Using Tackifier.

In various embodiments, the present invention provides a method of using a tackifier compound. The tackifier compound can be any suitable tackifier compound described herein, such as a compound having the structure

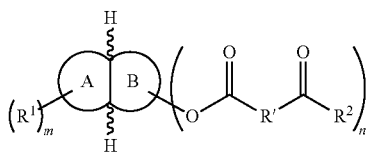

or the salt thereof. The tackifier compound can be used in any suitable way. The method can include contacting the tackifier compound to a first substrate. The tackifier compound can be contacted neat or in a composition. The contacting can be any suitable contacting, wherein the tackifier compound and the first substrate at least partially come into contact, such that the tackifier is bonded to the first substrate. The bonding can be any suitable bonding, for example, such that the tackifier compound has greater adhesion to the first substrate than a non-tackifier compound contacted under corresponding conditions. The first substrate can be any suitable material.

The method can further include contacting the tackifier compound to a second substrate. The contacting of the tackifier compound to the second substrate can be any suitable contacting, such that the tackifier compound and the second substrate at least partially come into contact, such that the tackifier compound is bonded to the second substrate and such that the first substrate is bonded to the second substrate at least partially via the tackifier compound. The bonding between the tackifier and the second substrate can be any suitable bonding, for example, such that the tackifier compound has greater adhesion to the second substrate than a non-tackifier compound contacted under corresponding conditions. The second substrate can be any suitable material. The bonding between the first substrate and the second substrate via the tackifier compound can be any suitable bonding, for example, such that the first substrate and the second substrate have greater adhesion than the first substrate and the second substrate would have under corresponding conditions without the presence of the tackifier compound therebetween.

In some embodiments, at least one R' is $C_1$-$C_{10}$ alkenylene or $C_1$-$C_{10}$ alkynylene, and the method further includes crosslinking the tackifier compound to provide a polymer. The polymer can be any suitable polymer described herein, such as a polymer including a repeating unit having the structure

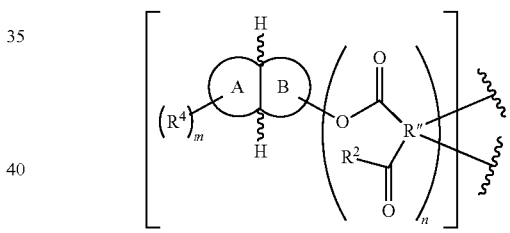

or a salt thereof. At each occurrence R''' can be independently a ($C_2$-$C_{10}$)alkanylene bonded to at least one of a repeating unit and an end-blocking unit of the polymer at two locations, wherein R''' is unsubstituted or substituted with at least one J. The crosslinking can include any suitable crosslinking, such as at least one of application of heat, application of radiation, addition of a chemical crosslinker, and initiation of a chemical crosslinker. In some embodiments, the chemical crosslinker includes a suitable free-radical initiator, such as any free-radical initiator described herein.

Method of Making Tackifier.

In various embodiments, the present invention provides a method of making a tackifier compound. The method includes contacting a compound having the structure

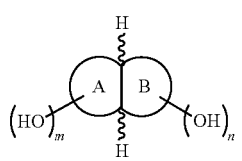

and an acid anhydride having the structure

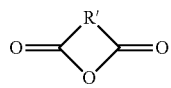

to provide a tackifier compound. The tackifier compound can be any tackifier compound described herein, such as a compound having the structure

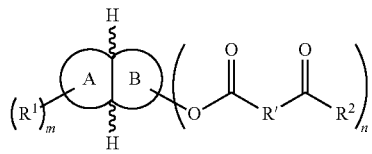

or a salt thereof. The fused rings A and B can each independently be chosen from ($C_5$-$C_{10}$)cycloalkyl and ($C_2$-$C_{10}$)heterocyclyl. The varaibles m and n can be each independently 1-8. At each occurrence $R^1$ can be independently selected from —OH, —$OR^3$, and

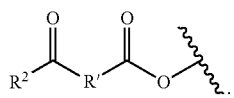

At each occurrence R' can be independently chosen from ($C_2$-$C_{10}$)alkanylene, ($C_2$-$C_{10}$)alkenylene, ($C_2$-$C_{10}$)alkynylene, $C_5$-$C_{20}$(arylene), and ($C_1$-$C_{20}$)heteroarylene, wherein R' can be unsubstituted or substituted with at least one J. At each occurrence $R^2$ can be independently chosen from —OH, —$OR^3$, —$NH_2$, —$NHR^3$, and —$NR^3{}_2$. At each occurrence $R^3$ can be independently chosen from ($C_1$-$C_{10}$)alkanyl, ($C_2$-$C_{10}$)alkenyl, ($C_2$-$C_{10}$)alkynyl, $C_5$-$C_{20}$(aryl), and ($C_1$-$C_{20}$)heteroaryl, wherein $R^3$ can be unsubstituted or substituted with at least one J. Fused rings A and B can be each independently unsubstituted or substituted with at least one of J, ($C_1$-$C_{10}$)alkyl, ($C_2$-$C_{10}$)alkenyl, ($C_2$-$C_{10}$)alkynyl, ($C_1$-$C_{10}$)haloalkyl, ($C_1$-$C_{10}$)alkoxy, ($C_1$-$C_{10}$)haloalkoxy, ($C_1$-$C_{10}$)cycloalkyl($C_0$-$C_{10}$)alkyl, ($C_1$-$C_{10}$)heterocyclyl($C_0$-$C_{10}$)alkyl, ($C_1$-$C_{10}$)aryl($C_0$-$C_{10}$)alkyl, or ($C_1$-$C_{10}$)heteroaryl ($C_0$-$C_{10}$)alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J. The variable J independently at each occurrence can be chosen from F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, C(O)$CH_2$C(O)R, C(S)R, C(O)OR, OC(O)R, OC(O)OR, C(O)$N(R)_2$, OC(O)$N(R)_2$, C(S)$N(R)_2$, $(CH_2)_{0-2}$NHC(O)R, N(R)N(R)C(O)R, N(R)N(R)C(O)OR, N(R)N(R)C(O)$N(R)_2$, $N(R)SO_2R$, $N(R)SO_2N(R)_2$, N(R)C(O)OR, N(R)C(O)R, N(R)C(S)R, N(R)C(O)$N(R)_2$, N(R)C(S)$N(R)_2$, N(C(O)R)C(O)R, N(OR)R, C(=NH)$N(R)_2$, C(O)N(OR)R, and C(=NOR)R, wherein R can be independently at each occurrence chosen from hydrogen, ($C_1$-$C_{10}$)alkyl, ($C_1$-$C_{10}$)cycloalkyl, ($C_1$-$C_{10}$)cycloalkyl($C_1$-$C_{10}$)alkyl, ($C_1$-$C_{10}$)aryl, ($C_1$-$C_{10}$)aralkyl, ($C_1$-$C_{10}$)heterocyclyl, ($C_1$-$C_{10}$)heterocyclyl($C_1$-$C_{10}$)alkyl, ($C_1$-$C_{10}$)heteroaryl, and ($C_1$-$C_{10}$)heteroaryl($C_1$-$C_{10}$)alkyl, wherein each alkyl, cycloalkyl, cycloalkylalkyl, aryl, aralkyl, heterocyclyl, heterocyclylalkyl, heteroaryl, and heteroarylalkyl can be independently unsubstituted or substituted with 1-3 J.

Rings A and B can form any suitable fused ring system. In some embodiments, m=n=1. In various embodiments, the polyol can be derived at least in part from renewable (e.g., non-petroleum) sources. Advantageously, by deriving the polyol from renewable sources, the resulting tackifier can be at least in part derived from renewable sources. For example, in some embodiments the polyol can be isosorbide:

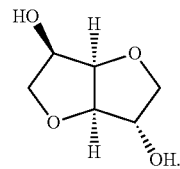

In some embodiments the polyol can be isomannide

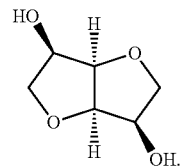

In some embodiments the polyol can be isoidide:

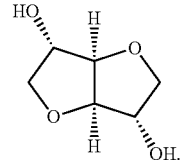

Isosorbide is a natural diol that can be derived from corn. Isosorbide, isomannide, and isoidide are three isomers of 1,4:3,6-dianhydrohexitol, and can be derived from, for example, D-glucose, D-mannose, and L-fructose, respectively. Isosorbide is the most widely available of the three isomers, as a by-product of the starch industry. Isosorbide, isomannide, and isoidide have characteristics including rigidity, thermal stability, chirality, and lack of toxicity, which make these polyols highly desirable for use in synthesizing environmentally benign and useful tackifiers therefrom.

The anhydride can be any suitable cyclic anhydride. For example, the anhydride can be chosen from succinic anhydride (e.g., R'=ethylene), glutaric anhydride (e.g., R'=propylene), and maleic anhydride (e.g., R'=ethenylene). In some examples, the anhydride can be derived at least in part from renewable sources. Advantageously, by deriving the anhydride from renewable sources, the resulting tackifier compound can be at least in part derived from renewable sources; if the polyol is also renewably derived, an even larger proportion of the tackifier compound is renewably derived. In various embodiments, the anhydride can be succinic anhydride, which can be derived from succinic acid, which can be isolated from, for example, the products of sugar fermentation.

The contacting of the fused bicyclic polyol and the acid anhydride can be performed under any suitable conditions. In some examples, the anhydride can be used in excess, such as about 1.2 equivalents or less, about 1.4 equivalents, 1.6, 1.8, 2.0, 2.2, 2.4, 2.6, 2.8, or about 3.0 or more equivalents, with about 1 equivalent of bicyclic polyol. The reaction can be performed neat, or with any suitable solvent and using any suitable concentration. The reaction can be stirred or unstirred. The reaction can be cooled, unheated, heated, or any combination thereof. The reaction can be cooled such that the temperature of the reaction does not exceed about −20° C. or less, about −10° C., −5° C., 0° C., 5° C., 10° C., or about 20° C. or more. The reaction can be unheated. The reaction can be heated to any suitable temperature, for example, about 80° C. or less, about 90° C., 100, 110, 120, 130, 140, 150, 180, 200, 220, 240, 260, 280, or about 300° C. or higher. In some examples, substantially all of the reaction vessel can be heated, for example, to avoid sublimation of the anhydride. The cooling, no heating, or heating can be performed for any suitable time, for example, about 10 min or less, about 30 min, 1 h, 2 h, 4 h, 6 h, 12 h, 18 h, 24 h, 1.5 d, 2 d, or about 3 d or more. The resulting polyacid tackifier can be carried forward to the next step crude or can be purified by any suitable technique. In some examples, the resulting crude polyacid is sufficiently pure such that little or no purification is required. For example, the crude tackifier can be ready for use as a tackifier compound as-is with no additional purification. In some embodiments, any solvent can be evaporated using standard techniques such as a rotating evaporator, and vacuum distillation or chromatography can be used to purify the polyacid.

In some embodiments, the contacting can further including contacting the reaction mixture including the cyclic anhydride and the polyol with a suitable amount of a catalyst. The catalyst can be any suitable catalyst. In some embodiments, the catalyst is an acid, such as a Bronsted acid (e g , mineral acids such as HCl, $H_2SO_4$, HF, HBr, or organic acids such as any $(C_1$-$C_{30})$alkanoic or alkenoic acid such as acetic or formic acid) or a Lewis acid (e.g., a metal halide, such as $AlCl_3$, $AlBr_3$, $BF_3$, $FeBr_3$, $FeCl_3$, $SnCl_4$, $SiF_4$, $TiCl_4$, and the like). In some embodiments, as compared to the method performed without the catalyst, the catalyst can reduce the reaction time needed to run the reaction to completion, reduce the reaction temperature needed to achieve a given reaction rate, and can allow production of the tackifier compound for a lower overall cost.

The method can further include synthesizing esterification or amidation products of the polyacid. The esterification products can be synthesized in any suitable fashion; for example, contacting with a base in the presence of an alkyl halide to generate the corresponding alkyl ester. Amidation products can be synthesized in any suitable fashion, for example, transformation of the polyacid to the acyl halide followed by amidation.

In some embodiments, the method of making the tackifier compound can be a method of making a polymer, and can further include crosslinking the tackifier compound. The crosslinking can be any suitable crosslinking, such as free-radical crosslinking. The tackifier compound can have R' that includes a crosslinkable group; for example, R' can be $(C_2$-$C_{10})$alkenylene or $(C_2$-$C_{10})$alkynylene. The polymer can be any suitable polymer described herein, such as a polymer including a repeating unit having the structure

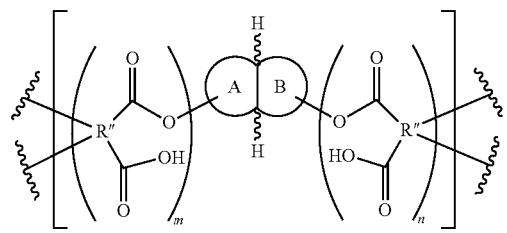

or a salt thereof.

The crosslinking can be performed in any suitable manner. For example, the crosslinking can include heating the tackifier compound to about 80° C. or less, about 90° C., 100, 110, 120, 130, 140, 150, 160, 170, 180, 190, 200, 210, 220, 230, 240, 250, 260, 280, or about 300° C. or higher. The heating can occur for any suitable duration such that crosslinking occurs, for example, about 10 min or less, about 30 min, 1 h, 2 h, 4 h, 6 h, 12 h, 18 h, 24 h, 1.5 d, 2 d, or about 3 d or more. In some embodiments, the crosslinking can occur at room temperature or near room temperature and can include mixing a crosslinker compound with the tackifier compound and allowing suitable time to pass for the crosslinking to occur, such as about 10 min or less, about 30 min, 1 h, 2 h, 4 h, 6 h, 12 h, 18 h, 24 h, 1.5 d, 2 d, or about 3 d or more. In some examples, the crosslinker compound can be a suitable free-radical initiator, such as any free-radical initiator described herein. A method of crosslinking including heating can optionally include the presence of one or more suitable crosslinker compounds. In some embodiments, the crosslinking can include exposing the tackifier compound to a suitable form of radiation of a suitable intensity and for a suitable duration.

System including tackifier or cured tackifier.

In various embodiments, the present invention provides a system including a tackifier compound. The tackifier compound can be any suitable tackifier compound described herein, such as a tackifier compound having the structural formula

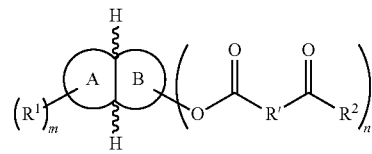

or a salt thereof. The tackifier compound can be neat or in a composition. In the system, the tackifier compound is bonded to the first substrate. The first substrate can be any suitable material. The bonding can be any suitable bonding, for example, such that the tackifier compound has greater adhesion to the first substrate than a non-tackifier compound (e.g., water) contacting the first substrate under corresponding conditions. In some embodiments, the system further includes a second substrate. The tackifier compound can be bonded to the first and second substrate such as to bond the first substrate to the second substrate at least partially via the tackifier compound. The second substrate can be any suitable material. The bonding between the second substrate and the tackifier compound can be any suitable bonding, for example, such that the tackifier compound and the second substrate have greater adhesion than a non-tackifier compound contacting the second substrate under corresponding conditions. The bonding between the first substrate and the second substrate can be any suitable bonding, for example, such that the first substrate and the second substrate have greater adhesion than the first substrate and the second substrate would have under corresponding conditions without the presence of the tackifier compound therebetween.

In various embodiments, the present invention provides a system including a polymer. The polymer can be any suitable polymer described herein, such as a polymer including a repeating unit having the structure

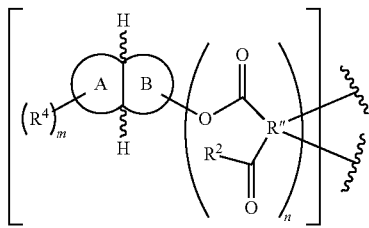

or a salt thereof. The polymer can be neat or in a composition. In the system, the polymer is bonded to the first substrate. The first substrate can be any suitable material. The bonding can be any suitable bonding, for example, such that the polymer has greater adhesion to the first substrate than a non-tackifier compound contacting the first substrate under corresponding conditions. In some embodiments, the system further includes a second substrate. The polymer can be bonded to the first and second substrate such as to bond the first substrate to the second substrate at least partially via the polymer. The second substrate can be any suitable material. The bonding between the second substrate and the polymer can be any suitable bonding, for example, such that the polymer and the second substrate have greater adhesion than a non-tackifier compound contacting the second substrate under corresponding conditions. The bonding between the first substrate and the second substrate can be any suitable bonding, for example, such that the first substrate and the second substrate have greater adhesion than the first substrate and the second substrate would have under corresponding conditions without the presence of the polymer compound therebetween.

EXAMPLES

The present invention can be better understood by reference to the following Examples which are offered by way of illustration. The present invention is not limited to the Examples given herein.

Example 1a

Synthesis of tackifiers 3a-3c from Isosorbide 1

Scheme 1. Synthesis of diacids 3a-3c.

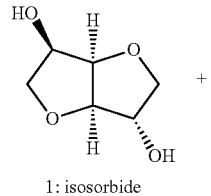

1: isosorbide

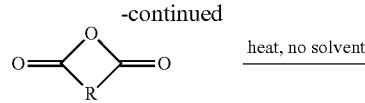

2a: succinic anhydride
(R = —CH$_2$—CH$_2$—)
2b: glutaric anhydride
(R = —CH$_2$—CH$_2$—CH$_2$—)
2c: maleic anhydride
(R = —CH═CH—)

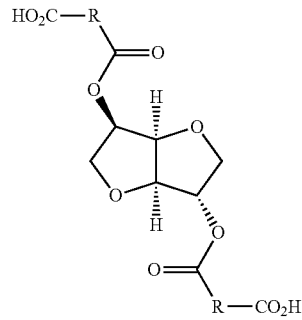

3a: R = —CH$_2$—CH$_2$—
3b: R = —CH$_2$—CH$_2$—CH$_2$—
3c: R = —CH═CH—

A mixture of isosorbide (1, 7.31 g, 50 mmol) and succinic anhydride (2a, 11.51 g, 115 mmol, 2.3 equiv) was heated at 120° C. for 24 hr to give diacid 3a as a viscous orange oil. To avoid sublimation of succinic anhydride 2a, the entire reaction vessel was heated. The chemical yield was estimated by $^1$H NMR analysis to be approximately 100%. Sublimation of succinic anhydride (2a) from the crude material afforded a sample of diacid 3a for analysis. 3a: R$_f$=0.43 (silica gel, EtOAc); $[\alpha]_D^{23}$=+90.9° (c=1.00, CHCl$_3$); IR (thin film): $\nu_{max}$=1739, 1716 cm$^{-1}$; $^1$H NMR (400 MHz, CDCl$_3$): δ=10.51 (br, 2H), 5.21 (s, 1H), 5.17 (q, J=5.4 Hz, 1H), 4.83 (t, J=5.1 Hz, 1H), 4.47 (d, J=4.7 Hz, 1H), 3.94 (m, 3H), 3.81 (dd, J=10.0, 5.1 Hz, 1H), 2.69 (s, 4H), 2.65 (m, 4H); $^{13}$C NMR (100 MHz, CDCl$_3$): δ=178.01, 177.95, 171.71, 171.33, 85.88, 80.87, 78.37, 74.42, 73.33, 70.54, 29.04, 29.01, 28.98, 28.76 ppm; HRMS (ESI-QTOF) calcd for C$_{14}$H$_{17}$O$_{10}$$^+$ [M−H$^+$]: 345.0822, found: 345.0827.

A mixture of isosorbide (1, 7.31 g, 50 mmol) and glutaric anhydride (2b, 14.26 g, 125 mmol, 2.5 equiv) was refluxed at 170° C. for 24 hr to give diacid 3b as a black viscous liquid. The chemical yield was estimated by $^1$H NMR analysis to be approximately 92%. Evaporation of glutaric anhydride (2b) from the crude material followed by chromatography in 0.5% methanol/99.5% ethyl acetate afforded a sample of diacid as a clear transparent oil 3b for analysis. 3b: R$_f$=0.35 (silica gel, EtOAc); $[\alpha]_D^{23}$=+112.74° (c=1.00, CHCl$_3$); IR (thin film): $\nu_{max}$=3514, 1736 cm$^{-1}$; $^1$H NMR (600 MHz, CDCl$_3$): δ=5.19 (s, 1H), 5.16 (q, J=5.5 Hz, 1H), 4.84 (t, J=4.7 Hz, 1H), 4.47 (d, J=4.3 Hz, 1H), 3.96 (d, J=3.5 Hz, 2H), 3.93 (dd, J=10.1, 6.1 Hz, 1H), 3.81 (dd, J=10.0, 5.1 Hz, 1H), 2.47 (t, J=6.7 Hz, 4H) 2.45-2.38 (m, 4H), 2.01-1.91 (m, 4H) ppm; $^{13}$C NMR (151 MHz, CDCl$_3$): δ=178.65, 178.50, 172.40, 172.07, 85.99, 80.79, 78.19, 74.14, 73.42, 70.55, 33.21, 32.99, 32.94, 32.85, 19.92, 19.81 ppm; HRMS (ESI-QTOF) calcd for C$_{16}$H$_{22}$O$_{10}$Na$^+$[M+Na$^+$]: 397.1105, found: 397.1109; DSC (He, 10° C. min$^{-1}$): T$_g$=−26° C., T$_m$=31° C.

A mixture of isosorbide (1, 4.38 g, 30 mmol) and maleic anhydride (2c, 7.35 g, 75 mmol, 2.5 equiv) was heated at 170° C. for 72 hr to give diacid 3c as a yellow solid. To avoid sublimation of maleic anhydride 2c, the entire reaction vessel was heated. The chemical yield was estimated by $^1$H NMR analysis to be approximately 73%. 3c: $R_f$=0.27 (silica gel, 30% MeOH/70% EtOAc); IR (thin film): $\nu_{max}$=3527, 1644 cm$^{-1}$; $^1$H NMR (400 MHz, DMSO-d$^6$): δ=13.24 (br, 2H), 6.87-6.64 (m, 4H), 5.24 (m, 1H), 5.19 (m, 1H), 4.87 (m, 1H), 4.51 (m, 1H), 3.99-3.92 (m, 1H), 3.92-3.81 (m, 3H) ppm; HRMS (ESI-QTOF) calcd for $C_{14}H_{13}O_{10}{}^-$[M-H$^+$]: 341.0514, found: 341.0524; DSC (He, 10° C. min$^{-1}$): $T_g$=20° C., $T_m$=158° C.

Example 1b

Synthesis of Tackifiers 5a-5c from Isomannide 4 (Hypothetical for 5c Only)

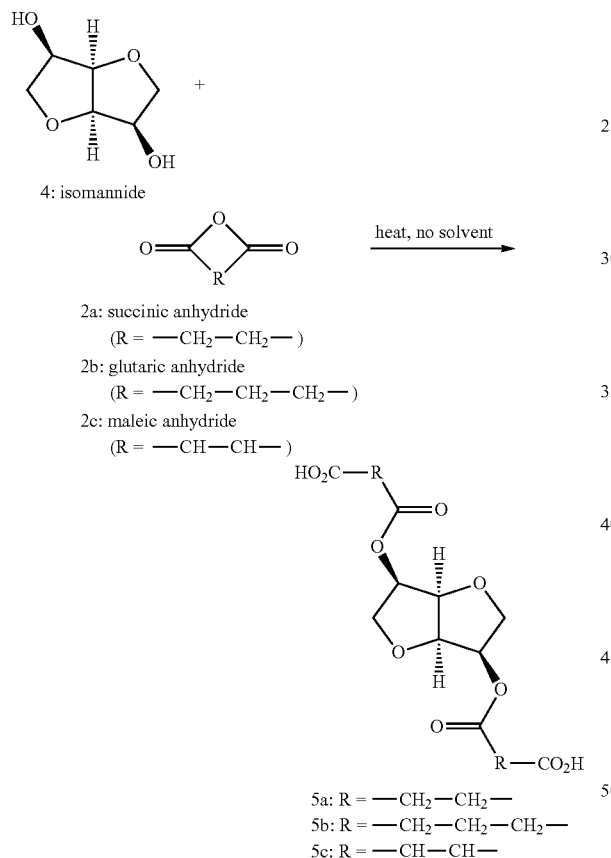

Scheme 2. Synthesis of diacids 5a-5c.

A mixture of isomannide (4, 7.31 g, 50 mmol) and succinic anhydride (2a, 11.51 g, 115 mmol, 2.3 equiv) was heated at 120° C. for 24 h to give diacid 5a as a viscous orange oil. The entire reaction vessel was heated to minimize evaporative loss of succinic anhydride (2a). Vacuum sublimation of succinic anhydride (2a) from the crude material gave a sample of diacid 5a for analysis. 5a: $R_f$=0.38 (silica gel, EtOAc); $[α]_D{}^{23}$=+116.9 (c=1.00, CHCl$_3$); IR (thin film): $\nu_{max}$=1741, 1717 cm$^{-1}$; $^1$H NMR (400 MHz, CDCl$_3$): δ=8.29 (br, 2H), 5.10 (d, J =5.8 Hz, 2H), 4.68 (dd, J=9.3, 3.8 Hz, 2H), 4.01 (dd, J=9.6, 6.1 Hz, 2H), 3.79 (dd, J=9.6, 6.3 Hz, 2H), 2.77-2.70 (m, 4H), 2.70-2.65 (m, 4H) ppm; $^{13}$C NMR (100 MHz, CDCl$_3$): δ=178.20, 171.37, 80.58, 73.98, 70.72, 29.40, 29.25 ppm; HRMS (ESI-QTOF) calcd for $C_{14}H_{17}O_{10}{}^-$[M-H$^+$]: 345.0822, found: 345.0821; DSC (He, 10° C. min$^1$): $T_g$=-2° C.

A mixture of isomannide (4, 7.31 g, 50 mmol) and glutaric anhydride (2b, 14.26 g, 125 mmol, 2.5 equiv) was refluxed at 170° C. for 24 hr to give diacid 5b as a black viscous liquid. The chemical yield was estimated by $^1$H NMR analysis to be approximately 91%. Evaporation of glutaric anhydride (2b) from the crude material followed by chromatography in 0.5% methanol/99.5% ethyl acetate afforded a sample of diacid 5b as a clear transparent oil for analysis. 5b: $R_f$=0.35 (silica gel, EtOAc); $[α]_D{}^{23}$=+87.28°; (c=1.00, CHCl$_3$); IR (thin film): $\nu_{max}$=3422, 1736, 1709 cm$^{-1}$; $^1$H NMR (600 MHz, CDCl$_3$): δ=5.09 (q, J=5.5 Hz, 2H), 4.70 (d, J=4.2 Hz, 2H), 4.02 (dd, J=9.4, 6.3 Hz, 2H), 3.81 (dd, J=9.4, 6.7 Hz, 2H), 2.49 (dt, J=7.3, 3.6, Hz, 4H), 2.46 (t, J=7.1 Hz, 4H), 1.99 (p, J=7.2 Hz, 4H) ppm; $^{13}$C NMR (151 MHz, CDCl$_3$): δ=178.97, 172.42, 80.50, 73.77, 70.69, 32.96, 32.90, 19.93 ppm; $C_{16}H_{22}O_{10}Na^+$ [M+Na$^+$]: 397.1105, found: 397.1112; DSC (He, 10° C. min$^{-1}$): $T_g$=-26° C., $T_m$=33° C.

The procedure of Example 1a is followed using isomannide in place of isosorbide to give diacid 5c at about 100% yield at high purity.

Example 1c

Synthesis of Tackifiers 7a-7c from Isoidide 6 (Hypothetical)

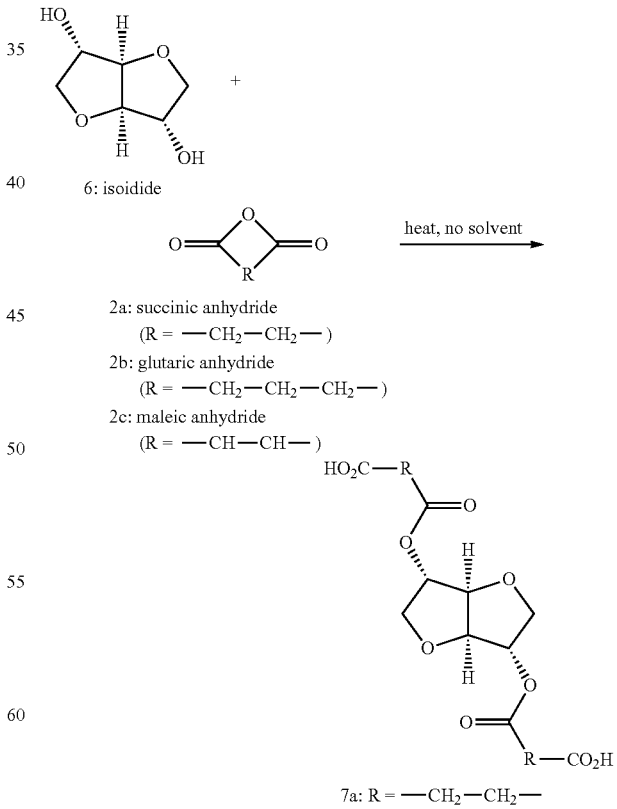

Scheme 3. Synthesis of diacids 7a-7c.

The procedure of Example 1a is followed using isoidide in place of isosorbide to give diacids 7a-7c at about 100% yield at high purity.

Example 1d

Synthesis of Tackifier 8 from Diacid 3a

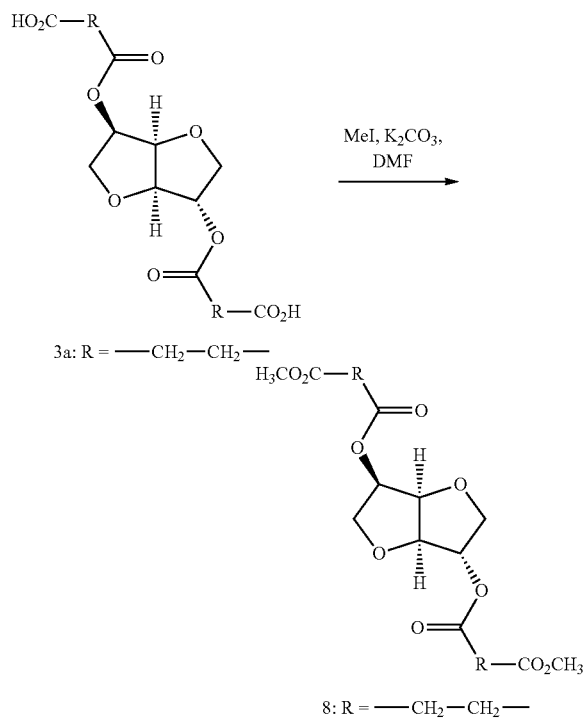

Scheme 4. Synthesis of diester 8.

A mixture of diacid 3a (7.27 g, 21 mmol), methyl iodide (4 mL, 63 mmol, 3 eq.), and potassium carbonate (8.71 g, 63 mmol, 3 eq.) were dissolved in N,N-dimethylformamide (42 mL), and heating to 35° C. for 24 hr to give crude dimethyl ester 8. The reaction was diluted with 80 mL of water and extracted with 2×50 mL EtOAc followed by washing with 3×100 mL $H_2O$ and 1×100 mL brine and dried over $MgSO_4$. Purification via chromatography in 60% ethyl acetate/40% hexanes resulted in pure dimethyl ester as a clear viscous oil in 40% yield. 8: $R_f$=0.36 (silica gel, 60% EtOAc/40% Hexanes); $[\alpha]_D^{23}$=+28.69° (c=1.00, $CHCl_3$); IR (thin film): $\nu$=1739 $cm^{-1}$; $^1$H NMR (600 MHz, $CDCl_3$): $\delta$=5.20 (s, 1H), 5.16 (q, J=5.6 Hz, 1H), 4.81 (t, J=5.0 Hz, 1H), 4.47 (d, J=4.7 Hz, 1H), 3.96 (d, J=2.3 Hz, 2H), 3.92 (dd, J=9.9, 6.0 Hz, 1H), 3.80 (dd, J=9.9, 5.2 Hz, 1H), 3.69 (s, 3H), 3.68 (s, 3H) 2.71-2.59 (m, 8H) ppm; $^{13}$C NMR (151 MHz, $CDCl_3$): $\delta$=172.66, 172.63, 171.79, 171.49, 85.97, 80.85, 78.37, 74.32, 73.40, 70.50, 52.04, 52.02, 29.18, 28.95, 28.93, 28.88 ppm; HRMS (ESI-QTOF) calcd for $C_{16}H_{23}O_{10}^+$ [M+H$^+$]: 375.1286, found: 375.1292; DSC (He, 10° C. $min^{-1}$): $T_g$=-34° C., $T_m$=29° C.

Example 2

Properties of the Tackifiers of Example 1a

Although none of the precursors 1 and 2a-2c had significant tackiness, the resultant diacids (3a-3c) were highly tacky (see Table 1). Altering the identity of the acid anhydride altered tackifier properties. For example, succinic anhydride-derived tackifier 3a was substantially water-soluble and could be cleanly washed away by water, yet it remained active as a tackifier under damp conditions. In contrast, glutaric anhydride-derived tackifier 3b, differing from 3a in the addition of a $CH_2$ moiety to the cyclic anhydride component, was substantially water-insoluble. Changes to the anhydride component also resulted in differences in the glass transition temperature ($T_g$) and in the temperature range over which the maximum degree of tackiness was observed.

Tack was measured by modifications to the ASTM 02979 standard. On an Instron® load frame, the tackifier to be tested was applied to a glass slide at a thickness of 0.1 mm The slide was then clamped to a flat surface and, perpendicularly, a type 304 stainless steel probe measuring 5 mm in diameter, with a 90° polished tip was place above the slide. The probe was then lowered at a rate of 0.5 mm $sec^{-1}$ and contacted the surface at an average force of 1.5 N. The probe was then held on the surface for 1.0 sec and then raised at a rate of 0.5 mm $sec^{-1}$. Tack was measured as the maximum force required to remove the probe from the surface of the tackifier. $T_g$ was measured by DSC.

TABLE 1

Properties of tackifiers at selected temperatures from −50° C. to 80° C.

| | Water soluble? | $T_g$ (° C.) | $T_m$ (° C.) | Maximum tack (kPa) |
|---|---|---|---|---|
| 3a | Y | −2 | | 168 at 25° C. |
| 3b | N | −24 | 31 | 112 at 25° C. |
| 3c | N | 16 | 158 | 130 at 60° C. |
| 5a | Y | −2 | | 121 at 25° C. |
| 5b | N | −26 | 33 | 107 at 60° C. |
| 8 | Y | −34 | 29 | 285 at −20° C. |

Example 3

Curing of Tackifier 3c

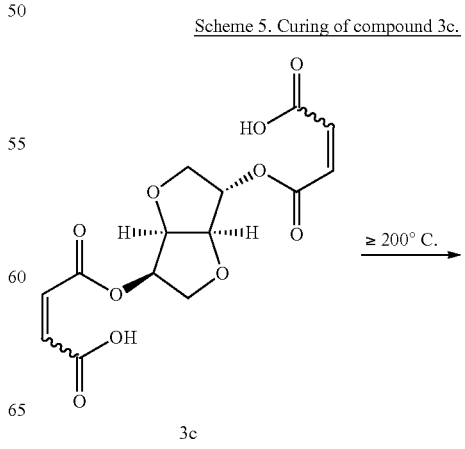

Scheme 5. Curing of compound 3c.

-continued

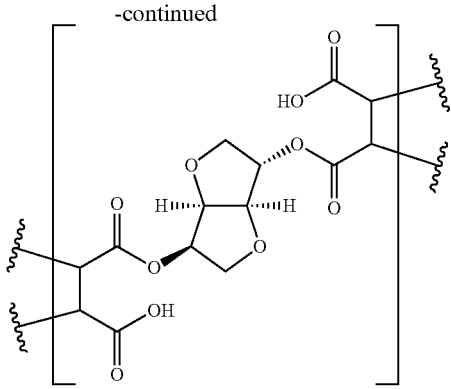

The alkene in maleic anhydride-derived tackifier 3c in Example 1a was subjected to a curing process to generate a cross-linked polymer. When heated to about 200° C., a closed-ended borosilicate glass tube that could be readily removed from the substance prior to curing was stuck in place after the curing; rather than come free, the glass tube sheared at the surface of the cured material. Thus, the material cured to yield a hard substance that held in place a piece of glass with substantial strength and permanence.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of this invention as defined by the appended claims.

Additional Embodiments.

The present invention provides for the following exemplary embodiments, the numbering of which is not to be construed as designating levels of importance:

Embodiment 1 provides a tackifier compound having the structural formula

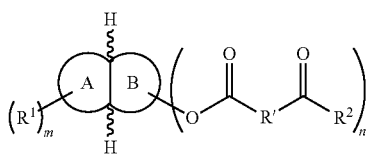

or a salt thereof;

wherein fused rings A and B are each independently chosen from $(C_5-C_{10})$cycloalkyl and $(C_2-C_{10})$heterocyclyl;

m and n are each independently 1-8;

at each occurrence $R^1$ is independently selected from —OH, —$OR^3$, and

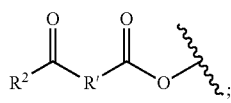

at each occurrence R' is independently chosen from $(C_2-C_{10})$alkanylene, $(C_2-C_{10})$alkenylene, $(C_2-C_{10})$alkynylene, $C_5-C_{20}$(arylene), and $(C_1-C_{20})$heteroarylene, wherein R' is unsubstituted or substituted with at least one J;

at each occurrence $R^2$ is independently chosen from —OH, —$OR^3$, —$NH_2$, —$NHR^3$, and —$NR^3{}_2$;

at each occurrence $R^3$ is independently chosen from $(C_1-C_{10})$alkanyl, $(C_2-C_{10})$alkenyl, $(C_2-C_{10})$alkynyl, $C_5-C_{20}$(aryl), and $(C_1-C_{20})$heteroaryl, wherein $R^3$ is unsubstituted or substituted with at least one J;

fused rings A and B are each independently unsubstituted or substituted with at least one of J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0-C_{10})$alkyl, or $(C_1-C_{10})$heteroaryl$(C_0-C_{10})$alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J; and wherein J independently at each occurrence is chosen from F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, C(O)$CH_2$C(O)R, C(S)R, C(O)OR, OC(O)R, OC(O)OR, C(O)N(R)$_2$, OC(O)N(R)$_2$, C(S)N(R)$_2$, $(CH_2)_{0-2}$NHC(O)R, N(R)N(R)C(O)R, N(R)N(R)C(O)OR, N(R)N(R)C(O)N(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(C(O)R)C(O)R, N(OR)R, C(=NH)N(R)$_2$, C(O)N(OR)R, and C(=NOR)R, wherein R is independently at each occurrence chosen from hydrogen, $(C_1-C_{10})$alkyl, $(C_1-C_{10})$cycloalkyl, $(C_1-C_{10})$cycloalkyl$(C_1-C_{10})$alkyl, $(C_1-C_{10})$aryl, $(C_1-C_{10})$aralkyl, $(C_1-C_{10})$heterocyclyl, $(C_1-C_{10})$heterocyclyl$(C_1-C_{10})$alkyl, $(C_1-C_{10})$heteroaryl, and $(C_1-C_{10})$heteroaryl$(C_1-C_{10})$alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

Embodiment 2 provides the tackifier compound of Embodiment 1, wherein the compound is not a salt.

Embodiment 3 provides the tackifier compound of any one of Embodiments 1-2, wherein the compound is substantially water soluble.

Embodiment 4 provides the tackifier compound of any one of Embodiments 1-3, wherein the compound is partially soluble in water, such that about 0.000,1 g to about 0.6 g dissolve in about 1 mL of water at about 25° C.

Embodiment 5 provides the tackifier compound of any one of Embodiments 1-4, wherein the compound is partially soluble in water, such that about 0.01 g to about 0.3 g dissolve in about 1 mL of water at about 25° C.

Embodiment 6 provides the tackifier compound of any one of Embodiments 1-5, wherein the compound is substantially insoluble in water.

Embodiment 7 provides the tackifier compound of any one of Embodiments 1-6, wherein the compound has a glass transition temperature of about −90° C. to about 60° C.

Embodiment 8 provides the tackifier compound of any one of Embodiments 1-7, wherein the compound has a glass transition temperature of about −60° C. to about 40° C.

Embodiment 9 provides the tackifier compound of any one of Embodiments 1-8, wherein the compound has a glass transition temperature of about −35° C. to about 20° C.

Embodiment 10 provides the tackifier compound of any one of Embodiments 1-9, wherein the compound has a tack of about 50 kPa to about 400 kPa at one or more temperatures that are about −40° C. to about 80° C.

Embodiment 11 provides the tackifier compound of any one of Embodiments 1-10, wherein the compound has a tack of about 50 kPa to about 400 kPa at one or more temperatures that are about 5° C. to about 45° C.

Embodiment 12 provides the tackifier compound of any one of Embodiments 1-11, wherein the compound has a tack of about 50 kPa to about 400 kPa at one or more temperatures that are about 40° C. to about 80° C.

Embodiment 13 provides the tackifier compound of any one of Embodiments 1-12, wherein the compound has a tack of about 75 kPa to about 250 kPa at one or more temperatures that are about 15° C. to about 35° C.

Embodiment 14 provides the tackifier compound of any one of Embodiments 1-13, wherein the compound has a tack of about 75 kPa to about 250 kPa at one or more temperatures that are about 50° C. to about 70° C.

Embodiment 15 provides the tackifier compound of any one of Embodiments 1-14, wherein the compound has a tack of about 100 kPa to about 180 kPa at one or more temperatures that are about 15° C. to about 35° C.

Embodiment 16 provides the tackifier compound of any one of Embodiments 1-15, wherein the compound has a tack of about 120 kPa to about 140 kPa at one or more temperatures that are about 50° C. to about 70° C.

Embodiment 17 provides the tackifier compound of any one of Embodiments 1-16, wherein the compound has a tack of about 200 kPa to about 400 kPa at one or more temperatures that are about −40° C. to about 0° C.

Embodiment 18 provides the tackifier compound of any one of Embodiments 1-17, wherein one —C(O)OH moiety is in the form of a salt.

Embodiment 19 provides the tackifier compound of any one of Embodiments 1-18, wherein two —C(O)OH moieties are in the form of a salt.

Embodiment 20 provides the tackifier compound of any one of Embodiments 1-19, wherein the salt comprises at least one counterion chosen from $Na^+$, $K^+$, $Ag_+$, $NH_4^+$, $Al^{3+}$, $Ca^{2+}$, $Cu^{2+}$, $Fe^{2+}$, $Fe^{3+}$, and $Mg^{2+}$.

Embodiment 21 provides the tackifier compound of any one of Embodiments 1-20, wherein $R^1$ is —OH.

Embodiment 22 provides the tackifier compound of any one of Embodiments 1-21, wherein $R^1$ is

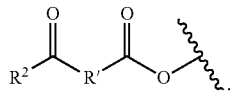

Embodiment 23 provides the tackifier compound of any one of Embodiments 1-22, wherein $R^2$ is —OH.

Embodiment 24 provides the tackifier compound of any one of Embodiments 1-23, wherein the compound has the structure

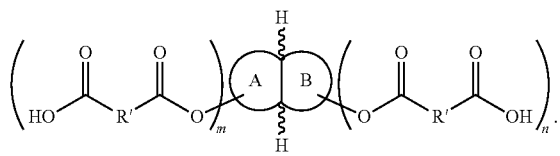

Embodiment 25 provides the tackifier compound of any one of Embodiments 1-24, wherein $R^2$ is —$OR^3$.

Embodiment 26 provides the tackifier compound of Embodiment 25, wherein $R^3$ is —O($C_1$-$C_5$)alkyl.

Embodiment 27 provides the tackifier compound of any one of Embodiments 25-26, wherein $R^3$ is —OMe.

Embodiment 28 provides the tackifier compound of any one of Embodiments 1-27, wherein at each occurrence R' is independently unsubstituted.

Embodiment 29 provides the tackifier compound of any one of Embodiments 1-28, wherein at each occurrence R' is independently ($C_1$-$C_5$)alkylene, ($C_5$-$C_{10}$)aryl, or ($C_2$-$C_5$)alkenylene.

Embodiment 30 provides the tackifier compound of any one of Embodiments 1-29, wherein at each occurrence R' is independently —$CH_2$—$CH_2$—, —$CH_2$—$CH_2$—$CH_2$—, o-phenylene, or —CH=CH—.

Embodiment 31 provides the tackifier compound of any one of Embodiments 1-30, wherein rings A and B are unsubstituted with the exception of the one or more ester substituents —OC(O)—R'—C(O)$R^2$.

Embodiment 32 provides the tackifier compound of any one of Embodiments 1-31, wherein m=n=1, and one of the ester substituents including R' and R" is alpha to at least one carbon atom shared by rings A and B.

Embodiment 33 provides the tackifier compound of any one of Embodiments 1-32, wherein rings A and B are the same size.

Embodiment 34 provides the tackifier compound of any one of Embodiments 1-33, wherein rings A and B are 5-membered rings.

Embodiment 35 provides the tackifier compound of any one of Embodiments 1-34, wherein at least one of rings A and B include at least one oxygen atom.

Embodiment 36 provides the tackifier compound of any one of Embodiments 1-35, wherein each of rings A and B is a tetrahydrofuran ring, wherein each carbon atom shared by rings A and B has an oxygen atom alpha thereto.

Embodiment 37 provides the tackifier compound of any one of Embodiments 1-36, wherein m=n.

Embodiment 38 provides the tackifier compound of any one of Embodiments 1-37, wherein m=n=1.

Embodiment 39 provides the tackifier compound of Embodiment 38, wherein each of $R^1$ and the ester substituent —OC(O)—R'—C(O)$R^2$ are alpha to a different carbon atom shared by each of rings A and B.

Embodiment 40 provides the tackifier compound of any one of Embodiments 1-39, wherein rings A and B form a ring system chosen from isosorbide, isomannide, and isoidide.

Embodiment 41 provides the tackifier compound of any one of Embodiments 1-40, wherein rings A and B are unsubstituted.

Embodiment 42 provides the tackifier compound of any one of Embodiments 1-41, wherein the compound is chosen from

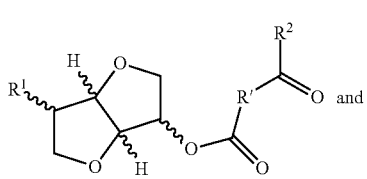 and

-continued
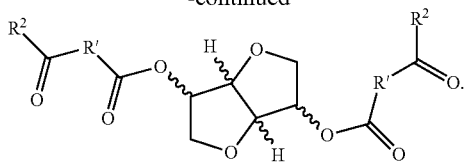 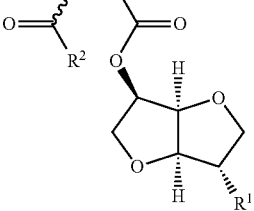 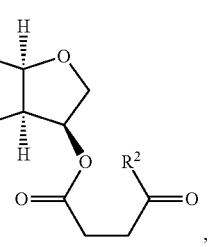
Embodiment 43 provides the tackifier compound of any one of Embodiments 1-42, wherein the compound is
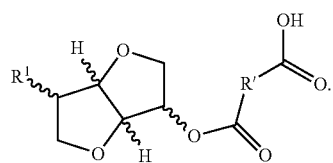
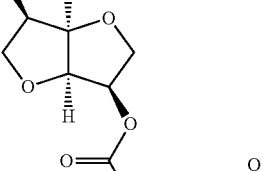 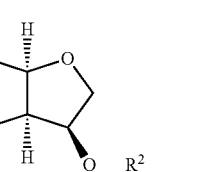
Embodiment 44 provides the tackifier compound of any one of Embodiments 1-43, wherein the compound is
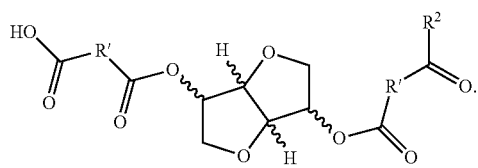
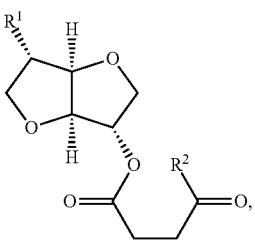 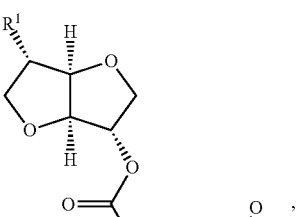
Embodiment 45 provides the tackifier compound of any one of Embodiments 1-44, wherein the compound is chosen from
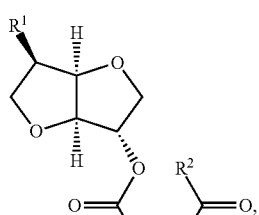 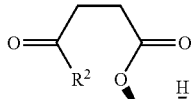
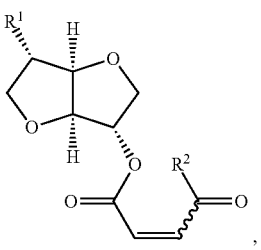
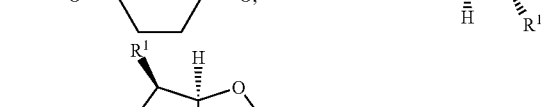
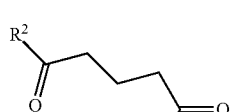 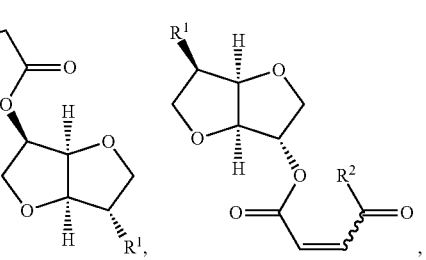
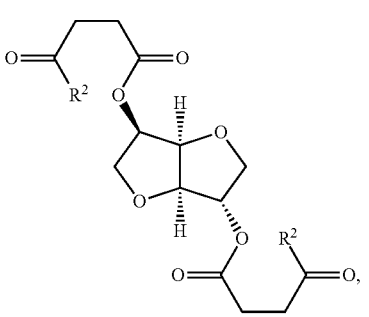

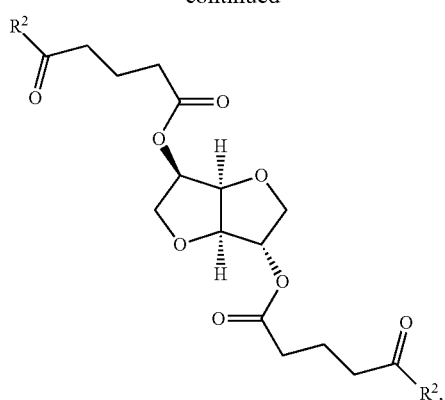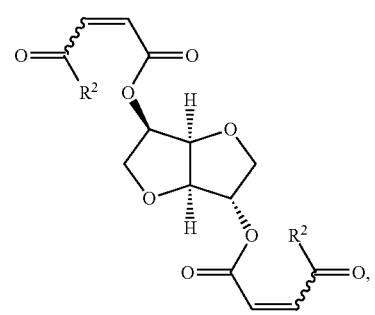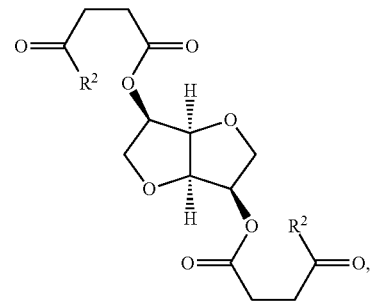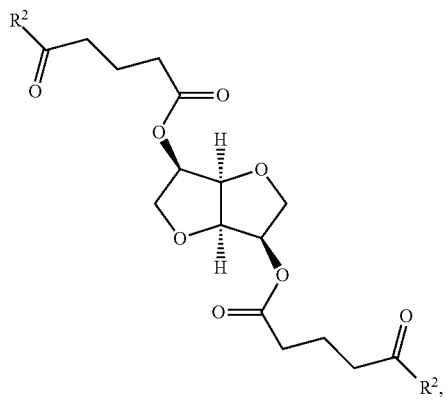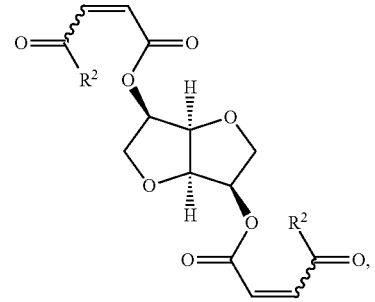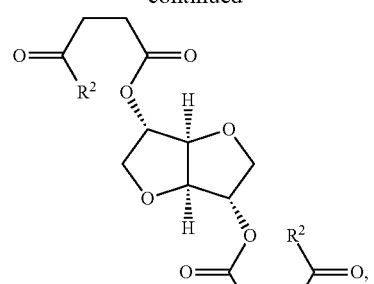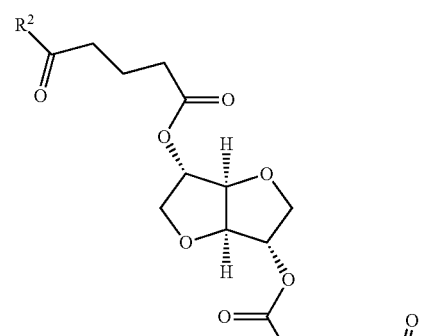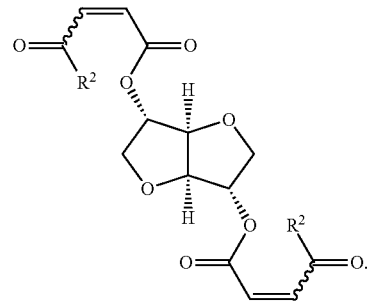
Embodiment 46 provides the tackifier compound of any one of Embodiments 1-45, wherein the compound is chosen from
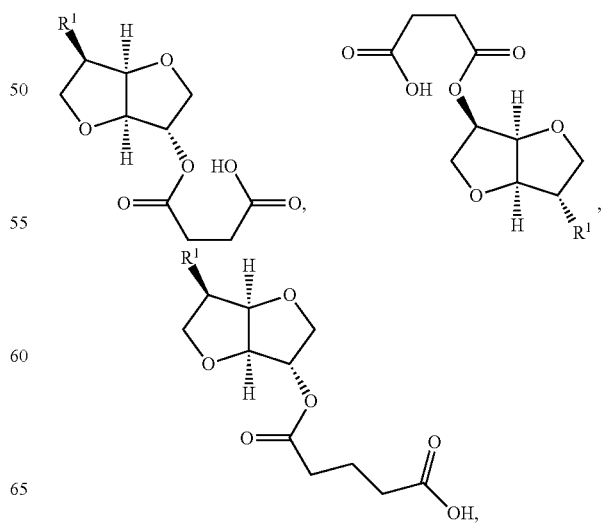

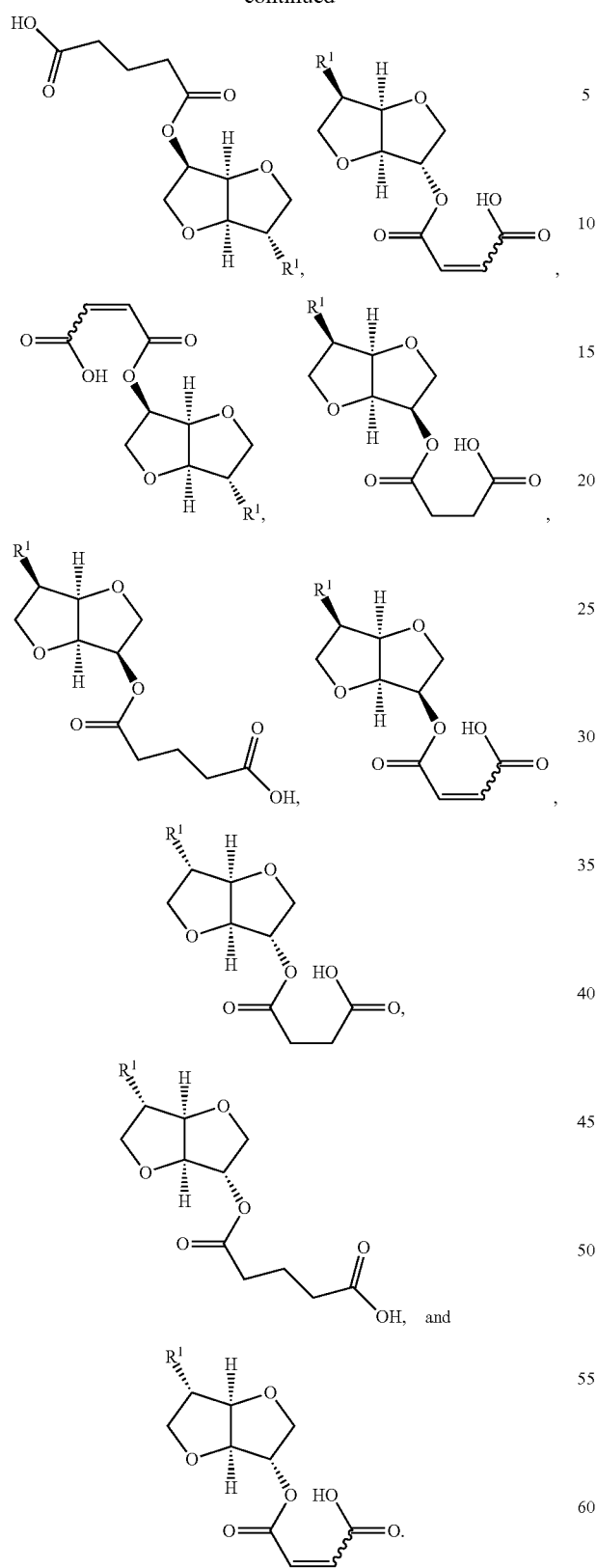
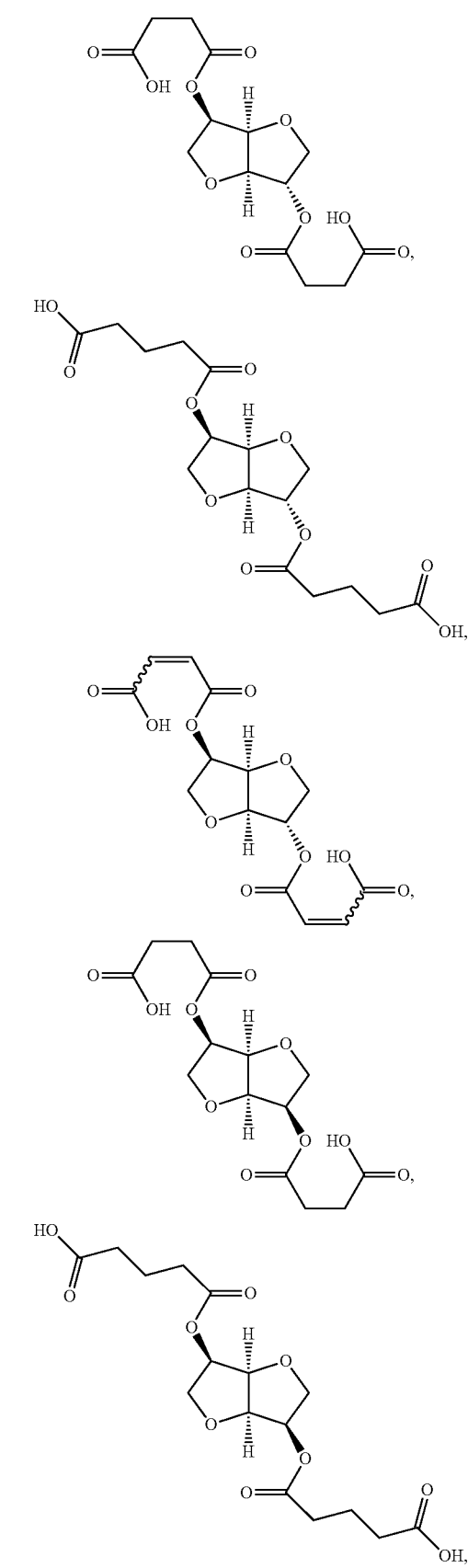
Embodiment 47 provides the tackifier compound of any one of Embodiments 1-46, wherein the compound is chosen from 69
-continued
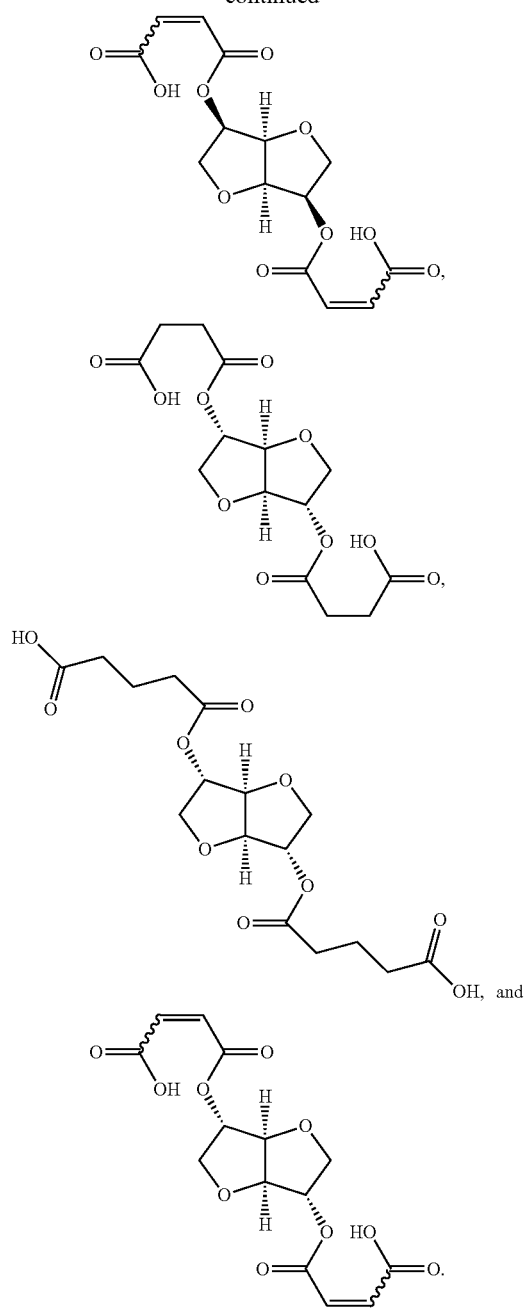
Embodiment 48 provides the tackifier compound of any one of Embodiments 1-47, wherein the compound is chosen from
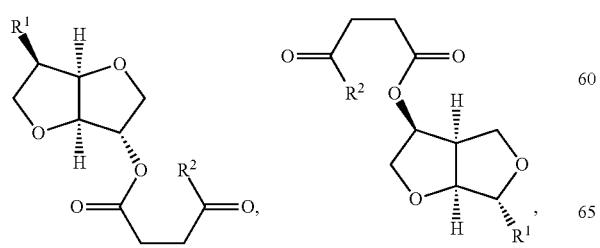
70
-continued
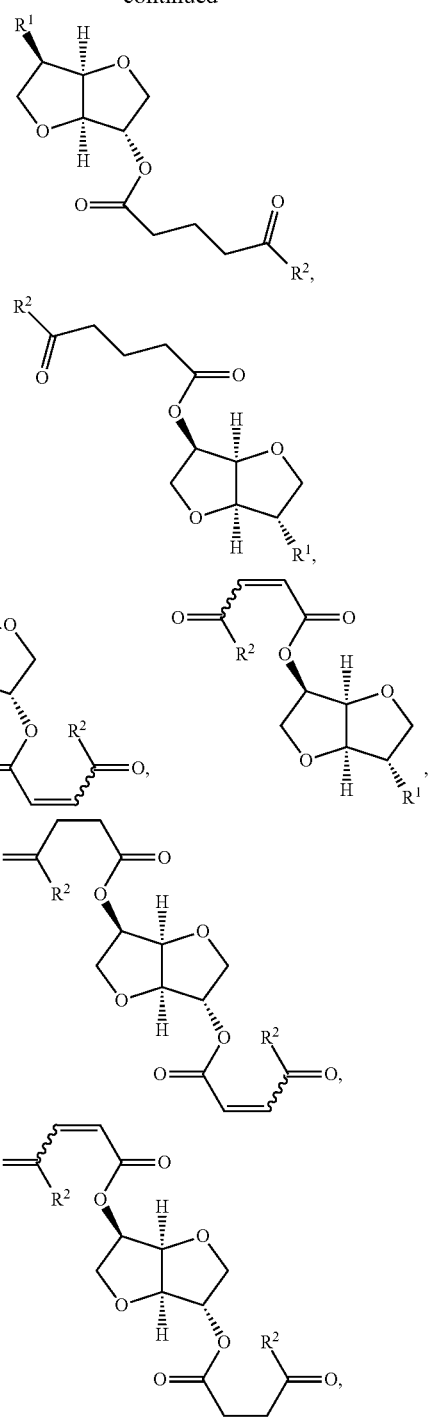

-continued
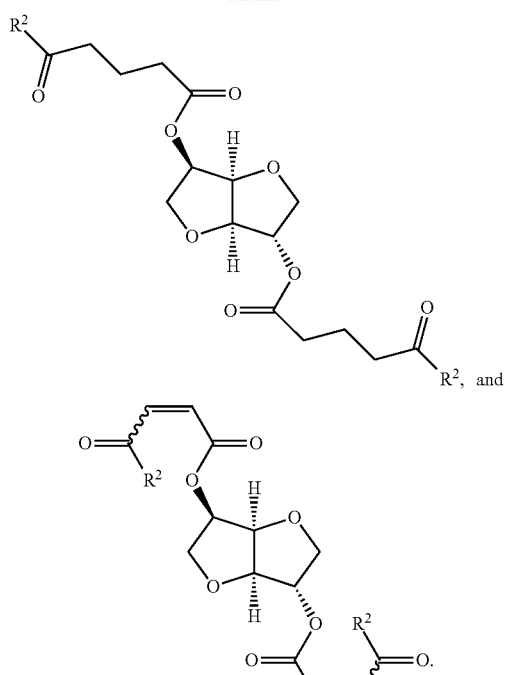
Embodiment 49 provides the tackifier compound of any one of Embodiments 1-48, wherein the compound is chosen from
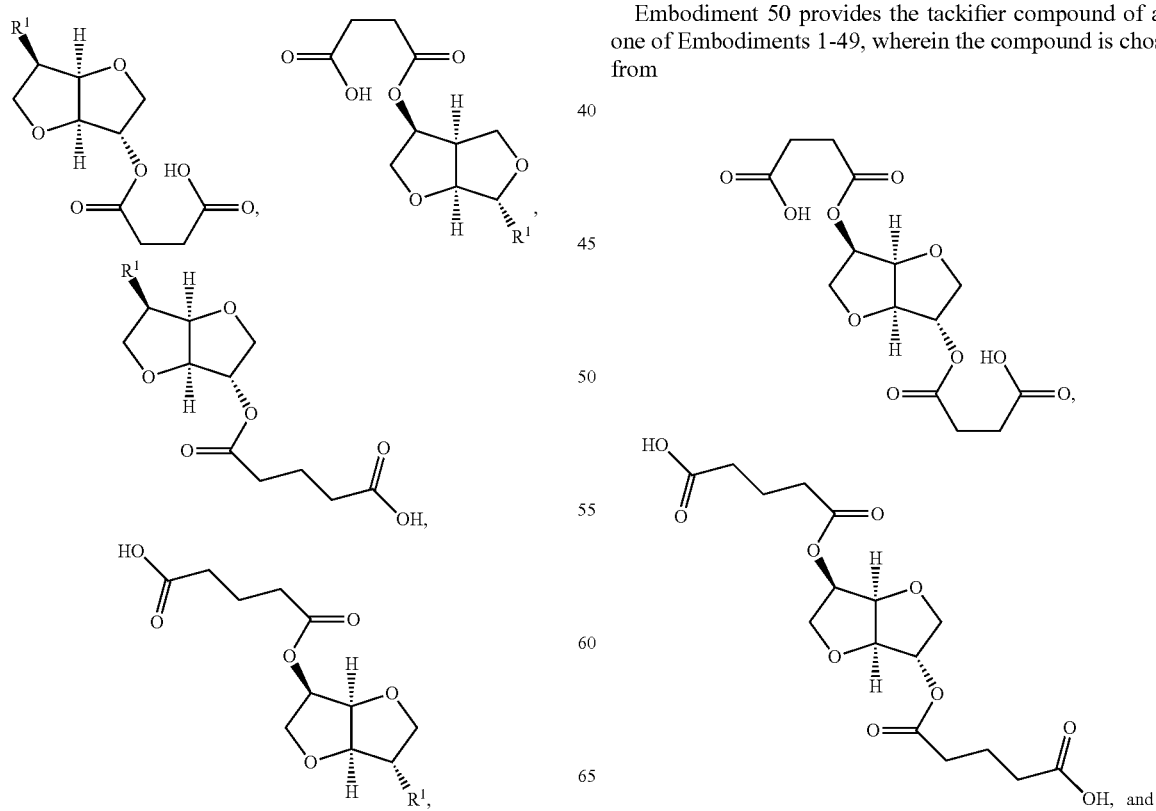
-continued
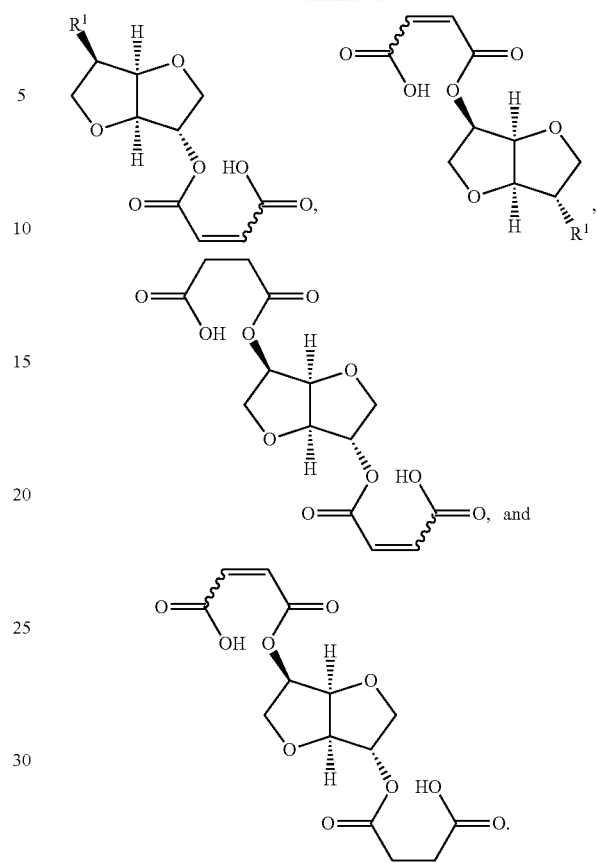
Embodiment 50 provides the tackifier compound of any one of Embodiments 1-49, wherein the compound is chosen from

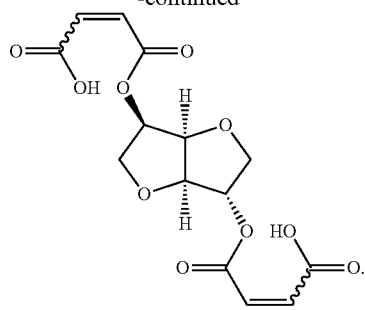

Embodiment 51 provides the tackifier compound of any one of Embodiments 1-50, wherein at least one R' is $C_1$-$C_{10}$ alkenylene or $C_1$-$C_{10}$ alkynylene.

Embodiment 52 provides a reaction product of the tackifier compound of Embodiment 51.

Embodiment 53 provides a composition comprising the tackifier compound of Embodiment 51 and a free-radical initiator or a transition metal catalyst.

Embodiment 54 provides the composition of Embodiment 53, wherein the free-radical initiator is chosen from tert-amyl peroxybenzoate, 4,4-azobis(4-cyanovaleric acid), 1,1'-azobis(cyclohexanecarbonitrile), 2,2'-azobisisobutyronitrile (AIBN), benzoyl peroxide, 2,2-bis-(tert-butylperoxy)butane, 1,1-bis(tert-butylperoxy)cyclohexane, 2,5-bis(tert-butylperoxy)-2,6-dimethylhexane, 2,5-bis(tert-butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, tert-butyl hydroperoxide, tert-butyl peracetate, tert-butyl peroxybenzoate, tert-butylperoxy isopropyl carbonate, cumene hydroperoxide, cyclohexanone peroxide, dicumyl peroxide, lauroyl peroxide, 2,4-pentanedione peroxide, peracetic acid, and potassium persulfate, or wherein the transition metal catalyst is a Ziegler-Natta catalyst or a Phillips catalyst.

Embodiment 55 provides the tackifier compound of any one of Embodiments 1-51, wherein the compound is chosen from

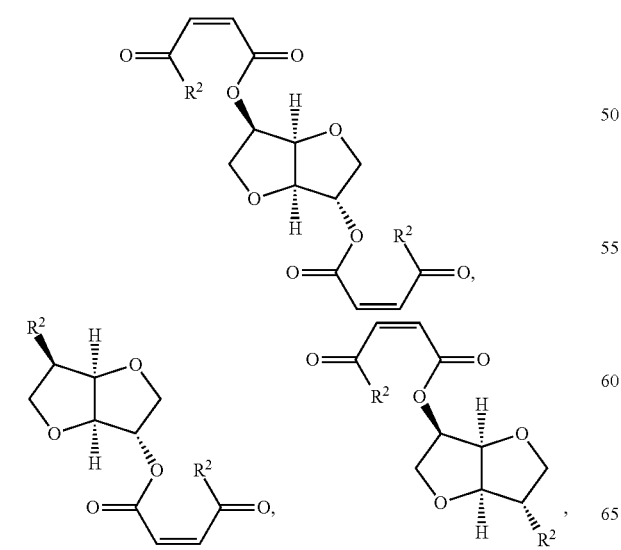

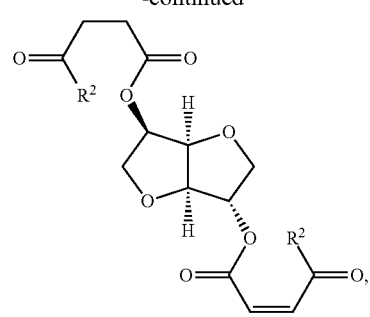

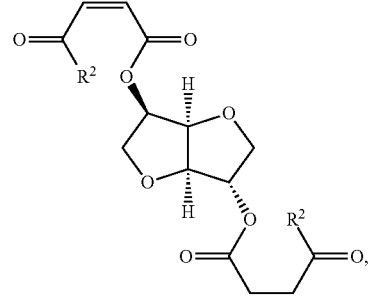

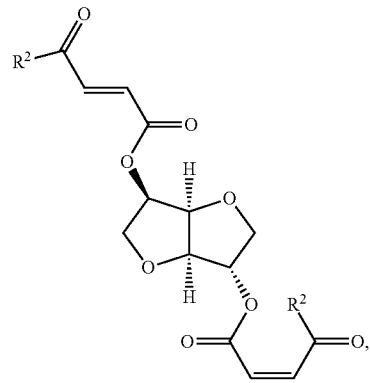

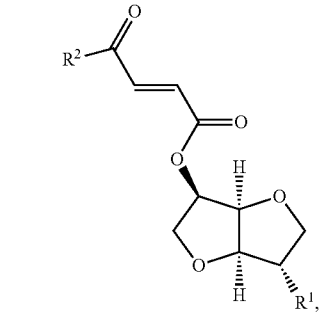

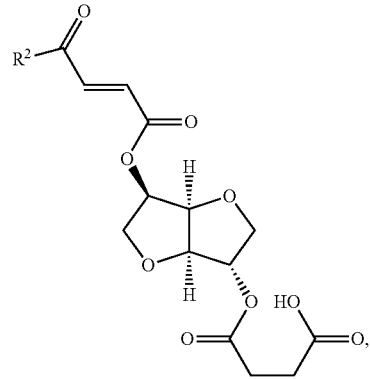

75
-continued
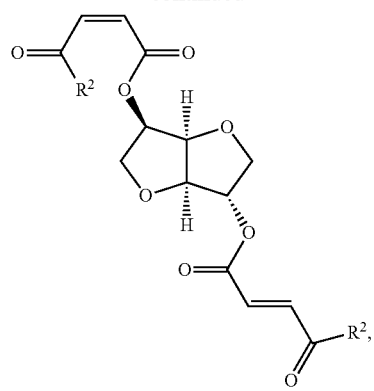
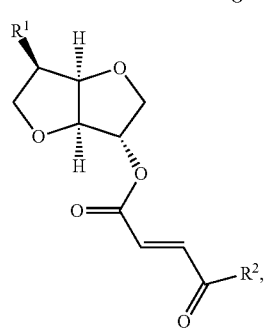
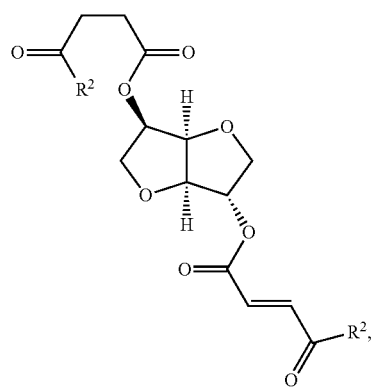
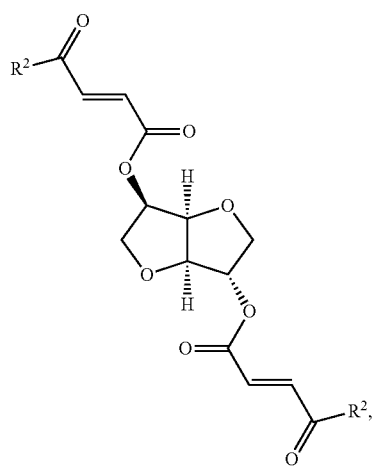
76
-continued
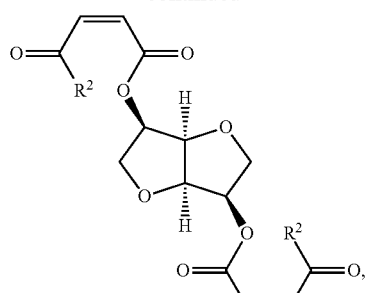
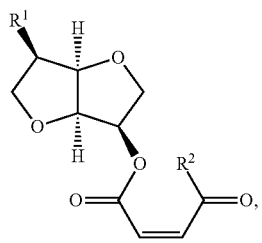
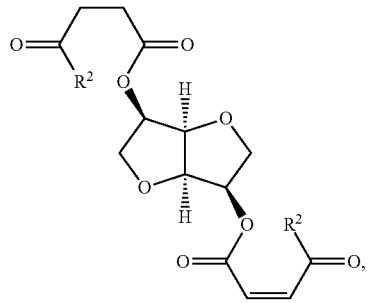
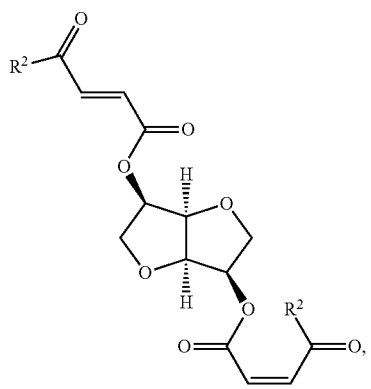
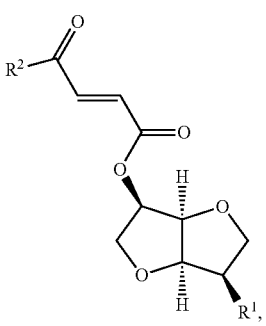

77
-continued
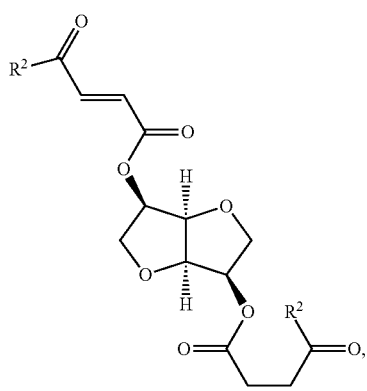
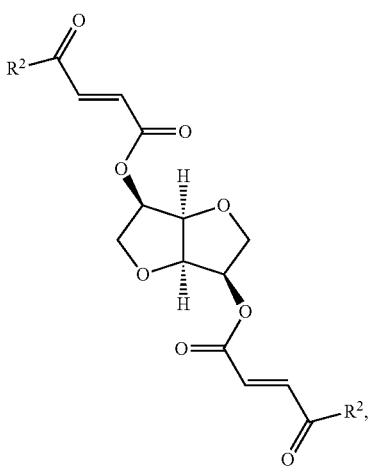
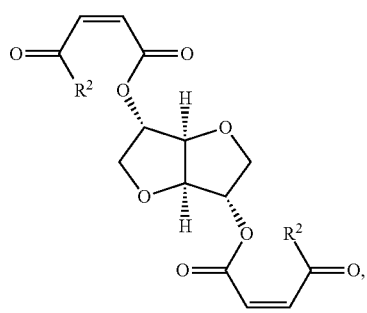
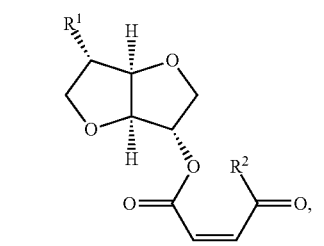
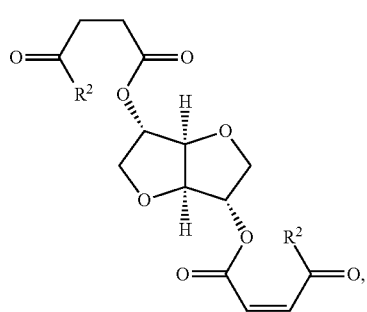
78
-continued
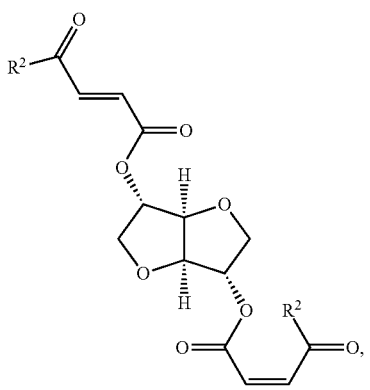
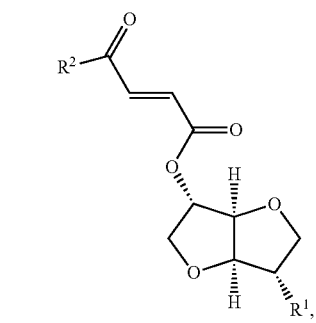
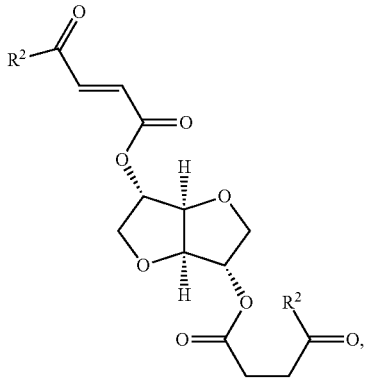
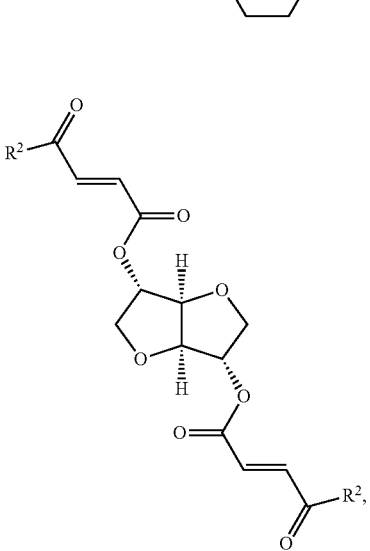

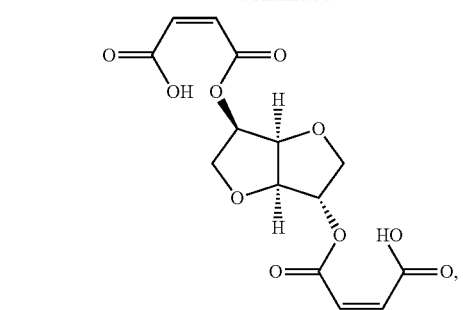
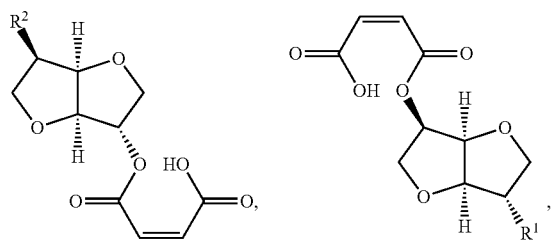
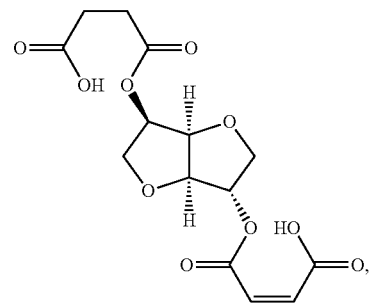
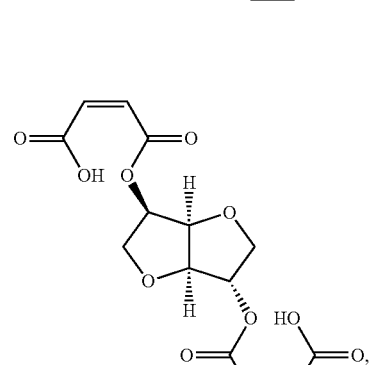
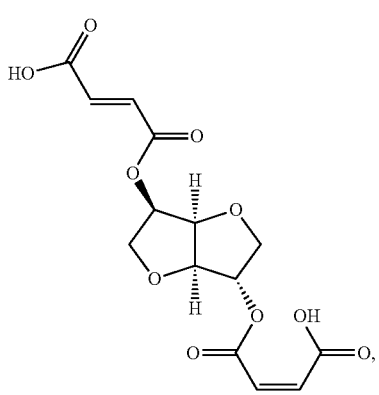
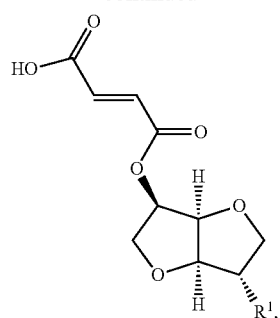
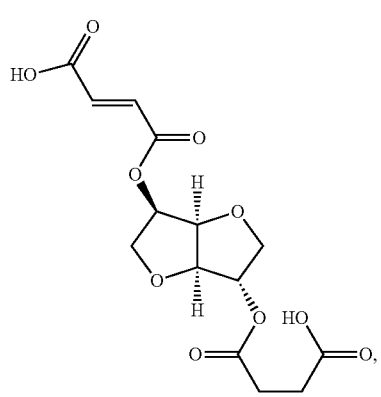
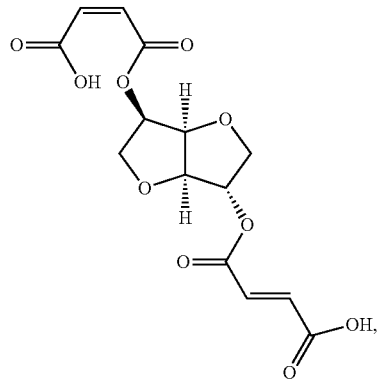
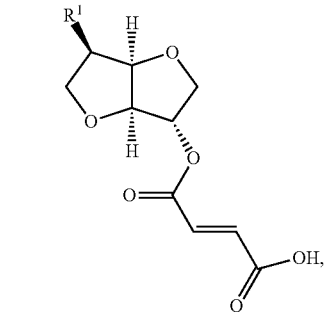

-continued
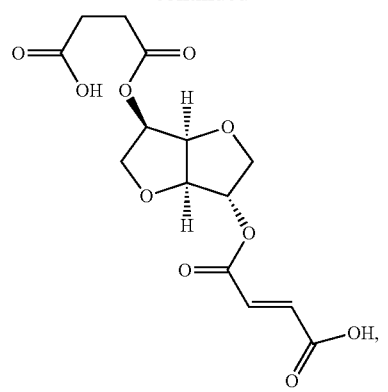
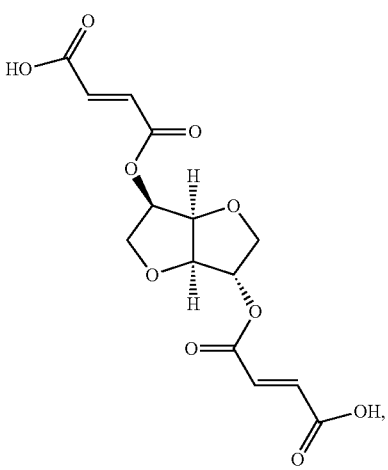
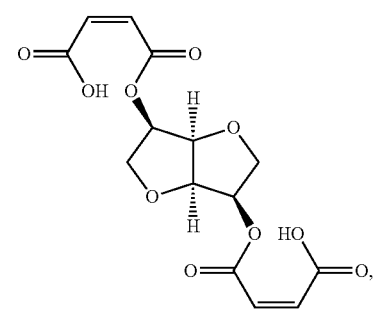
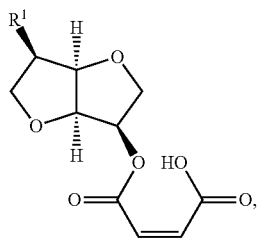
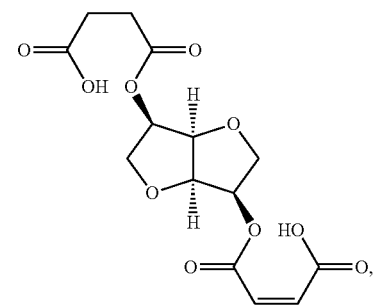
-continued
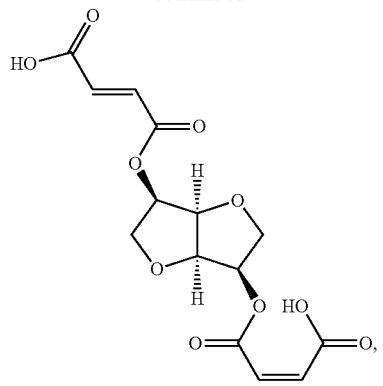
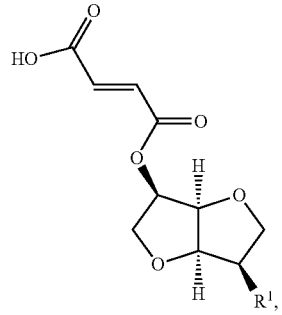
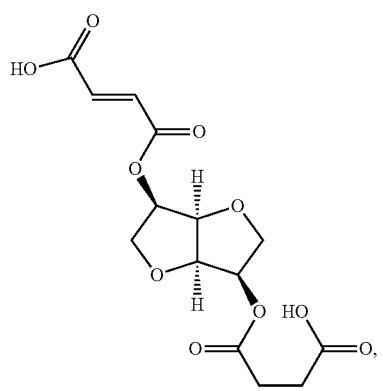
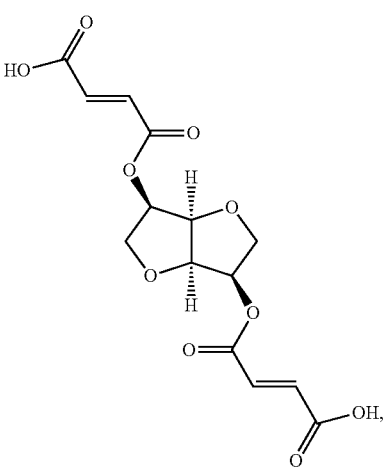

-continued

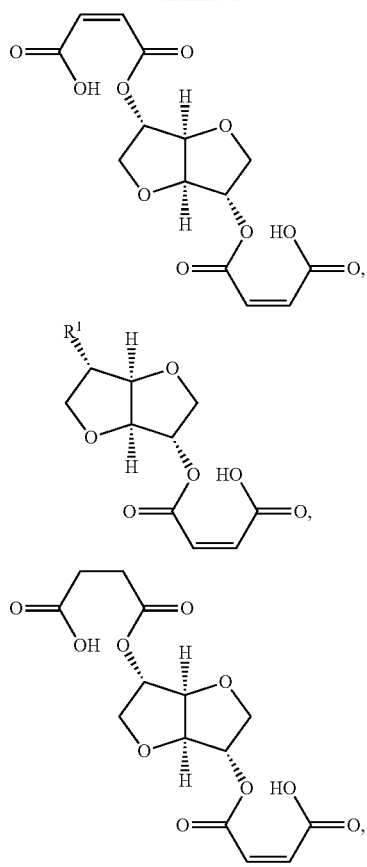

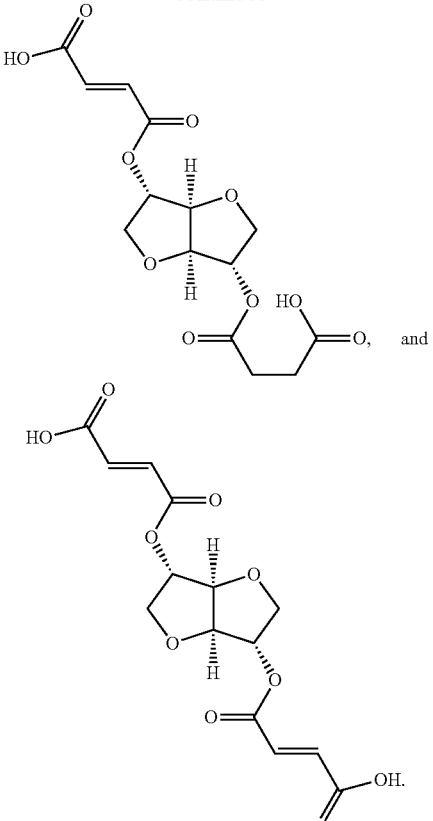

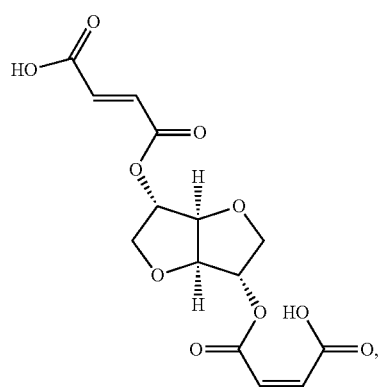

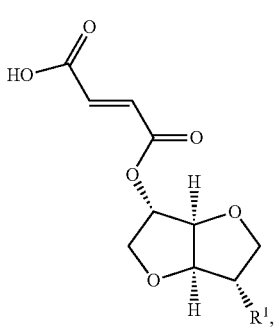

Embodiment 56 provides a reaction product of the tackifier compound of Embodiment 55.

Embodiment 57 provides the reaction product of Embodiment 56, wherein the reaction product is a cured product.

Embodiment 58 provides the reaction product of any one of Embodiments 56-57, wherein the reaction product is at least one of a free-radical polymerization product and a transition metal-catalyzed polymerization product.

Embodiment 59 provides a polymer comprising a repeating unit having the structure

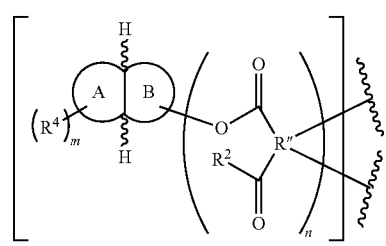

or a salt thereof;

wherein fused rings A and B are each independently chosen from ($C_5$-$C_{10}$)cycloalkyl and ($C_2$-$C_{10}$)heterocyclyl;

m and n are each independently 1-8;

at each occurrence $R^4$ is independently selected from —OH, —OR$^3$,

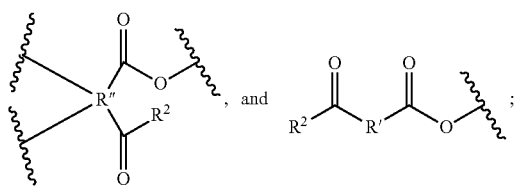

at each occurrence R' is independently chosen from $(C_2-C_{10})$alkanylene, $(C_2-C_{10})$alkenylene, $(C_2-C_{10})$alkynylene, $C_5-C_{20}$(arylene), and $(C_1-C_{20})$heteroarylene, wherein R' is unsubstituted or substituted with at least one J;

at each occurrence R" is independently a $(C_2-C_{10})$alkanylene bonded to at least one of a repeating unit and an end-blocking unit of the polymer at two locations, wherein R" is unsubstituted or substituted with at least one J;

at each occurrence $R^2$ is independently chosen from —OH, —$OR^3$, —$NH_2$, —$NHR^3$, and —$NR^3{}_2$;

at each occurrence $R^3$ is independently chosen from $(C_1-C_{10})$alkanyl, $(C_2-C_{10})$alkenyl, $(C_2-C_{10})$alkynyl, $C_5-C_{20}$(aryl), and $(C_1-C_{20})$heteroaryl, wherein $R^3$ is unsubstituted or substituted with at least one J;

fused rings A and B are each independently unsubstituted or substituted with at least one of J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0-C_{10})$alkyl, or $(C_1-C_{10})$heteroaryl$(C_0-C_{10})$alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J; and wherein J independently at each occurrence is chosen from F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, C(O)$CH_2$C(O)R, C(S)R, C(O)OR, OC(O)R, OC(O)OR, C(O)$N(R)_2$, OC(O)$N(R)_2$, C(S)$N(R)_2$, $(CH_2)_{0-2}$NHC(O)R, N(R)N(R)C(O)R, N(R)N(R)C(O)OR, N(R)N(R)C(O)$N(R)_2$, N(R)$SO_2R$, N(R)$SO_2N(R)_2$, N(R)C(O)OR, N(R)C(O)R, N(R)C(S)R, N(R)C(O)$N(R)_2$, N(R)C(S)$N(R)_2$, N(C(O)R)C(O)R, N(OR)R, C(=NH)$N(R)_2$, C(O)N(OR)R, and C(=NOR)R, wherein R is independently at each occurrence chosen from hydrogen, $(C_1-C_{10})$alkyl, $(C_1-C_{10})$cycloalkyl, $(C_1-C_{10})$cycloalkyl$(C_1-C_{10})$alkyl, $(C_1-C_{10})$aryl, $(C_1-C_{10})$aralkyl, $(C_1-C_{10})$heterocyclyl, $(C_1-C_{10})$heterocyclyl$(C_1-C_{10})$alkyl, $(C_1-C_{10})$heteroaryl, and $(C_1-C_{10})$heteroaryl$(C_1-C_{10})$alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

Embodiment 60 provides the polymer of Embodiment 59, wherein the repeating unit has a structure chosen from

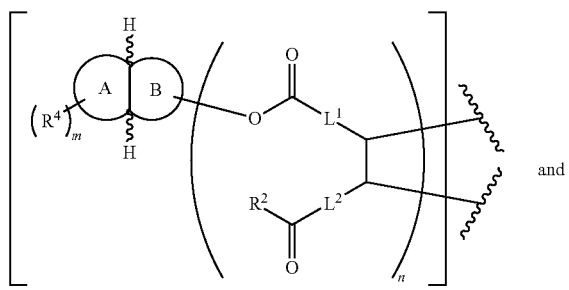

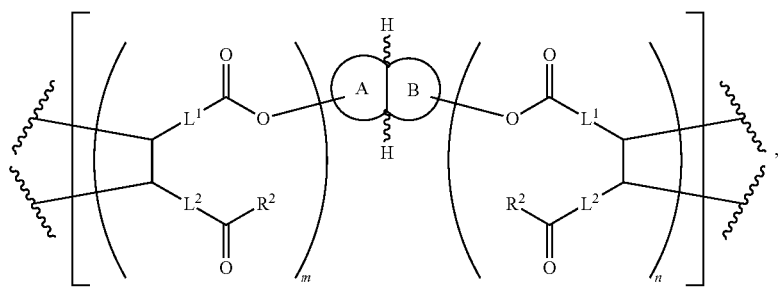

wherein at each occurrence $L^1$ and $L^2$ are independently chosen from a bond and $(C_1-C_{10})$alkyl, and wherein at each occurrence $R^4$ is independently selected from —OH, —$OR^3$,

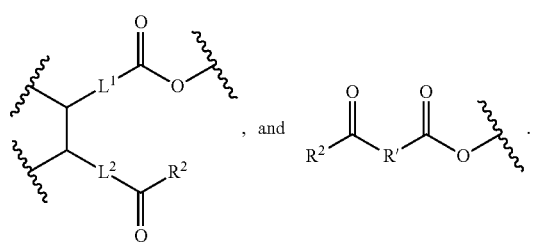

Embodiment 61 provides the polymer of any one of Embodiments 59-60, wherein the repeating unit has the structure

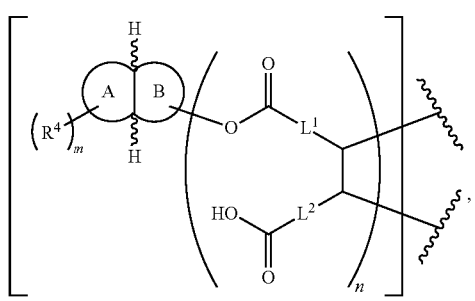

wherein at each occurrence $L^1$ and $L^2$ are independently chosen from a bond and $(C_1\text{-}C_{10})$alkyl, and wherein at each occurrence $R^4$ is independently selected from —OH, —OR$^3$,

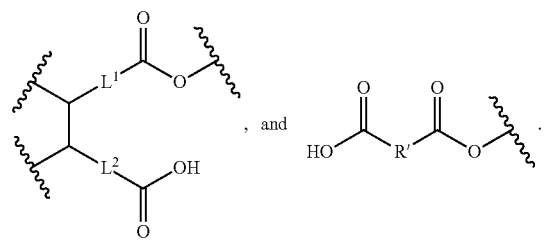

Embodiment 62 provides the polymer of any one of Embodiments 59-61, wherein the repeating unit has the structure

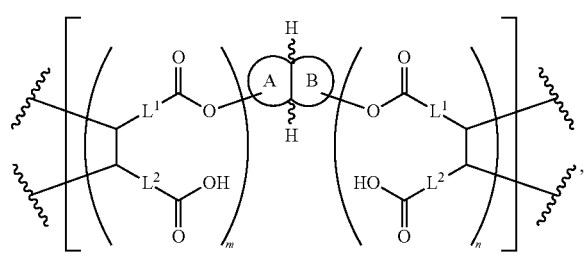

wherein at each occurrence $L^1$ and $L^2$ are independently chosen from a bond and $(C_1\text{-}C_{10})$alkyl.

Embodiment 63 provides the polymer of any one of Embodiments 59-62, wherein the repeating unit has a structure chosen from

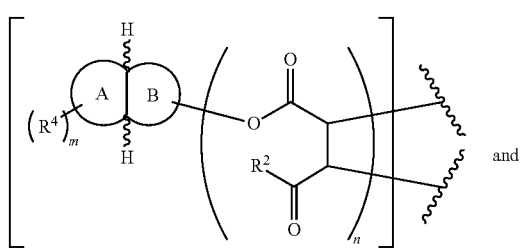

and

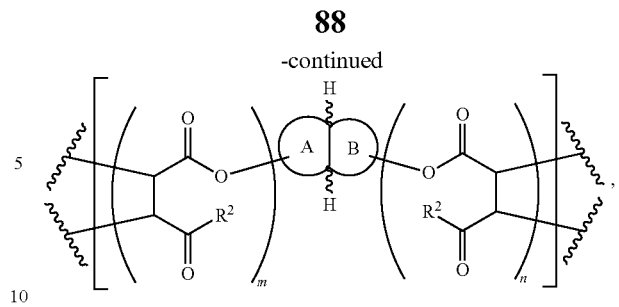

wherein at each occurrence $R^4$ is independently selected from —OH, —OR$^3$,

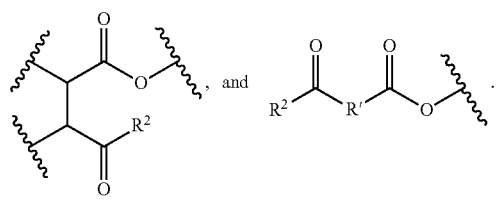

Embodiment 64 provides the polymer of any one of Embodiments 59-63, wherein the repeating unit has the structure

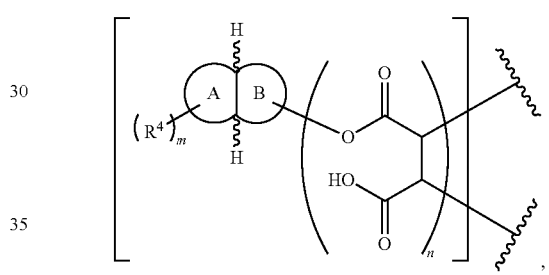

wherein at each occurrence $R^4$ is independently selected from —OH, —OR$^3$,

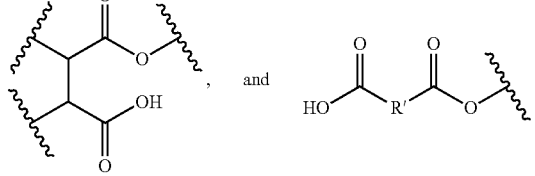

Embodiment 65 provides the polymer of any one of Embodiments 59-64, wherein the repeating unit has the structure

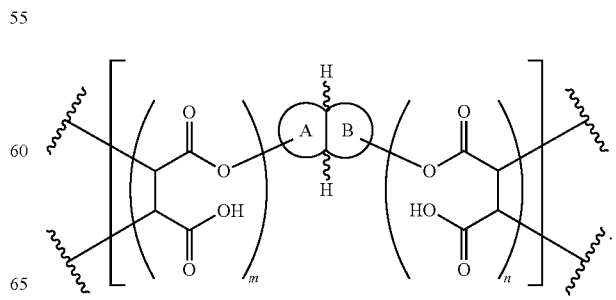

Embodiment 66 provides the polymer of any one of Embodiments 59-65, wherein rings A and B form a ring system chosen from isosorbide, isomannide, and isoidide.

Embodiment 67 provides the polymer of any one of Embodiments 59-66, wherein R" is an alkanylene bonded to at least one of a repeating unit and an end-blocking unit of the polymer at two locations and is chosen from ethylene, propylene, butylene, or pentylene.

Embodiment 68 provides the polymer of any one of Embodiments 59-67, wherein the repeating unit has a structure chosen from

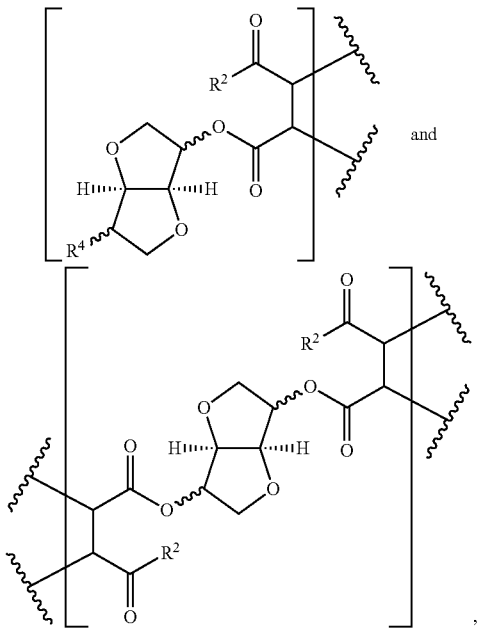

wherein at each occurrence $R^4$ is independently selected from —OH, —OR$^3$,

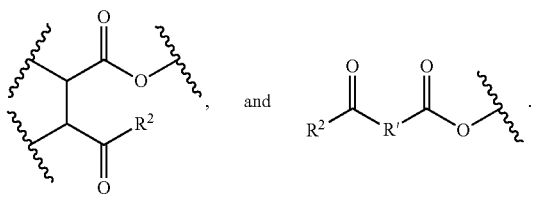

Embodiment 69 provides the polymer of any one of Embodiments 59-68, wherein the repeating unit has the structure

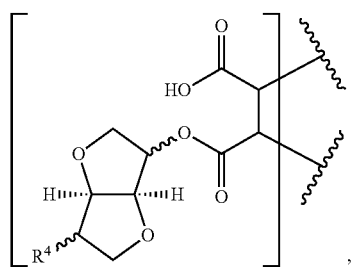

wherein at each occurrence $R^4$ is independently selected from —OH, —OR$^3$,

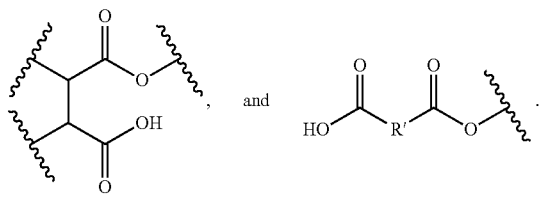

Embodiment 70 provides the polymer of any one of Embodiments 59-69, wherein the repeating unit has the structure

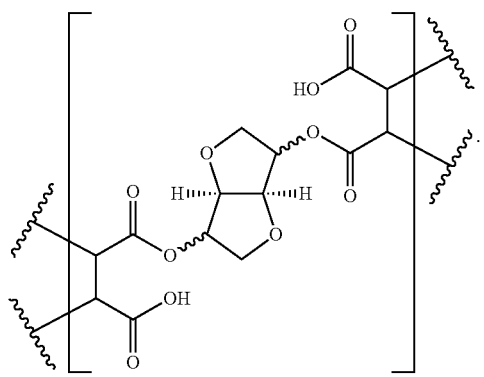

Embodiment 71 provides the polymer of any one of Embodiments 59-70, wherein the repeating unit has a structure chosen from

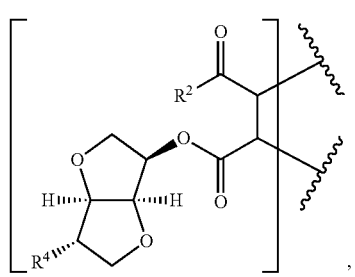

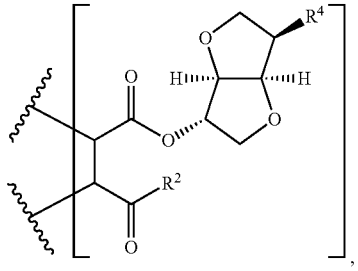

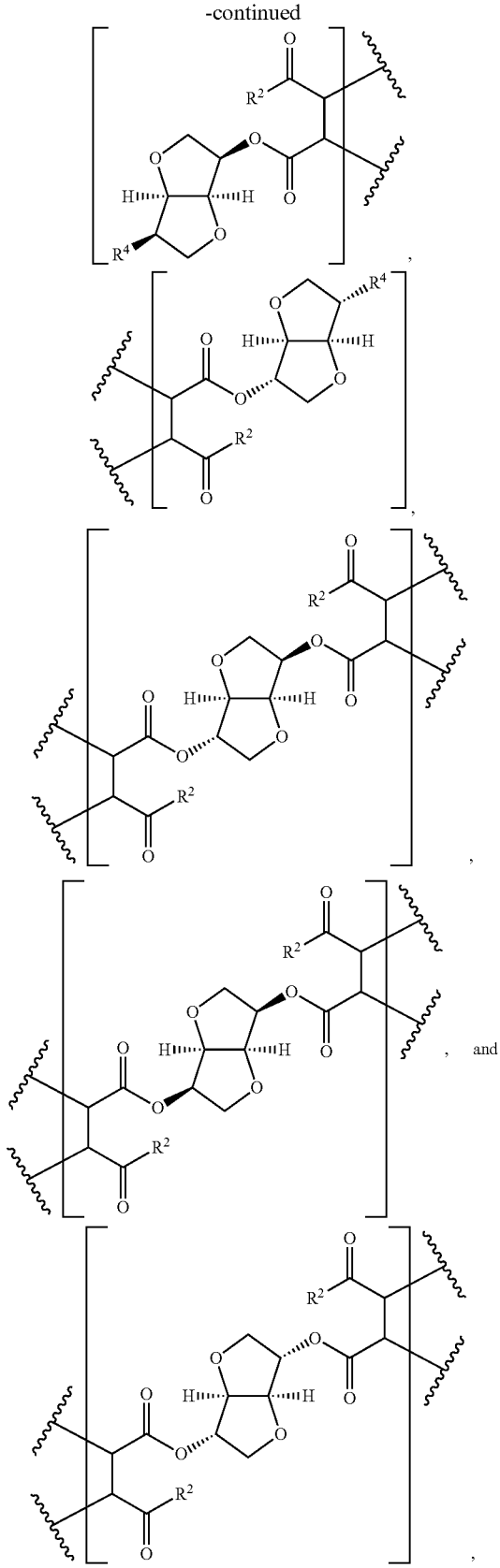
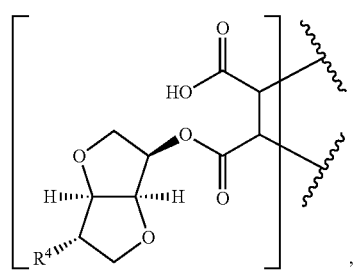
Embodiment 72 provides the polymer of any one of Embodiments 59-71, wherein the repeating unit has a structure chosen from
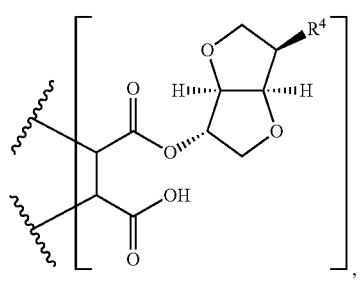
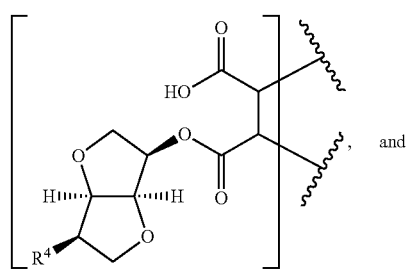
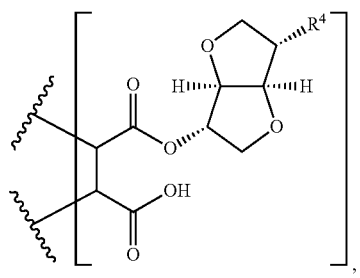
wherein at each occurrence $R^4$ is independently selected from —OH, —OR$^3$,
wherein at each occurrence $R^4$ is independently selected from —OH, —OR$^3$,

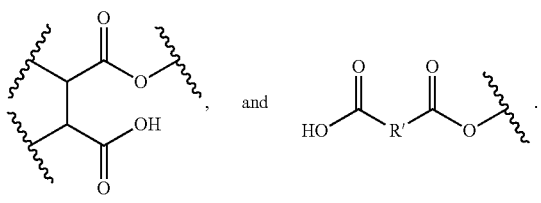

Embodiment 73 provides the polymer of any one of Embodiments 59-72, wherein the repeating unit has a structure chosen from

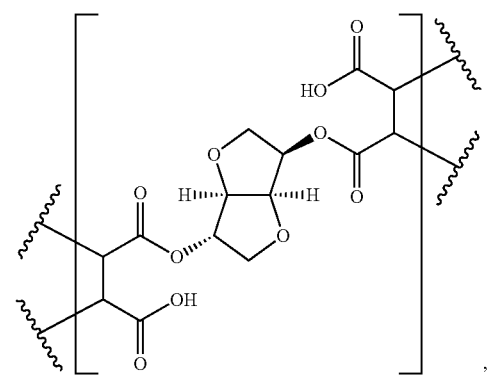

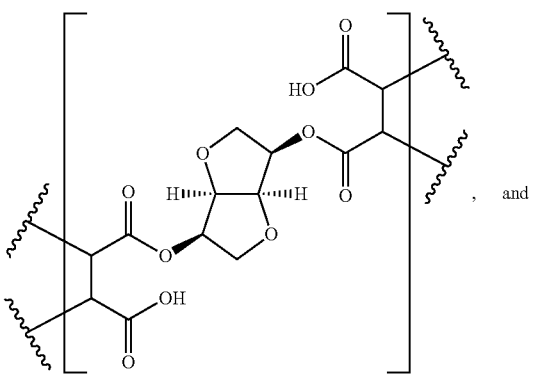

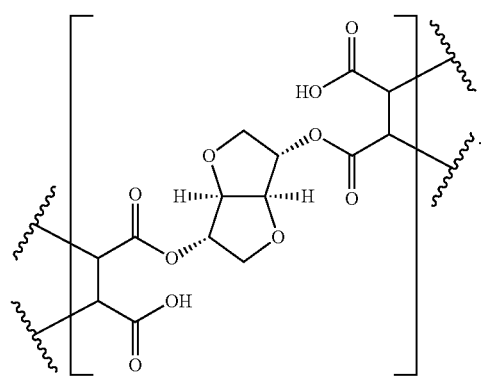

Embodiment 74 provides a system comprising:
a tackifier compound having the structural formula

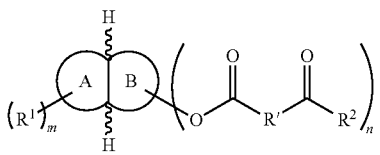

or a salt thereof;
wherein fused rings A and B are each independently chosen from $(C_5-C_{10})$cycloalkyl and $(C_2-C_{10})$heterocyclyl;
m and n are each independently 1-8;
at each occurrence $R^1$ is independently selected from —OH, —OR$^3$, and

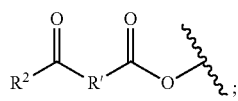

at each occurrence R' is independently chosen from $(C_2-C_{10})$alkanylene, $(C_2-C_{10})$alkenylene, $(C_2-C_{10})$alkynylene, $C_5-C_{20}$(arylene), and $(C_1-C_{20})$heteroarylene, wherein R' is unsubstituted or substituted with at least one J;
at each occurrence $R^2$ is independently chosen from —OH, —OR$^3$, —NH$_2$, —NHR$^3$, and —NR$^3{}_2$;
at each occurrence $R^3$ is independently chosen from $(C_1-C_{10})$alkanyl, $(C_2-C_{10})$alkenyl, $(C_2-C_{10})$alkynyl, $C_5-C_{20}$(aryl), and $(C_1-C_{20})$heteroaryl, wherein $R^3$ is unsubstituted or substituted with at least one J;
fused rings A and B are each independently unsubstituted or substituted with at least one of J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0-C_{10})$alkyl, or $(C_1-C_{10})$heteroaryl$(C_0-C_{10})$alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J; and
wherein J independently at each occurrence is chosen from F, Cl, Br, I, OR, CN, CF$_3$, OCF$_3$, R, O, S, C(O), S(O), methylenedioxy, ethylenedioxy, N(R)$_2$, SR, S(O)R, SO$_2$R, SO$_2$N(R)$_2$, SO$_3$R, C(O)R, C(O)C(O)R, C(O)CH$_2$C(O)R, C(S)R, C(O)OR, OC(O)R, OC(O)OR, C(O)N(R)$_2$, OC(O)N(R)$_2$, C(S)N(R)$_2$, (CH$_2$)$_{0-2}$NHC(O)R, N(R)N(R)C(O)R, N(R)N(R)C(O)OR, N(R)N(R)C(O)N(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(C(O)R)C(O)R, N(OR)R, C(=NH)N(R)$_2$, C(O)N(OR)R, and C(=NOR)R, wherein R is independently at each occurrence chosen from hydrogen, $(C_1-C_{10})$alkyl, $(C_1-C_{10})$cycloalkyl, $(C_1-C_{10})$cycloalkyl$(C_1-C_{10})$alkyl, $(C_1-C_{10})$aryl, $(C_1-C_{10})$aralkyl, $(C_1-C_{10})$heterocyclyl, $(C_1-C_{10})$heterocyclyl$(C_1-C_{10})$alkyl, $(C_1-C_{10})$heteroaryl, and $(C_1-C_{10})$heteroaryl$(C_1-C_{10})$alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J; and
a first substrate;
wherein the tackifier compound is bonded to the first substrate.

Embodiment 75 provides the system of Embodiment 74, further comprising a second substrate, wherein the tackifier compound is bonded to the first and second substrate such as to bond the first substrate to the second substrate at least partially via the tackifier compound.

Embodiment 76 provides a system comprising:
a polymer comprising a repeating unit having the structure

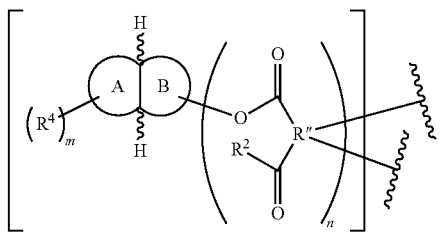

or a salt thereof;
wherein fused rings A and B are each independently chosen from $(C_5-C_{10})$cycloalkyl and $(C_2-C_{10})$heterocyclyl;
m and n are each independently 1-8;
at each occurrence $R^4$ is independently selected from —OH, —OR$^3$,

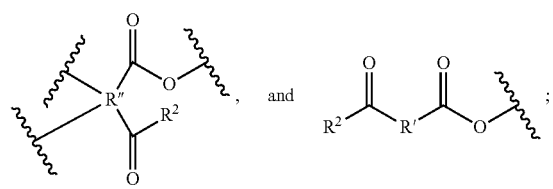

at each occurrence R' is independently chosen from $(C_2-C_{10})$alkanylene, $(C_2-C_{10})$alkenylene, $(C_2-C_{10})$alkynylene, $C_5-C_{20}$(arylene), and $(C_1-C_{20})$heteroarylene, wherein R' is unsubstituted or substituted with at least one J;
at each occurrence R" is independently a $(C_2-C_{10})$alkanylene bonded to at least one of a repeating unit and an end-blocking unit of the polymer at two locations, wherein R" is unsubstituted or substituted with at least one J;
at each occurrence $R^2$ is independently chosen from —OH, —OR$^3$, —NH$_2$, —NHR$^3$, and —NR$^3{}_2$;
at each occurrence $R^3$ is independently chosen from $(C_1-C_{10})$alkanyl, $(C_2-C_{10})$alkenyl, $(C_2-C_{10})$alkynyl, $C_5-C_{20}$(aryl), and $(C_1-C_{20})$heteroaryl, wherein $R^3$ is unsubstituted or substituted with at least one J;
fused rings A and B are each independently unsubstituted or substituted with at least one of J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0-C_{10})$alkyl, or $(C_1-C_{10})$heteroaryl$(C_0-C_{10})$alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J; and
wherein J independently at each occurrence is chosen from F, Cl, Br, I, OR, CN, CF$_3$, OCF$_3$, R, O, S, C(O), S(O), methylenedioxy, ethylenedioxy, N(R)$_2$, SR, S(O)R, SO$_2$R, SO$_2$N(R)$_2$, SO$_3$R, C(O)R, C(O)C(O)R, C(O)CH$_2$C(O)R, C(S)R, C(O)OR, OC(O)R, OC(O)OR, C(O)N(R)$_2$, OC(O)N(R)$_2$, C(S)N(R)$_2$, (CH$_2$)$_{0-2}$NHC(O)R, N(R)N(R)C(O)R, N(R)N(R)C(O)OR, N(R)N(R)C(O)N(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(C(O)R)C(O)R, N(OR)R, C(=NH)N(R)$_2$, C(O)N(OR)R, and C(=NOR)R, wherein R is independently at each occurrence chosen from hydrogen, $(C_1-C_{10})$alkyl, $(C_1-C_{10})$cycloalkyl, $(C_1-C_{10})$cycloalkyl$(C_1-C_{10})$alkyl, $(C_1-C_{10})$aryl, $(C_1-C_{10})$aralkyl, $(C_1-C_{10})$heterocyclyl, $(C_1-C_{10})$heterocyclyl$(C_1-C_{10})$alkyl, $(C_1-C_{10})$heteroaryl, and $(C_1-C_{10})$heteroaryl$(C_1-C_{10})$alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J and
a first substrate;
wherein the polymer is bonded to the first substrate.

Embodiment 77 provides the system of Embodiment 76, further comprising a second substrate, wherein the polymer is bonded to the first and second substrate such as to bond the first substrate to the second substrate via the polymer.

Embodiment 78 provides a method of using a tackifier compound having the structure

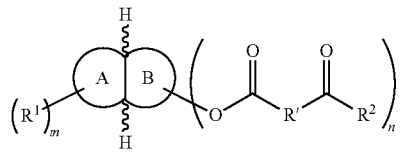

or a salt thereof;
wherein fused rings A and B are each independently chosen from $(C_5-C_{10})$cycloalkyl and $(C_2-C_{10})$heterocyclyl;
m and n are each independently 1-8;
at each occurrence $R^1$ is independently selected from —OH, —OR$^3$, and

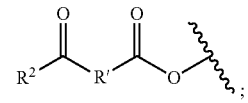

at each occurrence R' is independently chosen from $(C_2-C_{10})$alkanylene, $(C_2-C_{10})$alkenylene, $(C_2-C_{10})$alkynylene, $C_5-C_{20}$(arylene), and $(C_1-C_{20})$heteroarylene, wherein R' is unsubstituted or substituted with at least one J;
at each occurrence $R^2$ is independently chosen from —OH, —OR$^3$, —NH$_2$, —NHR$^3$, and —NR$^3{}_2$;
at each occurrence $R^3$ is independently chosen from $(C_1-C_{10})$alkanyl, $(C_2-C_{10})$alkenyl, $(C_2-C_{10})$alkynyl, $C_5-C_{20}$(aryl), and $(C_1-C_{20})$heteroaryl, wherein $R^3$ is unsubstituted or substituted with at least one J;
fused rings A and B are each independently unsubstituted or substituted with at least one of J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0-C_{10})$alkyl, or $(C_1-C_{10})$heteroaryl$(C_0-C_{10})$alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J; and wherein J independently at each occurrence is chosen from F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, OC(O)$N(R)_2$, $C(S)N(R)_2$, $(CH_2)_{0-2}NHC(O)R$, N(R)N(R)C(O)R, N(R)N(R)C(O)OR, N(R)N(R)C(O)$N(R)_2$, N(R)$SO_2R$, N(R)$SO_2N(R)_2$, N(R)C(O)OR, N(R)C(O)R, N(R)C(S)R, N(R)C(O)$N(R)_2$, N(R)C(S)$N(R)_2$, N(C(O)R)C(O)R, N(OR)R, C(=NH)$N(R)_2$, C(O)N(OR)R, and C(=NOR)R, wherein R is independently at each occurrence chosen from hydrogen, $(C_1-C_{10})$alkyl, $(C_1-C_{10})$cycloalkyl, $(C_1-C_{10})$cycloalkyl$(C_1-C_{10})$alkyl, $(C_1-C_{10})$aryl, $(C_1-C_{10})$aralkyl, $(C_1-C_{10})$heterocyclyl, $(C_1-C_{10})$heterocyclyl$(C_1-C_{10})$alkyl, $(C_1-C_{10})$heteroaryl, and $(C_1-C_{10})$heteroaryl$(C_1-C_{10})$alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J;

the method comprising contacting the tackifier compound to a first substrate such that the tackifier is bonded to the first substrate.

Embodiment 79 provides the method of Embodiment 78, further comprising contacting the tackifier compound to a second substrate such that the tackifier compound is bonded to the second substrate and such that the first substrate is bonded to the second substrate at least partially via the tackifier compound.

Embodiment 80 provides the method of any one of Embodiments 78-79, wherein at least one R' is $C_1-C_{10}$ alkenylene or $C_1-C_{10}$ alkynylene, the method further comprising crosslinking the tackifier compound to provide a polymer comprising a repeating unit comprising the structure

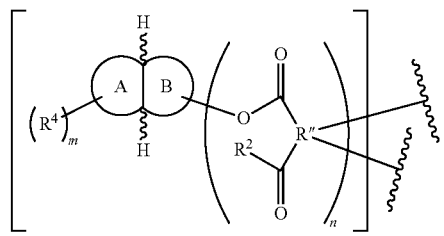

or a salt thereof;
wherein at each occurrence $R^4$ is independently selected from —OH, —$OR^3$,

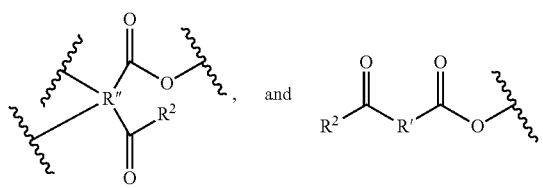

wherein at each occurrence R" is independently a $(C_2-C_{10})$alkanylene bonded to at least one of a repeating unit and an end-blocking unit of the polymer at two locations, wherein R" is unsubstituted or substituted with at least one J.

Embodiment 81 provides the method of Embodiment 80, wherein the crosslinking comprises at least one of application of heat, application of radiation, addition of a chemical crosslinker, and initiation of a chemical crosslinker.

Embodiment 82 provides the method of Embodiment 81, wherein the chemical crosslinker comprises a free-radical initiator.

Embodiment 83 provides a method of making a tackifier compound, comprising:
contacting
a compound having the structure

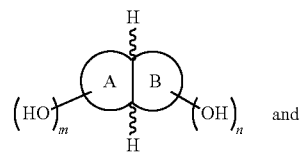

at least one acid anhydride having the structure

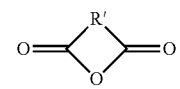

to provide a tackifier compound having the structure

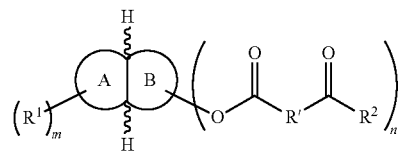

or a salt thereof;
wherein fused rings A and B are each independently chosen from $(C_5-C_{10})$cycloalkyl and $(C_2-C_{10})$heterocyclyl;
m and n are each independently 1-8;
at each occurrence $R^1$ is independently selected from —OH, —$OR^3$, and

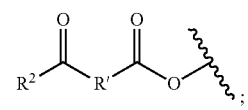

at each occurrence R' is independently chosen from $(C_2-C_{10})$alkanylene, $(C_2-C_{10})$alkenylene, $(C_2-C_{10})$alkynylene, $C_5-C_{20}$(arylene), and $(C_1-C_{20})$heteroarylene, wherein R' is unsubstituted or substituted with at least one J;
at each occurrence $R^2$ is independently chosen from —OH, —$OR^3$, —$NH_2$, —$NHR^3$, and —$NR^3_2$;
at each occurrence $R^3$ is independently chosen from $(C_1-C_{10})$alkanyl, $(C_2-C_{10})$alkenyl, $(C_2-C_{10})$alkynyl, $C_5-C_{20}$(aryl), and $(C_1-C_{20})$heteroaryl, wherein $R^3$ is unsubstituted or substituted with at least one J;
fused rings A and B are each independently unsubstituted or substituted with at least one of J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0$-

$C_{10}$)alkyl, or ($C_1$-$C_{10}$)heteroaryl($C_0$-$C_{10}$)alkyl; wherein each alkyl, alkenyl, alkynyl, haloalkyl, alkoxy, haloalkoxy, cycloalkyl, aryl, heterocyclyl, and heteroaryl is independently unsubstituted or further substituted with at least one J; and wherein J independently at each occurrence is chosen from F, Cl, Br, I, OR, CN, $CF_3$, $OCF_3$, R, O, S, C(O), S(O), methylenedioxy, ethylenedioxy, N(R)$_2$, SR, S(O)R, $SO_2$R, $SO_2$N(R)$_2$, $SO_3$R, C(O)R, C(O)C(O)R, C(O)$CH_2$C(O)R, C(S)R, C(O)OR, OC(O)R, OC(O)OR, C(O)N(R)$_2$, OC(O)N(R)$_2$, C(S)N(R)$_2$, ($CH_2$)$_{0-2}$NHC(O)R, N(R)N(R)C(O)R, N(R)N(R)C(O)OR, N(R)N(R)C(O)N(R)$_2$, N(R)$SO_2$R, N(R)$SO_2$N(R)$_2$, N(R)C(O)OR, N(R)C(O)R, N(R)C(S)R, N(R)C(O)N(R)$_2$, N(R)C(S)N(R)$_2$, N(C(O)R)C(O)R, N(OR)R, C(=NH)N(R)$_2$, C(O)N(OR)R, and C(=NOR)R, wherein R is independently at each occurrence chosen from hydrogen, ($C_1$-$C_{10}$)alkyl, ($C_1$-$C_{10}$)cycloalkyl, ($C_1$-$C_{10}$)cycloalkyl($C_1$-$C_{10}$)alkyl, ($C_1$-$C_{10}$)aryl, ($C_1$-$C_{10}$)aralkyl, ($C_1$-$C_{10}$)heterocyclyl, ($C_1$-$C_{10}$)heterocyclyl($C_1$-$C_{10}$)alkyl, ($C_1$-$C_{10}$)heteroaryl, and ($C_1$-$C_{10}$)heteroaryl($C_1$-$C_{10}$)alkyl, wherein each alkyl, cycloalkyl, cycloalkylalkyl, aryl, aralkyl, heterocyclyl, heterocyclylalkyl, heteroaryl, and heteroarylalkyl is independently unsubstituted or substituted with 1-3 J.

Embodiment 84 provides the method of Embodiment 83, wherein m=n=1.

Embodiment 85 provides the method of any one of Embodiments 83-84, wherein the anhydride is chosen from succinic anhydride, glutaric anhydride, and maleic anhydride.

Embodiment 86 provides the method of any one of Embodiments 83-85, wherein rings A and B form a ring system chosen from isosorbide, isomannide, and isoidide.

Embodiment 87 provides the method of any one of Embodiments 83-86 wherein R' is chosen from ethylene, propylene, and ethenylene.

Embodiment 88 provides the method of any one of Embodiments 83-87, wherein the method is a method of making a polymer, wherein at least one R' is ($C_2$-$C_{10}$)alkenylene or ($C_2$-$C_{10}$)alkynylene, the method further comprising crosslinking the tackifier compound to provide a polymer comprising a repeating unit having the structure

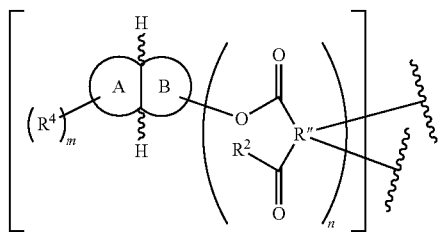

or a salt thereof;
wherein at each occurrence $R^4$ is independently selected from —OH, —OR$^3$,

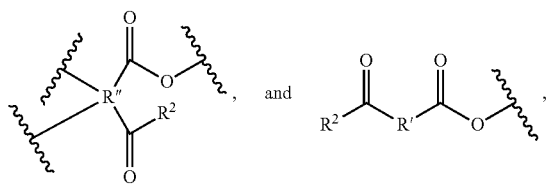

wherein at each occurrence R" is independently a ($C_2$-$C_{10}$)alkanylene bonded to at least one of a repeating unit and an end-blocking unit of the polymer at two locations, wherein R" is unsubstituted or substituted with at least one J.

Embodiment 89 provides the apparatus or method of any one or any combination of Embodiments 1-88 optionally configured such that all elements or options recited are available to use or select from.

What is claimed is:
1. A tackifier compound having the structural formula

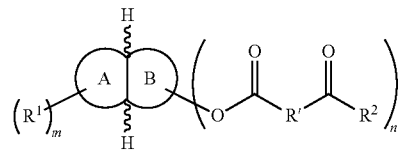

or a salt thereof;
wherein fused rings A and B are each independently chosen from ($C_5$-$C_{10}$)cycloalkyl and ($C_2$-$C_{10}$)heterocyclyl;
m and n are each independently 1-8;
at each occurrence $R^1$ is independently selected from —OH, —OR$^3$, and

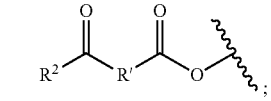

at each occurrence R' is independently chosen from ($C_2$-$C_{10}$)alkanylene, ($C_2$-$C_{10}$)alkenylene, ($C_2$-$C_{10}$)alkynylene, $C_5$-$C_{20}$(arylene), and ($C_1$-$C_{20}$)heteroarylene, wherein R' is unsubstituted or substituted;
at each occurrence $R^2$ is independently chosen from —OH, —OR$^3$, —$NH_2$, —NHR$^3$, and —NR$^3_2$;
at each occurrence $R^3$ is independently chosen from ($C_1$-$C_{10}$)alkanyl, ($C_2$-$C_{10}$)alkenyl, ($C_2$-$C_{10}$)alkynyl, $C_5$-$C_{20}$(aryl), and ($C_1$-$C_{20}$)heteroaryl, wherein $R^3$ is unsubstituted or substituted; and
fused rings A and B are each independently unsubstituted or substituted, wherein rings A and B form a ring system chosen from isosorbide, isomannide, and isoidide.

2. The tackifier compound of claim 1, wherein $R^1$ is —OH.

3. The tackifier compound of claim 1, wherein $R^1$ is

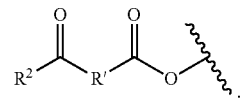

4. The tackifier compound of claim 1, wherein $R^2$ is —O($C_1$-$C_5$)alkyl or —OH.

5. The tackifier compound of claim 1, wherein at each occurrence R' is independently ($C_1$-$C_5$)alkylene, ($C_5$-$C_{10}$)aryl, or ($C_2$-$C_5$)alkenylene.

6. The tackifier compound of claim 1, wherein at each occurrence R' is independently —$CH_2$—$CH_2$—, —$CH_2$—$CH_2$—$CH_2$—, o-phenylene, or —CH=CH—.

7. The tackifier compound of claim 1, wherein the compound is

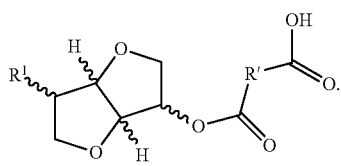

8. The tackifier compound of claim 1, wherein the compound is

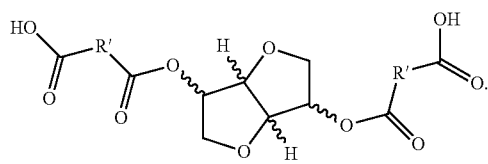

9. A reaction product of the tackifier compound of claim 1.

10. A composition comprising the tackifier compound of claim 1 and a free-radical initiator or a transition metal catalyst.

11. A system comprising:
   the tackifier compound of claim 1; and
   a first substrate;
   wherein the tackifier compound is bonded to the first substrate.

12. A method of using the tackifier compound of claim 1 comprising contacting the tackifier compound to a first substrate such that the tackifier is bonded to the first substrate.

13. The tackifier compound of claim 1, wherein the compound is chosen from

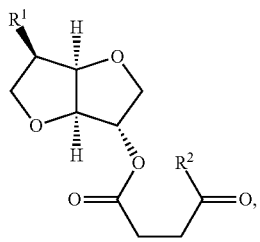

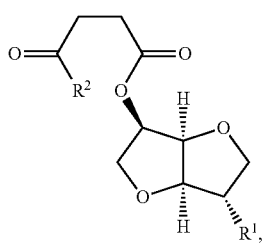

-continued

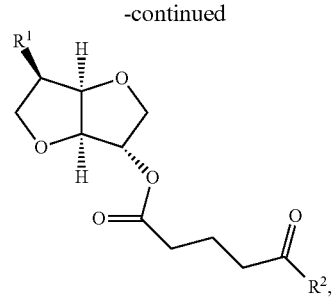

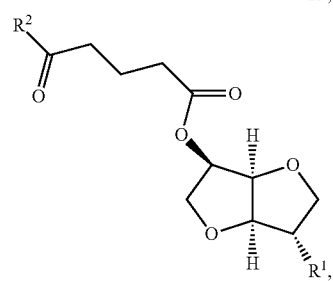

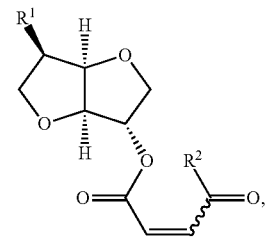

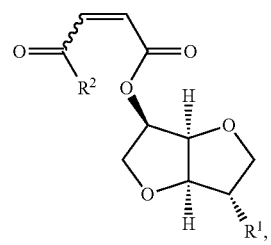

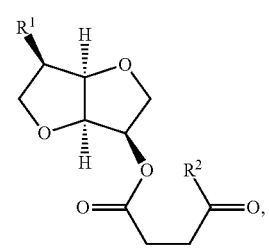

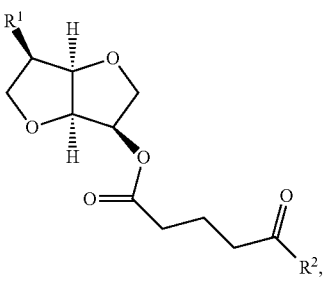

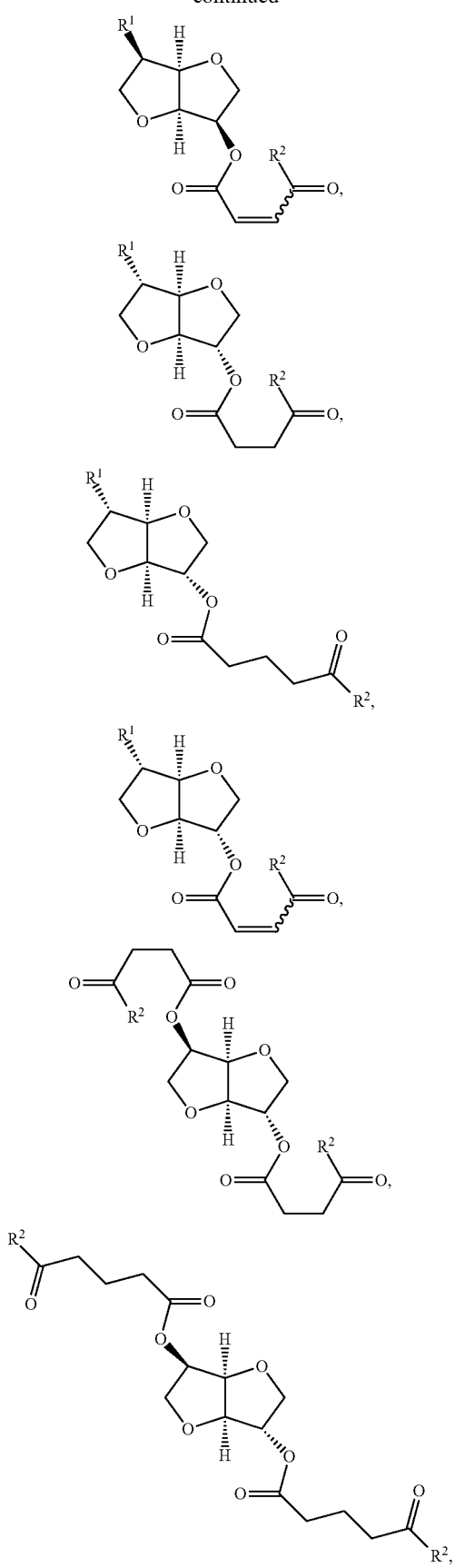
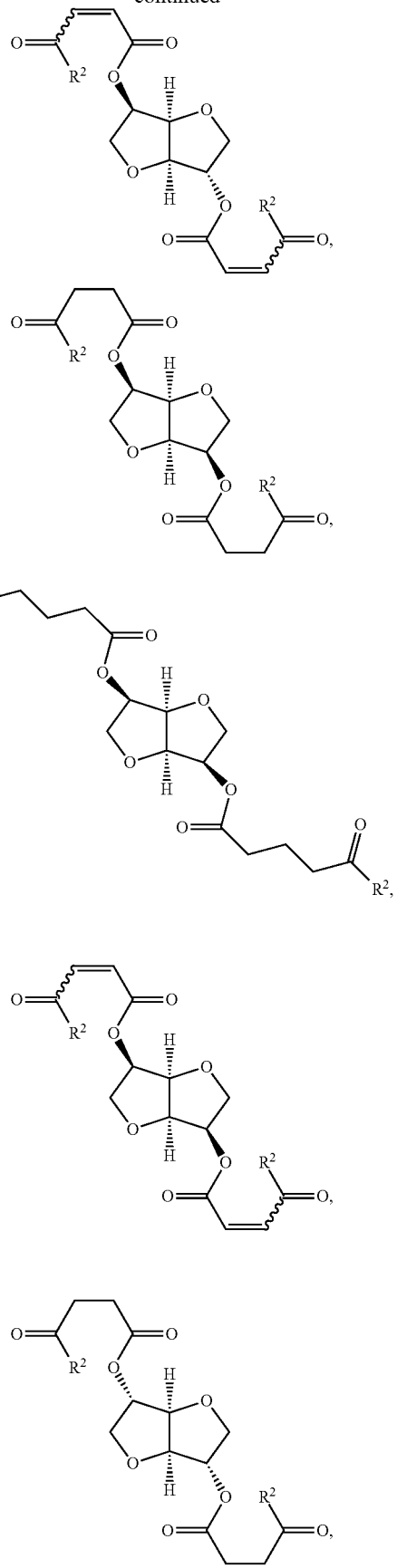

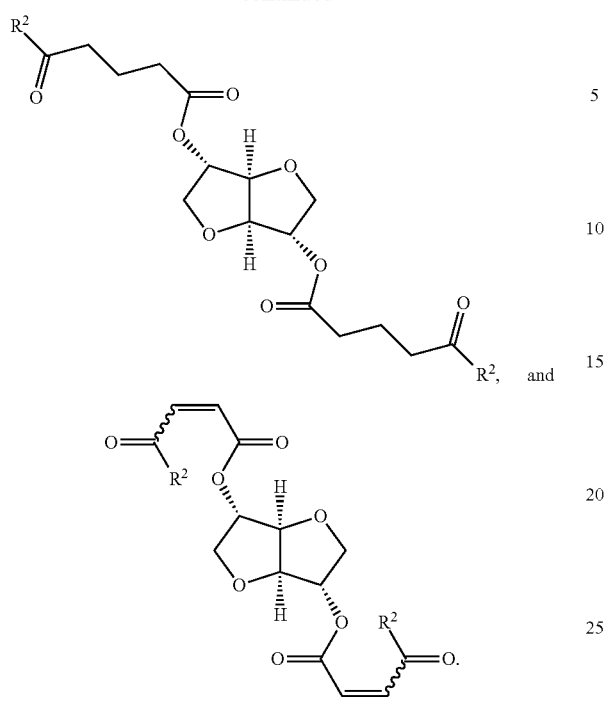
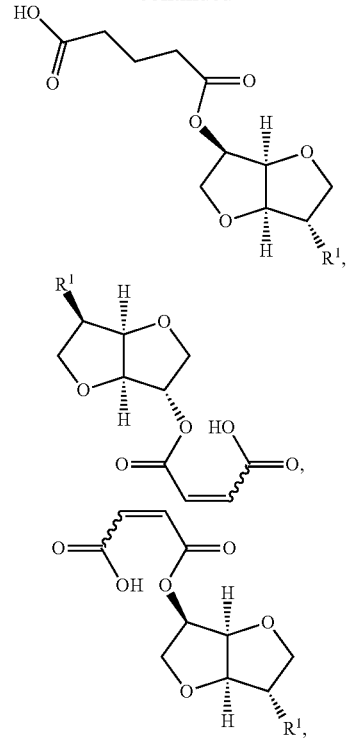
14. The tackifier compound of claim 1, wherein the compound is chosen from
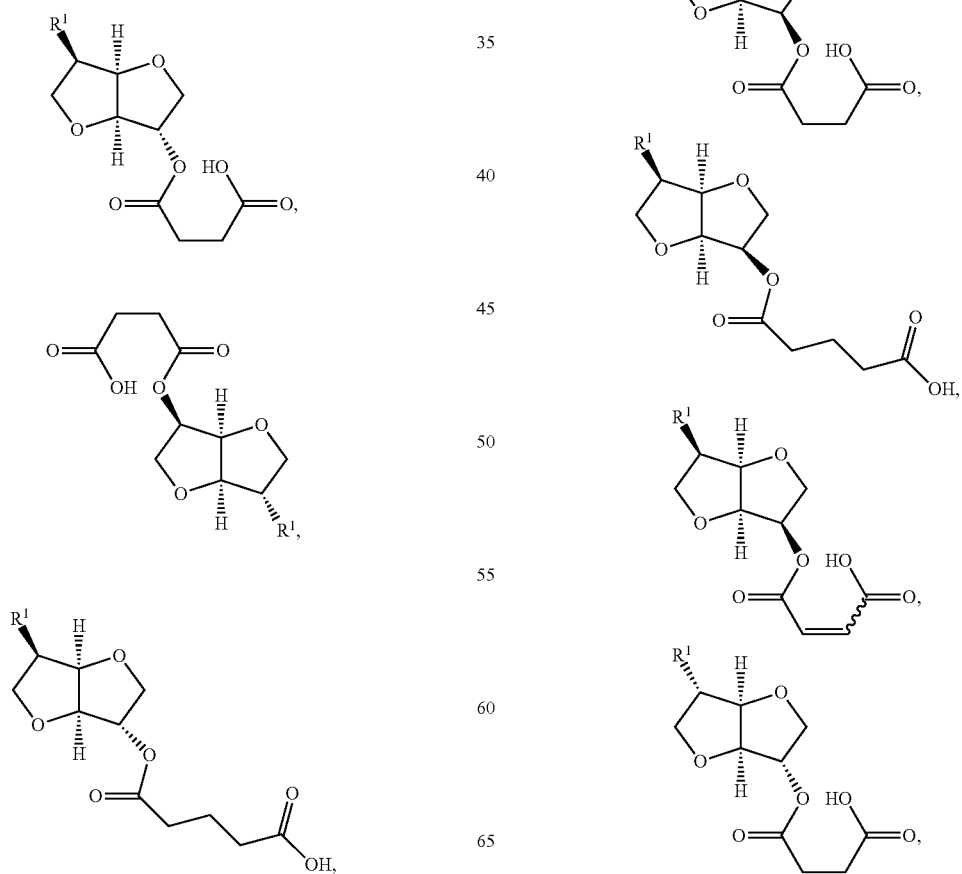
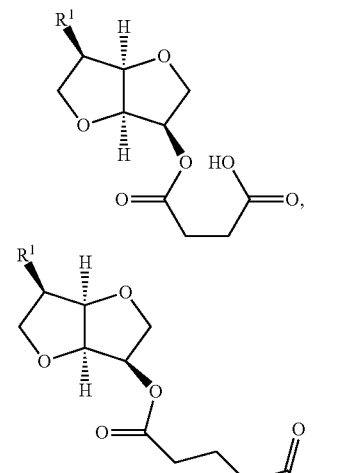
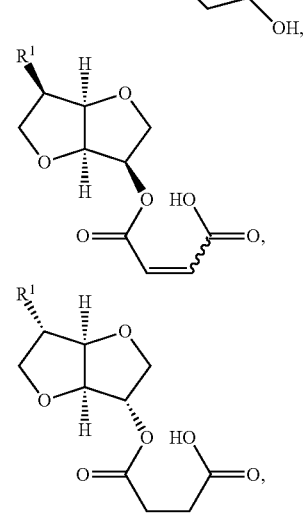

-continued
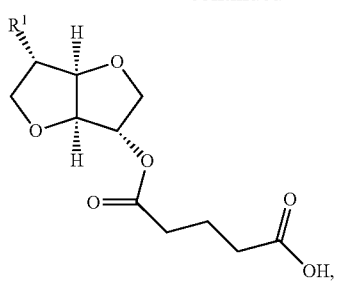
and
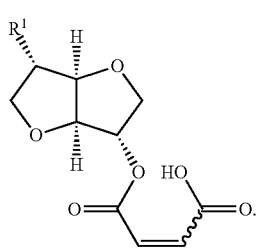
15. The tackifier compound of claim 1, wherein the compound is chosen from
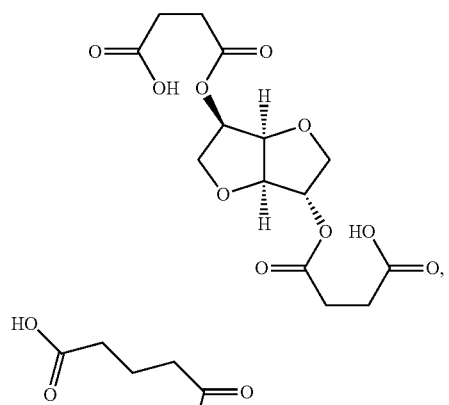
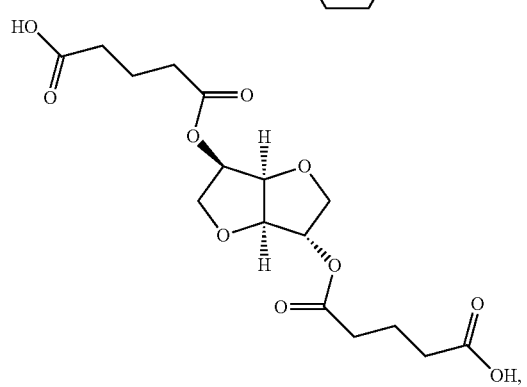
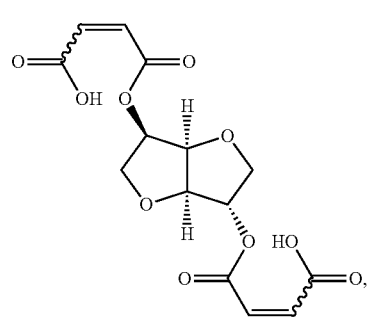
-continued
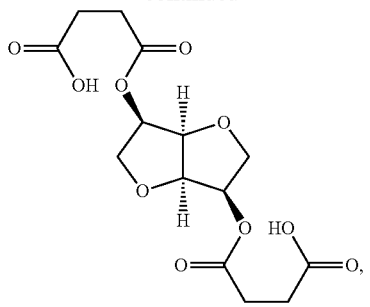
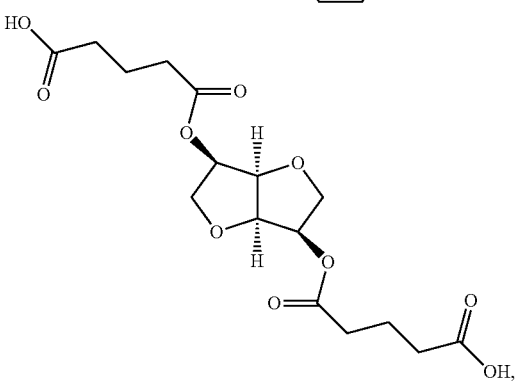
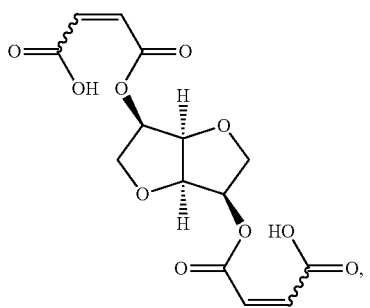
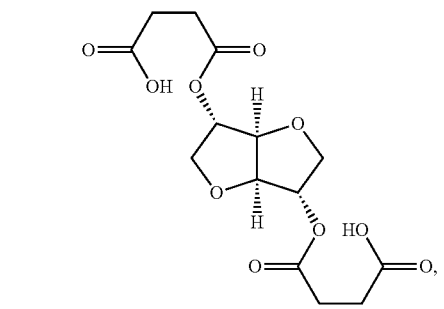
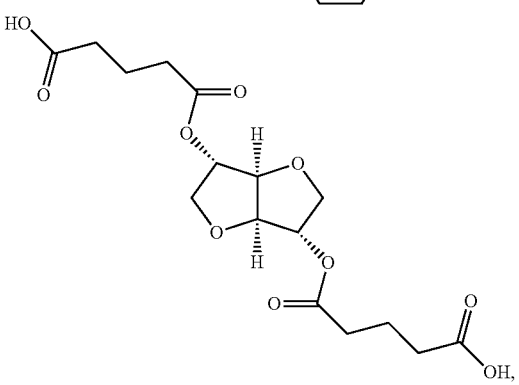
and

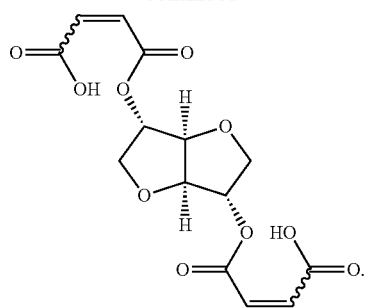
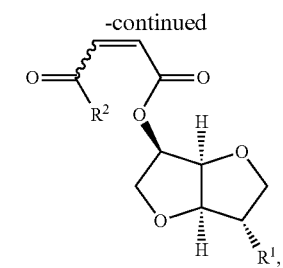
16. The tackifier compound of claim 1, wherein the compound is chosen from
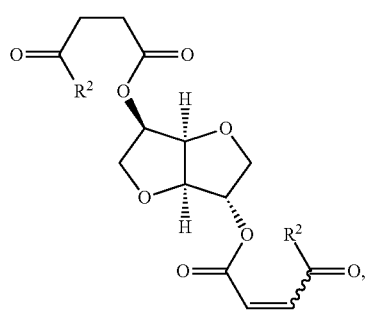
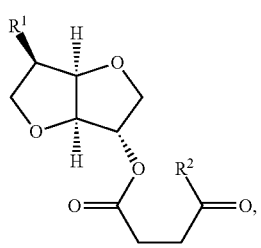
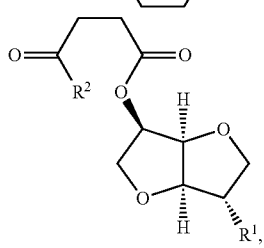
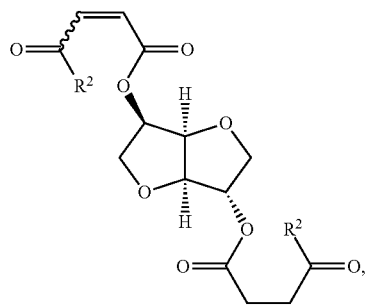
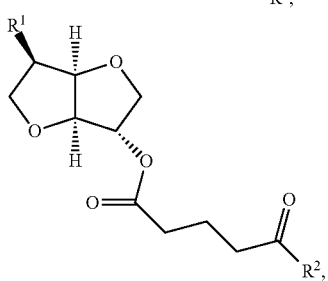
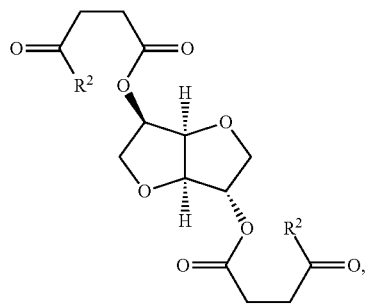
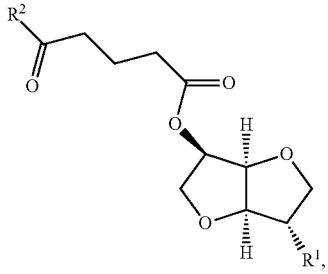
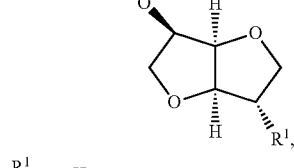
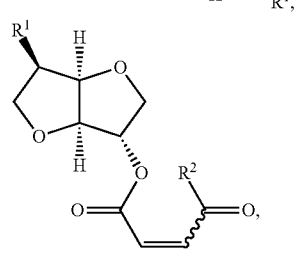
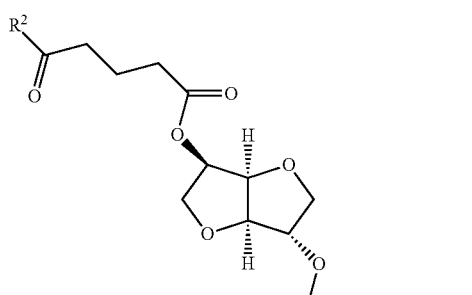
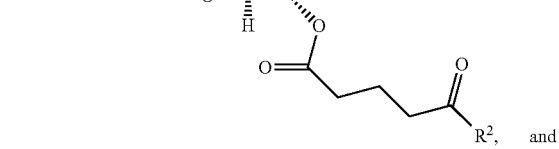
and 111
-continued
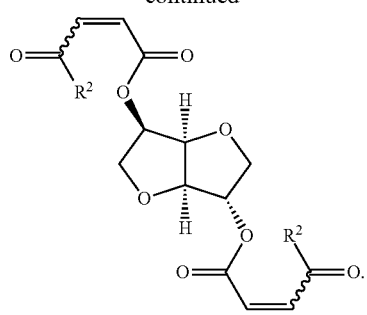
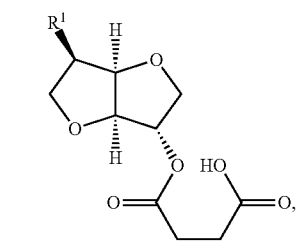
17. The tackifier compound of claim 1, wherein the compound is chosen from
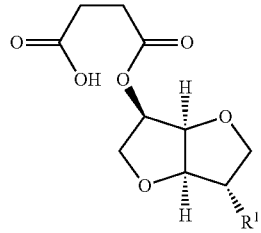
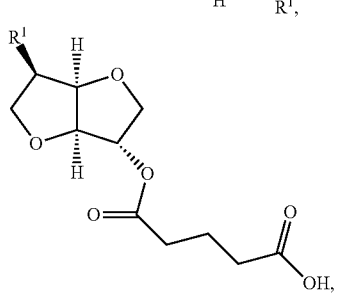
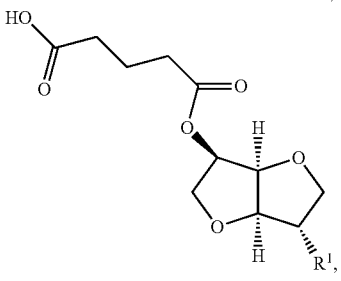
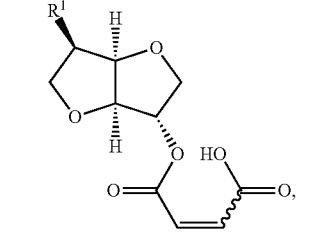
112
-continued
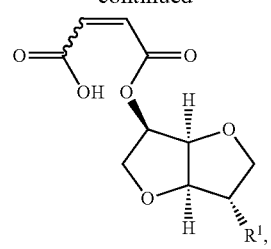
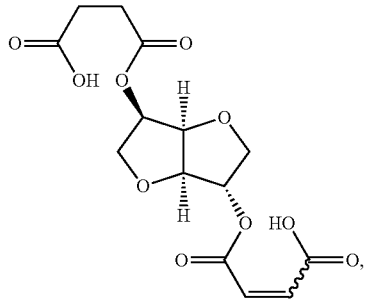
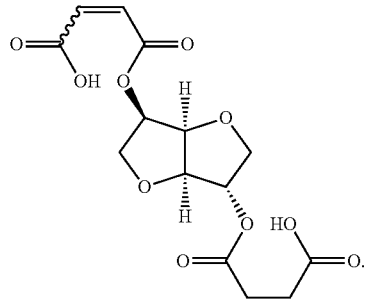
18. The tackifier compound of claim 1, wherein the compound is chosen from
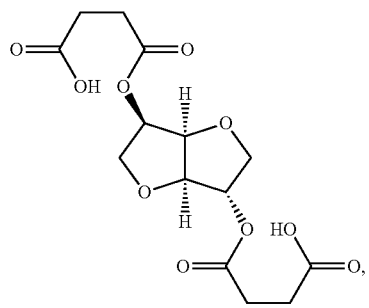
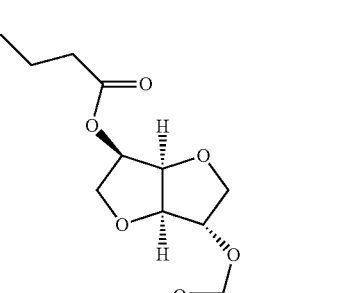
and -continued
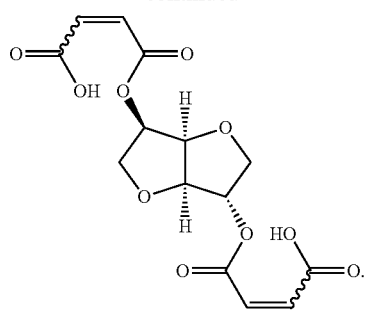
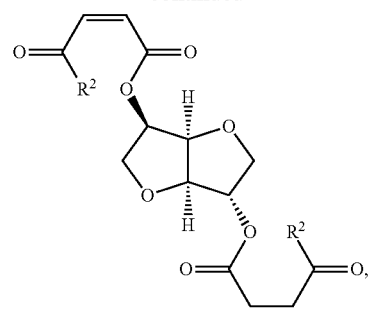
19. The tackifier compound of claim 1, wherein the compound is chosen from
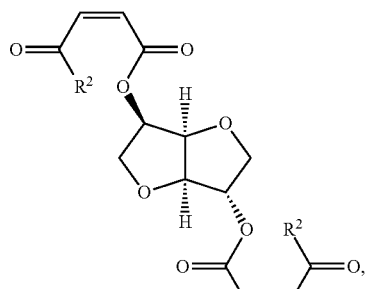
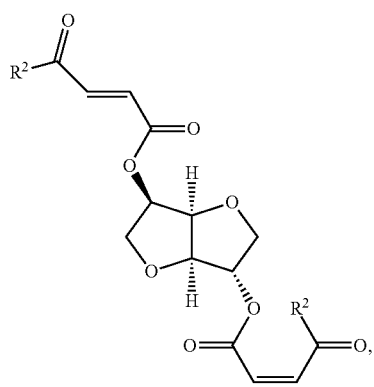
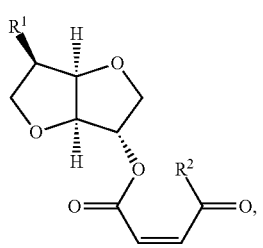
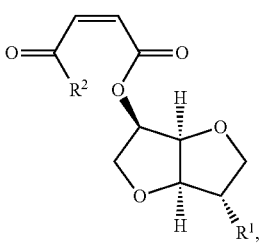
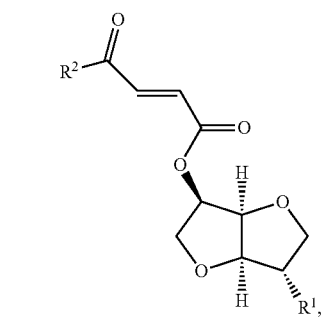
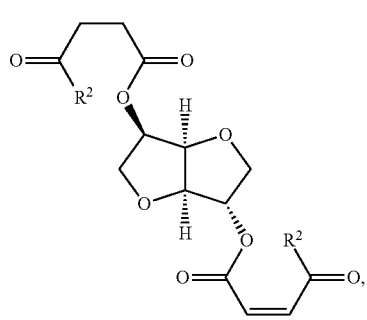
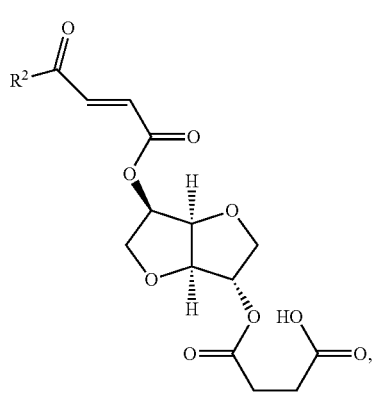

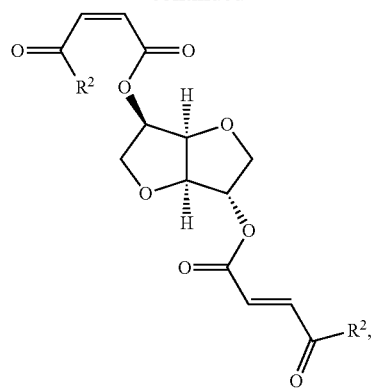
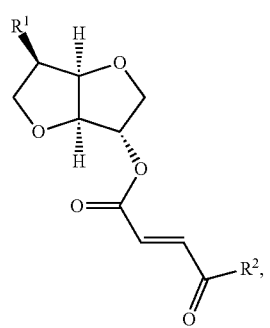
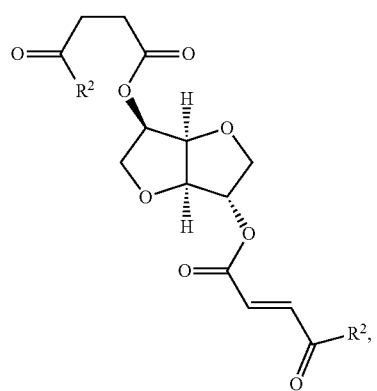
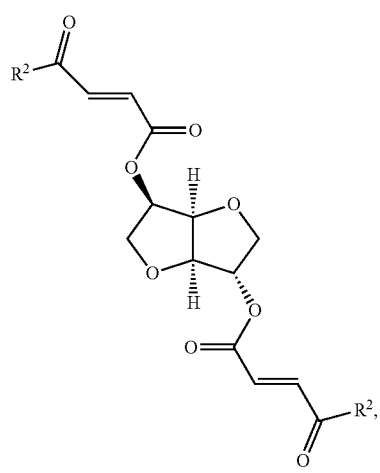
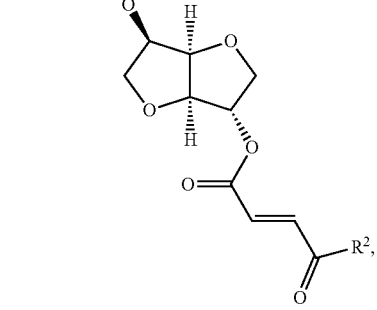
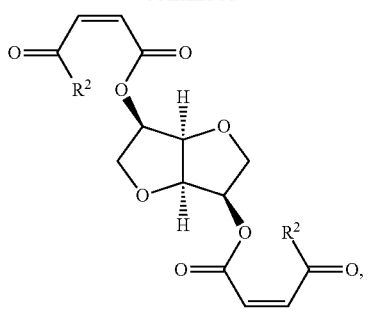
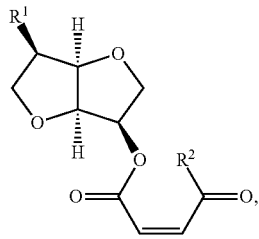
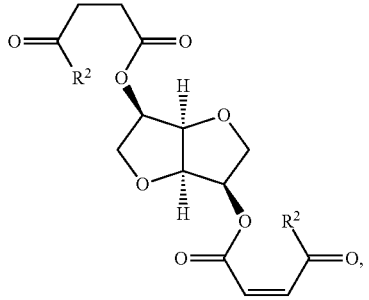
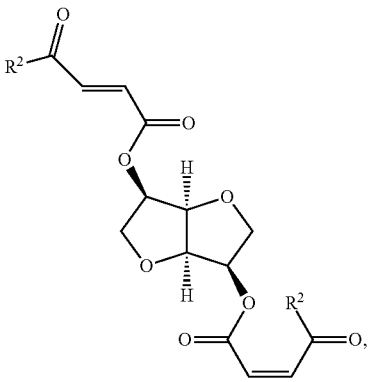
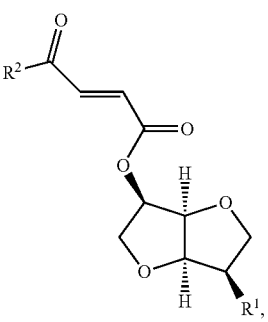

117
-continued
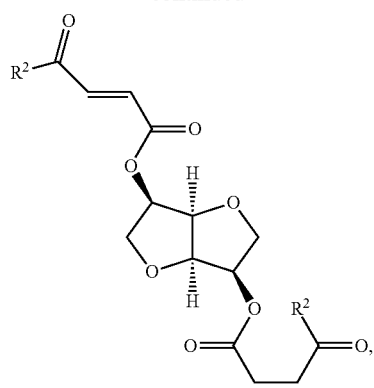
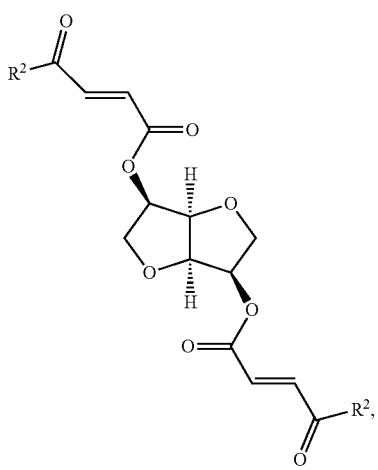
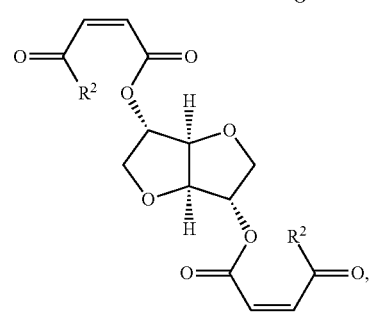
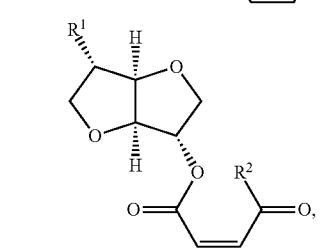
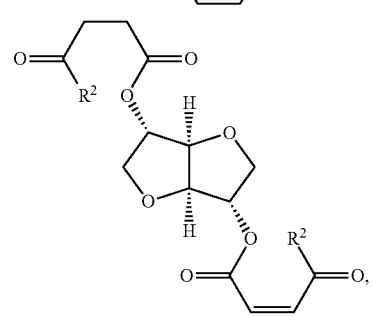
118
-continued
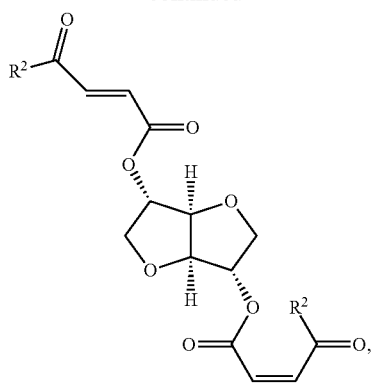
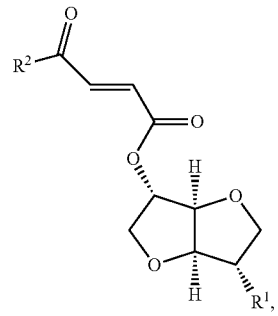
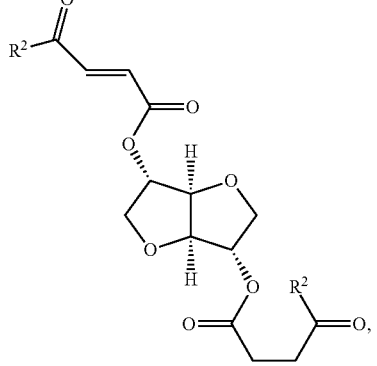
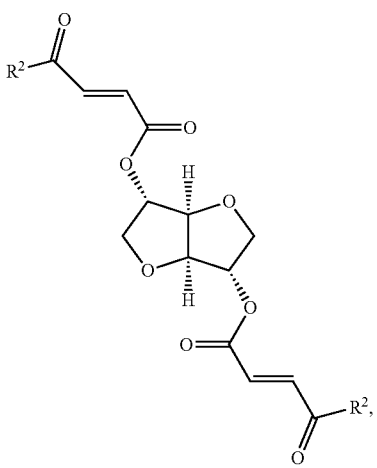

119
-continued
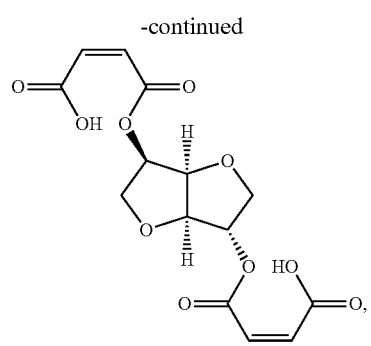
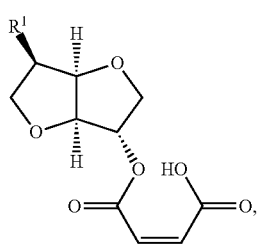
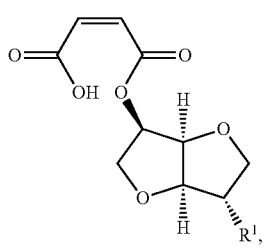
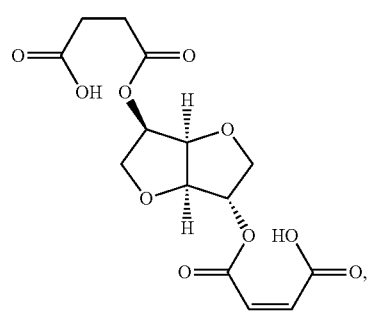
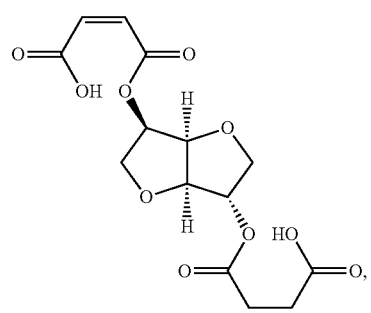
120
-continued
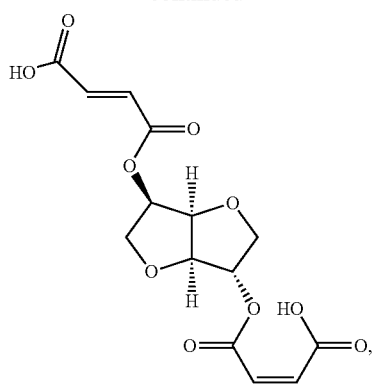
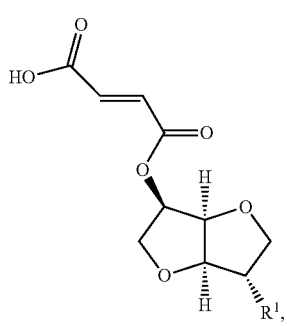
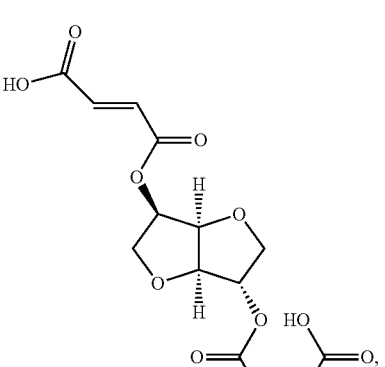
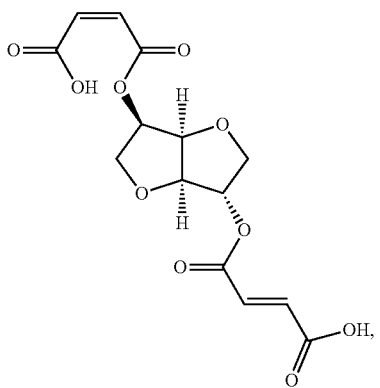

| 121 | 122 |
|---|---|
| -continued | -continued |
| 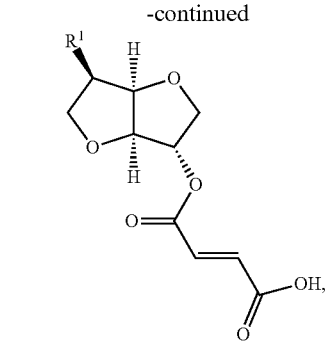 | 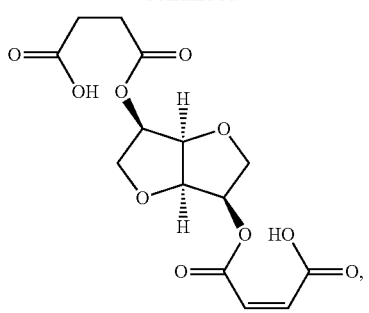 |
| 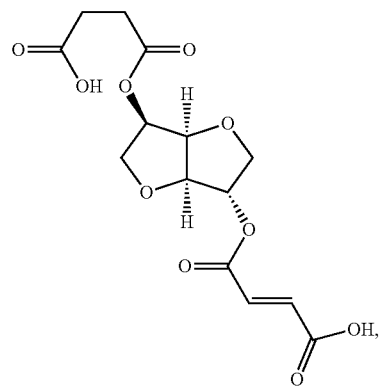 | 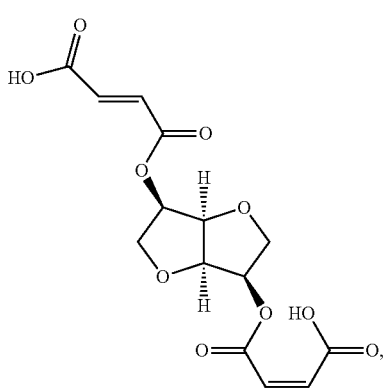 |
| 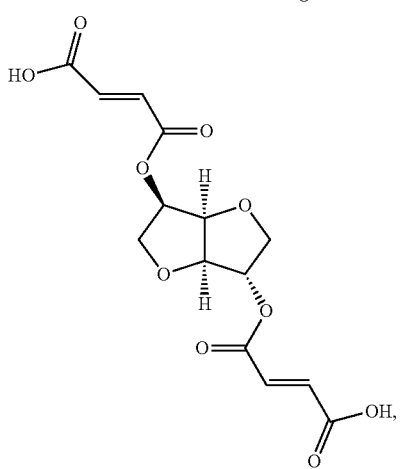 | 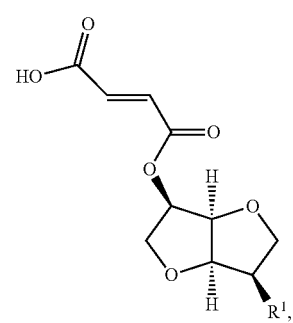 |
| 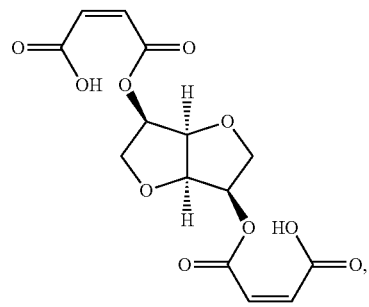 | 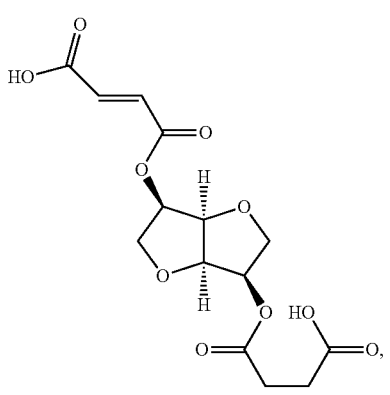 |
| 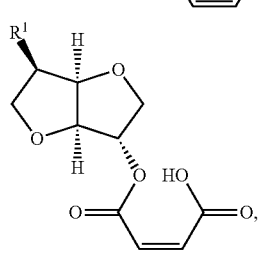 | |

123
-continued
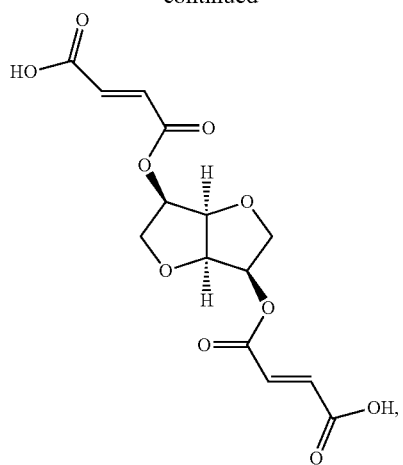
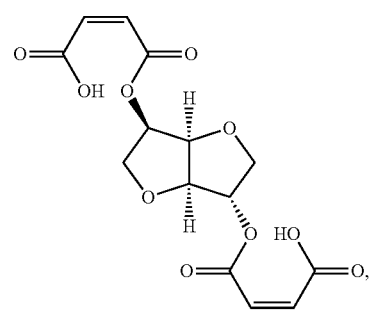
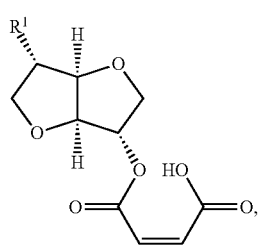
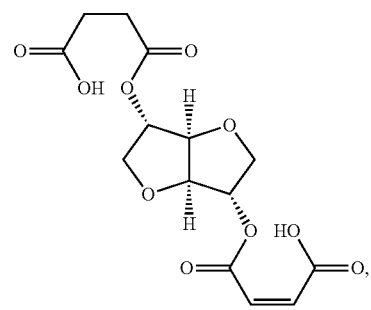
124
-continued
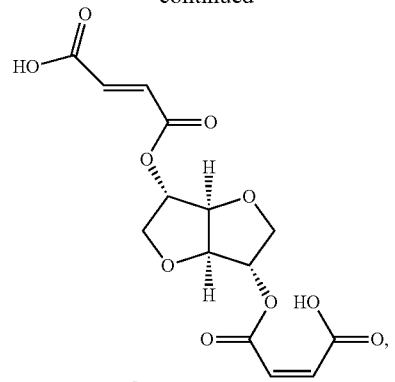
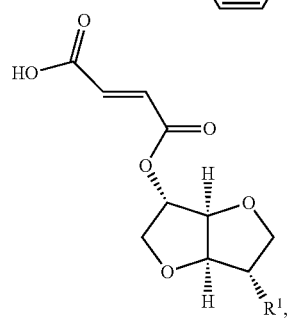
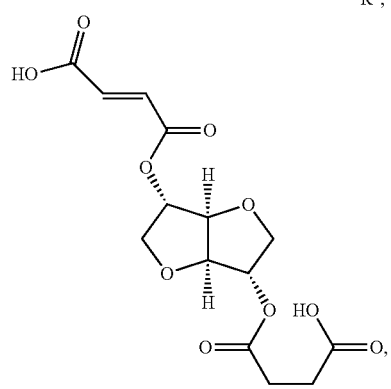
, and
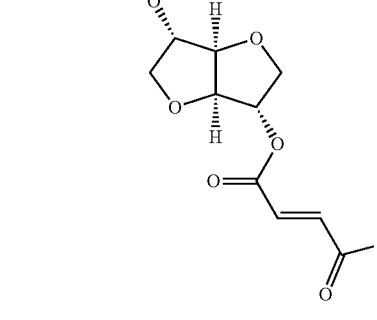
* * * * *

UNITED STATES PATENT AND TRADEMARK OFFICE
CERTIFICATE OF CORRECTION

PATENT NO. : 9,688,794 B2
APPLICATION NO. : 14/434719
DATED : June 27, 2017
INVENTOR(S) : Chen et al.

It is certified that error appears in the above-identified patent and that said Letters Patent is hereby corrected as shown below:

On the Title Page

On page 2, in Column 2, under "Other Publications", Line 25, delete "Poly(butyiene" and insert --Poly(butylene-- therefor On page 2, in Column 2, under "Other Publications", Line 45, delete "Preliminaly" and insert --Preliminary-- therefor In the Specification In Column 8, Line 50, after "2,5-", insert --,--

In Column 10, Line 54-55, delete "5H-dibenz[b,f]azepine (5H-dibenz[b,f]azepin-1-yl," and insert --5H-dibenz[b,f]azepine (5H-dibenz[b,f]azepine-1-yl,-- therefor In Column 11, Line 29, after "bromine", insert --.--

In Column 11, Line 63, after "$\Sigma M_i^2 n_i / \Sigma M_i n_i$", insert --,--

In Column 13, Line 34, delete "-CH=C-" and insert -- -CH=CH- -- therefor

In Column 24, Line 49, delete "tackfier" and insert --tackifier-- therefor

In Column 25, Line 15, delete "tackfier" and insert --tackifier-- therefor

In Column 25, Line 49, delete "tackfier" and insert --tackifier-- therefor

In Column 27, Line 37, after "manner", insert --.--

In Column 36, Line 64, delete "(C5-$C_{10}$)cycloalkyl" and insert --($C_5$-$C_{10}$)cycloalkyl-- therefor Signed and Sealed this
Seventh Day of May, 2019

Andrei Iancu
*Director of the United States Patent and Trademark Office*

In Column 37, Line 12, delete "($C_1$-$C_{20}$)heteroarylene," and insert --($C_1$-$C_{20}$)heteroarylene,-- therefor In Column 49, Line 22, delete "varaibles" and insert --variables-- therefor In Column 50, Line 19, after "isomannide", insert --:--

In Column 51, Line 39, delete "(e g ," and insert --"(e.g.,-- therefor

In Column 54, Line 11, delete "-CH-CH-)" and insert -- -CH=CH-)-- therefor

In Column 54, Line 26, delete "-CH-CH-" and insert -- -CH=CH- -- therefor

In Column 54, Line 55, delete "$cm^1$;" and insert --$cm^{-1}$;-- therefor

In Column 55, Line 37, delete "-CH-CH-)" and insert -- -CH=CH-)-- therefor

In Column 55, Line 52, delete "-CH-CH-" and insert -- -CH=CH- -- therefor

In Column 55, Line 64, delete "J =5.8" and insert --J=5.8-- therefor

In Column 56, Line 16, delete "ppm;$^{13}$C" and insert --ppm; $^{13}$C-- therefor In Column 56, Line 50, delete "-CH-CH-)" and insert -- -CH=CH-)-- therefor In Column 56, Line 65, delete "-CH-CH-" and insert -- -CH=CH- -- therefor In Column 57, Line 51, delete "ν=1739 $cm^{-1}$;$^1$H" and insert --$ν_{max}$=1739 $cm^{-1}$; $^1$H-- therefor In Column 58, Line 16, after "mm", insert --.--

In Column 60, Line 34, delete "($C_1$-$C_{10}$)cycloalkyl," and insert --($C_1$-$C_{10}$)cycloalkyl,-- therefor In Column 61, Line 39, delete "$Ag_+$," and insert --$Ag^+$,-- therefor In Column 61, Line 42, delete "-OH ." and insert -- -OH.-- therefor In Column 61, Line 53, delete "-OH ." and insert -- -OH.-- therefor In Column 63, Line 24-30, delete "  " and insert

CERTIFICATE OF CORRECTION (continued)
U.S. Pat. No. 9,688,794 B2

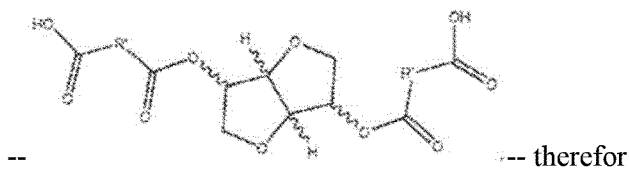
-- ---- therefor

In Column 79, Line 51-66, delete " 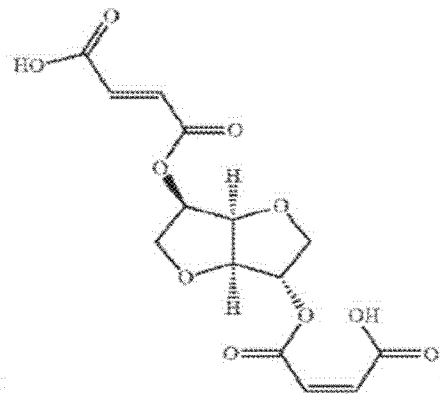 " and insert

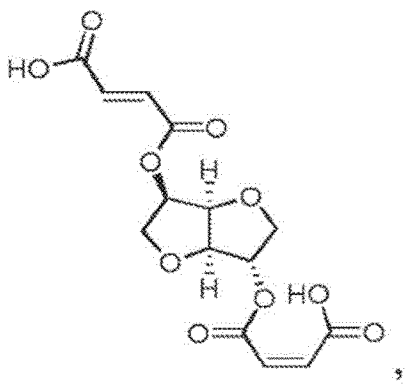
-- ---- therefor

In Column 85, Line 58, delete "$(C_1-C_{10})$heterocyclyl$(C_0-C_{10})$alkyl," and insert --$(C_1-C_{10})$heterocyclyl$(C_0-C_{10})$alkyl,-- therefor In the Claims In Column 100, Line 24-25, in Claim 1, delete "$(C_2-C_{10})$heterocyclyl;" and insert --$(C_2-C_{10})$heterocyclyl;-- therefor